United States Patent
Logue et al.

(10) Patent No.: US 6,279,379 B1
(45) Date of Patent: Aug. 28, 2001

(54) APPARATUS AND METHODS FOR PERFORMING ACOUSTICAL MEASUREMENTS

(75) Inventors: Raymond C. Logue, Somers; Don N. Sirota; Patrick S. Lee, both of Poughkeepsie, all of NY (US)

(73) Assignee: Lorex Industries, Inc., Poughkeepsie, NY (US)

( * ) Notice: Subject to any disclaimer, the term of this patent is extended or adjusted under 35 U.S.C. 154(b) by 0 days.

(21) Appl. No.: 09/443,519

(22) Filed: Nov. 19, 1999

Related U.S. Application Data

(63) Continuation of application No. PCT/US99/08362, filed on Apr. 16, 1999, which is a continuation-in-part of application No. 09/062,112, filed on Apr. 17, 1998, now Pat. No. 6,116,080.

(51) Int. Cl.[7] .............................. G01N 29/02; G01F 1/66; E21B 47/00

(52) U.S. Cl. .............................. 73/24.01; 73/579; 73/602; 324/76.21; 324/76.33

(58) Field of Search .................................. 73/24.01, 23.2, 73/597, 579, 602; 324/76.21, 76.33

(56) References Cited

U.S. PATENT DOCUMENTS

| 4,175,423 | 11/1979 | Braun et al. ............................... 73/30 |
| 4,246,773 | 1/1981 | Haruta ........................................ 73/24 |
| 4,555,932 * | 12/1985 | Crosby, Jr. et al. ...................... 73/24 |

(List continued on next page.)

FOREIGN PATENT DOCUMENTS 2215049  9/1989 (GB) .

OTHER PUBLICATIONS

Bhatia, *Ultrasonic Absorption*, 1967, Oxford University Press, reprinted by Dover Publications, Inc., New York, 1985.

Cadet et al. "Ultrasonic time–of–flight method for online quantitation of semiconductor gases", Ultrasonics Symposium, Proceedings, New York, Institute of Electrical and Electronic Engineers, 1991, 295–300.

(List continued on next page.)

*Primary Examiner*—Daniel S. Larkin
*Assistant Examiner*—David J. Wiggins
(74) *Attorney, Agent, or Firm*—Maurice M. Klee

(57) ABSTRACT

Apparatus (15, 30) and methods for performing acoustical measurements are provided having some and preferably all of the following features: (A) the system (15, 30) is operated under near-field conditions; (B) the piezoelement (40) or piezoelements (40, 48) used in the system are (i) mechanically (41, 49) and electrically (13, 16) damped and (ii) efficiently electrically coupled to the signal processing components of the system; (C) each piezoelement (40, 48) used in the system includes an acoustical transformer (42, 50) for coupling the element to a gaseous test medium (9); (D) speed of sound is determined from the time difference between two detections of an acoustical pulse (81, 82) at a receiver (40, FIG. 3; 48, FIG. 7); (E) cross-correlation techniques are employed to detect the acoustical pulse at the receiver; (F) forward and inverse Fourier transforms employing fast Fourier transform techniques are used to implement the cross-correlation techniques; in such a mathematical manner that the peak of the cross-correlation function corresponds to the detection of a pulse at the receiver and (G) stray path signals through the body (31) of the acoustic sensor (15, 30) are removed from detected signals prior to signal analysis. Techniques are also provided for performing acoustical measurements on gases whose thermodynamic properties have not been measured and on mixtures of compressible gases. Methods and apparatus (29) for performing feedback control of a gas of interest in a mixture of that gas and a carrier gas are provided in which the controlled variable is the flow of the carrier gas.

20 Claims, 40 Drawing Sheets

U.S. PATENT DOCUMENTS

| | | | |
|---|---|---|---|
| 4,576,047 | * | 3/1986 | Lauer et al. .............................. 73/597 |
| 4,596,133 | | 6/1986 | Smalling et al. ......................... 73/24 |
| 4,616,501 | * | 10/1986 | Mechlenburg ............................ 73/24 |
| 4,630,482 | * | 12/1986 | Traina ..................................... 73/597 |
| 4,835,708 | | 5/1989 | Frans ..................................... 364/497 |
| 4,850,220 | | 7/1989 | Asano et al. ............................ 73/196 |
| 5,060,507 | | 10/1991 | Urmson et al. ...................... 73/24.01 |
| 5,060,514 | * | 10/1991 | Aylaworth ............................ 73/24.01 |
| 5,154,078 | * | 10/1992 | Codazzi .................................. 73/155 |
| 5,159,843 | | 11/1992 | Shakkottai et al. ................. 73/24.05 |
| 5,235,844 | | 8/1993 | Bonne et al. ........................ 73/24.01 |
| 5,247,826 | * | 9/1993 | Frola et al. ........................... 73/24.01 |
| 5,285,675 | * | 2/1994 | Colgate et al. ........................ 73/23.2 |
| 5,299,576 | * | 4/1994 | Shiba et al. ...................... 128/660.07 |
| 5,309,221 | | 5/1994 | Fischer et al. ........................ 356/355 |
| 5,313,820 | | 5/1994 | Aylsworth ............................ 73/24.01 |
| 5,325,703 | | 7/1994 | Magori ................................. 73/23.32 |
| 5,351,522 | | 10/1994 | Lura ..................................... 73/24.01 |
| 5,369,979 | | 12/1994 | Aylsworth et al. .................. 73/24.01 |
| 5,392,635 | | 2/1995 | Cadet et al. .......................... 73/24.01 |
| 5,768,937 | | 6/1998 | Wajid et al. .......................... 73/24.06 |
| 5,948,967 | * | 9/1999 | Cadet et al. .......................... 73/24.01 |
| 6,138,512 | * | 10/2000 | Roberts et al. ......................... 73/570 |

OTHER PUBLICATIONS

Chung et al., "Applications of kinetic gas theories and multiparameter correlation for prediction of dilute gas viscosity and thermal conductivity," Industrial & Engineering Chemistry Fundamentals, 1984, 23:8–13.

Cramer, H., *Mathematical Methods of Statistics*, Princeton University Press, 1946.

Desilets et al., "The Design of Efficient Broad—Band Piezoelectric Transducers", IEEE Transactions on Sonics and Ultrasonics, vol. SU–25, No. 3, May 1978, 115–125.

Born, M., *Atomic Physics*, J. Dougall trans., Hafner Publishing Company, New York, 1946.

Elmore et al., *Physics of Waves*, 1969, McGraw–Hill Book Company, reprinted by Dover Publications, Inc., NY, 1985.

Fisher, R. A., On an Absolute Criterion for Fitting Frequency Curves, Mess. of Math., 41, pp. 155–160, 1912.

Folkestad et al. "Chirp Excitation of Ultrasonic Probes and Algorithm for Filtering Transit Times in High–Rangeability Gas Flow Metering", IEEE Transactions on Ultrasonics, Ferroelectronics and Frequency Control, vol. 40, No. 3, May 1993, 193–215.

Gooberman, *Ultrasonics*, Hart Publishing Company, Inc., NYC, 1969.

Hallewell et al. "A simplified formula for the analysis of binary gas containing a low concentration of a heavy vapor in a lighter carrier", Ultrasonics Symposium, Proceedings, New York, Institute of Electrical and Electronic Engineers, 1994, 1311–1316.

Hallewell et al., "A Sonar–Based Technique for the Ratiometric Determination of Binary Gas Mixtures", Nuclear Instruments and Methods in Physics Research, A264, 1988, North–Holland, Amsterdam, 219–234.

Hunter, *Acoustics*, Englewood Cliffs, N.J., Prentice–Hall, Inc., 1957.

Inoue et al. "Design of Ultrasonic Transducer with Multiple Acoustic Matching Layers for Medical Application", IEEE Transactions on Ultrasonics, Ferroelectrics and Frequency Control, vol. UFFC–34, No. 1, Jan. 1987, 8–16.

Joos et al., "An ultrasonic sensor for the analysis of binary gas mixtures", Sensors and Actuators, B. 15–16, 1993, 413–419.

Polturak et al. "Precision acoustic gas analyzer for binary mixtures", Rev. Sci. Instrum. 57 (11), American Institute of Physics, Nov. 1986, 2837–2841.

Potzick, "On the Accuracy of Low Flow Rate Calibrations at the National Bureau of Standards", ISA Transactions, vol. 25, No. 2, 1986, 19–23.

Rayleigh, *The Theory of Sound*, 1877 treatise, reprinted by Dover Publ., New York, 1945.

Reid et al. "The Properties of Gases and Liquids", Fourth Edition McGraw–Hill, Inc., New York, 1987, 413–414.

Sorensen et al., Real–valued algorithms for the FFT Proceedings: ICASSP 87, 1987 International Conference on Acoustics, Speech, and Signal Processing (Cat. No. 8CH2396–0), pp. 1831–1834, vol. 3., p. 2425 vol. 4.

Stagg, J.P., "Reagent Concentration Measurements in Metal Organic Vapour Phase Epitaxy (MOVPE) Using and Ultrasonic Cell", Chemtronics, vol. 3, Mar. 1988, Harlow, Essex, UK, 44–49.

Tipler, *Foundations of Modern Physics*, Worth Publishers, Inc., New York, 1969.

Van Trees, Harry L., *Detection, Estimation, and Modulation Theory*, John Wiley & Sons, Inc., New York, 1968.

Yamshikov, et al., Defektoshkopiia, Academy of Sciences of the USSR, Moscow, USSR, 1986, vol. 3, 13–20 (in Russian).

Yamishikov et al."On the improvement of the ultrasonic devices sensitivity", Defectoscopy, Academy of Sciences of the USSR, Moscow, USSR, 1986, vol. 3, 13–20 (English translation of #33 above).

Zeira et al., "Realizable Lower Bounds for Time Delay Estimation," IEEE Transactions on Signal Processing, vol. 41, No. 11, Nov. 1993.

Zeira et al., "Realizable Lower Bounds for Time Delay Estimation: Part 2—Threshold Phenomena," IEEE Transactions on Signal Processing, vol. 42, No. 5, May 1994.

Zeira, A., Realizable Lower Bounds for Time Delay Estimation, Ph.D. dissertation, Yale University, New Haven, CT, 1991.

Zipser et al. "Acoustic sensor for ternary gas analysis", Sensor and Actuators, B. 26–27, 1995, 195–198.

* cited by examiner

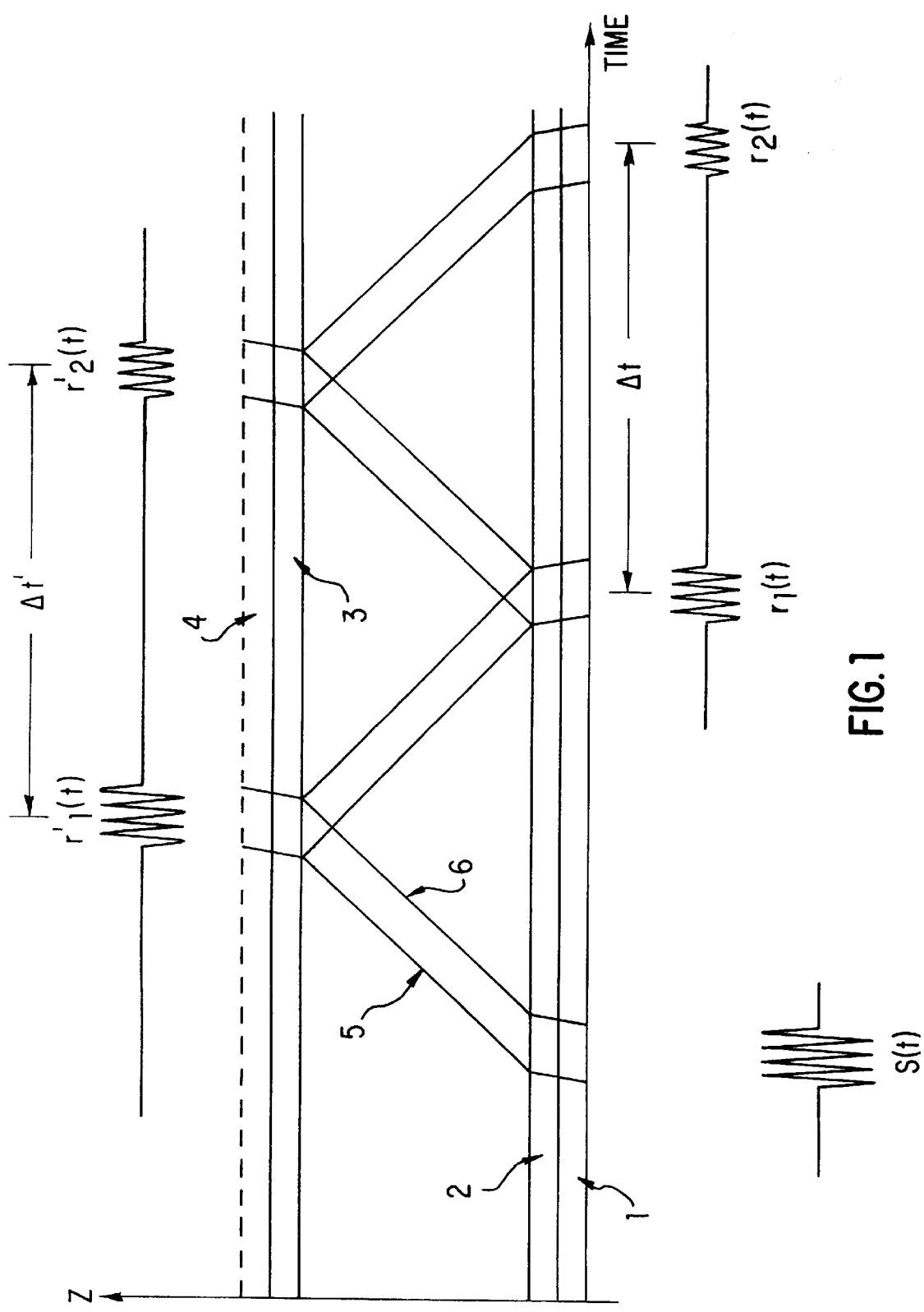

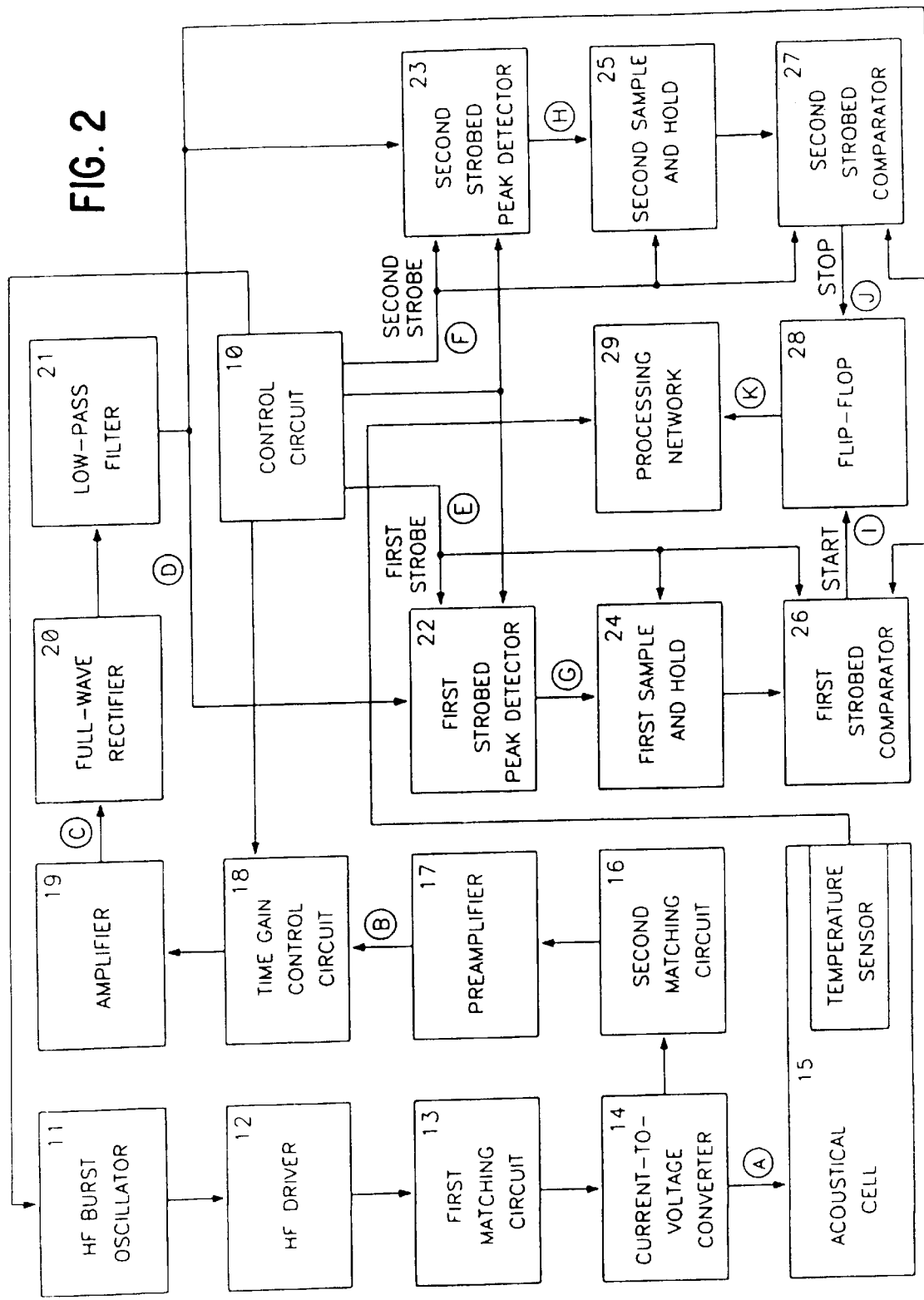

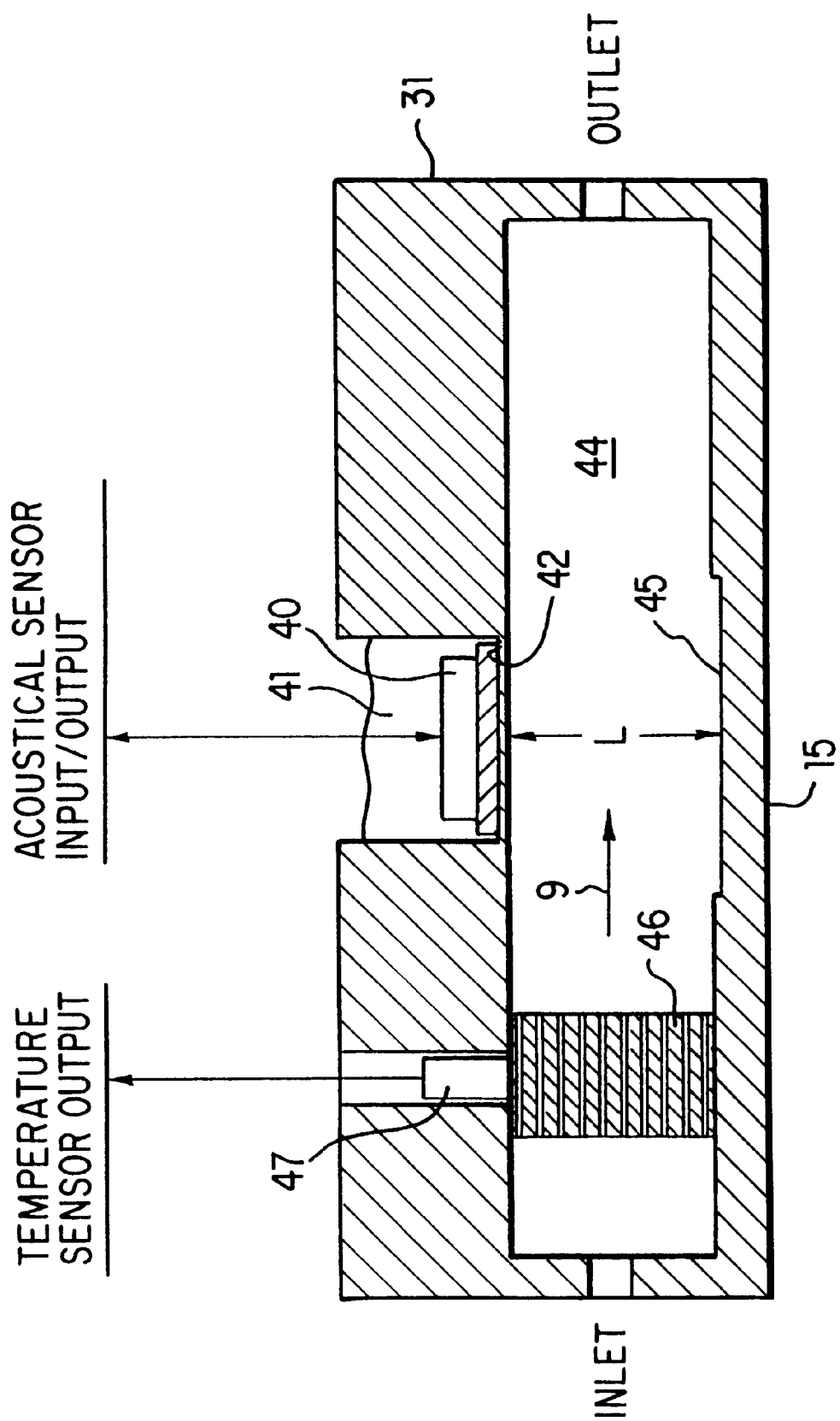

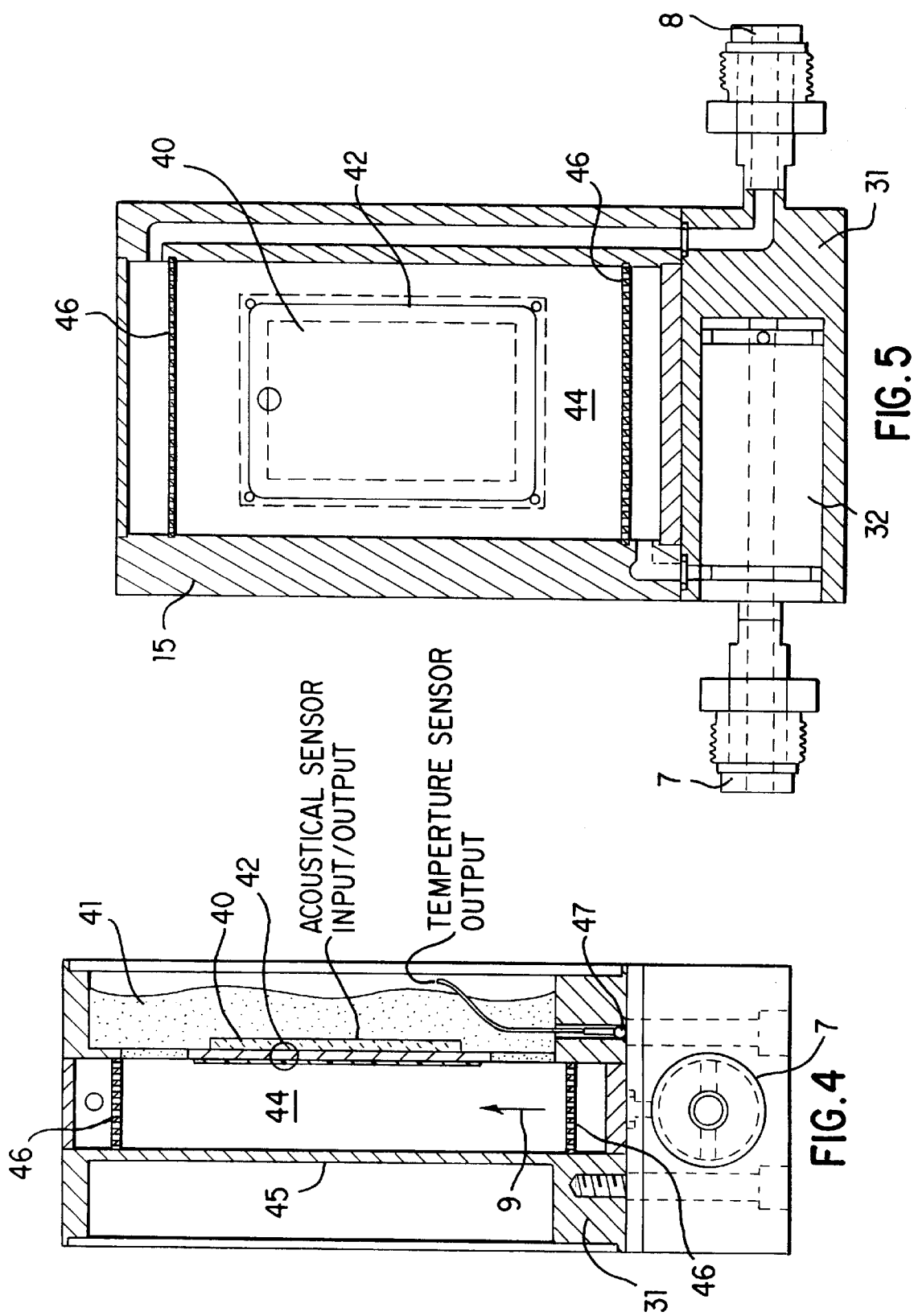

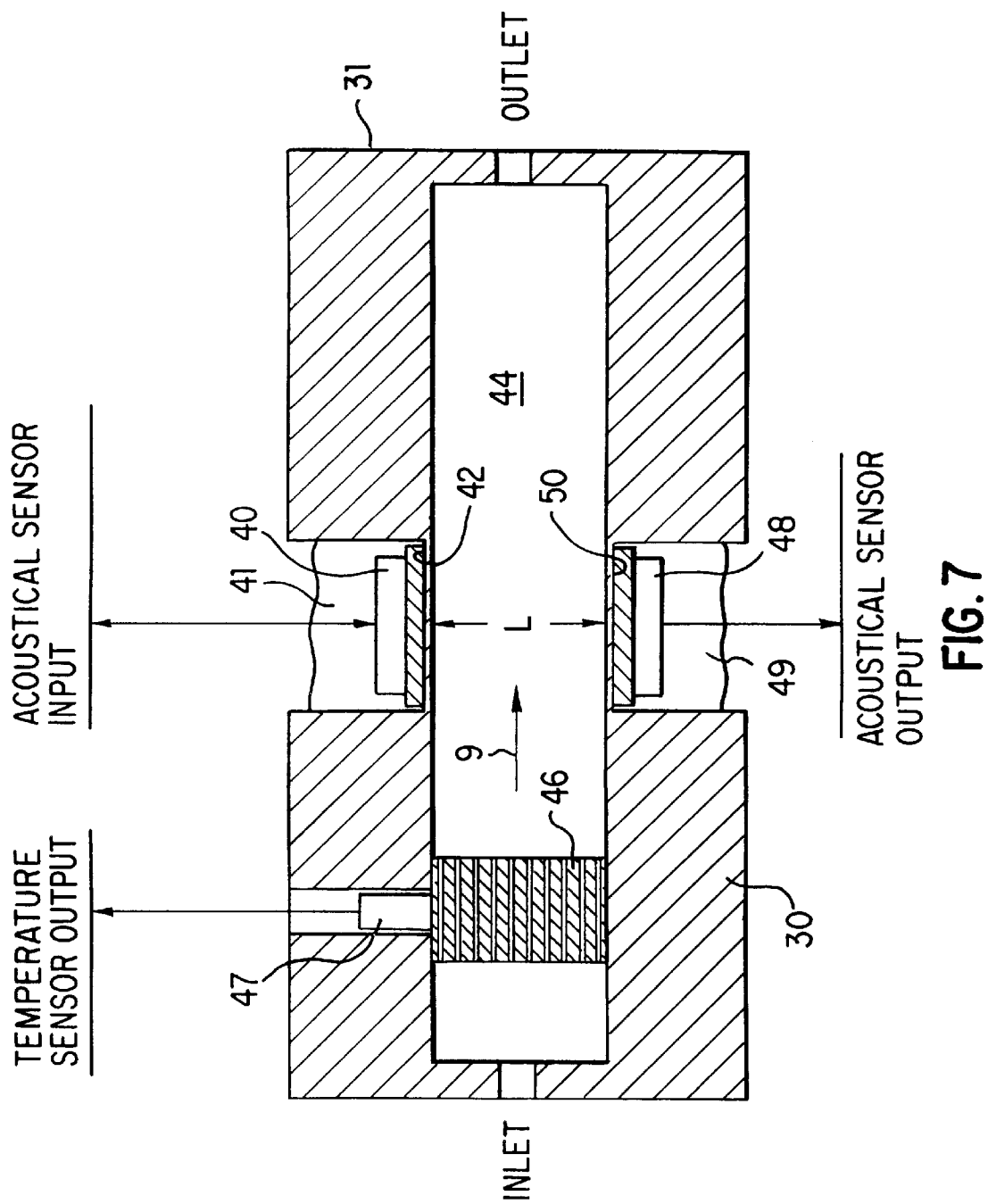

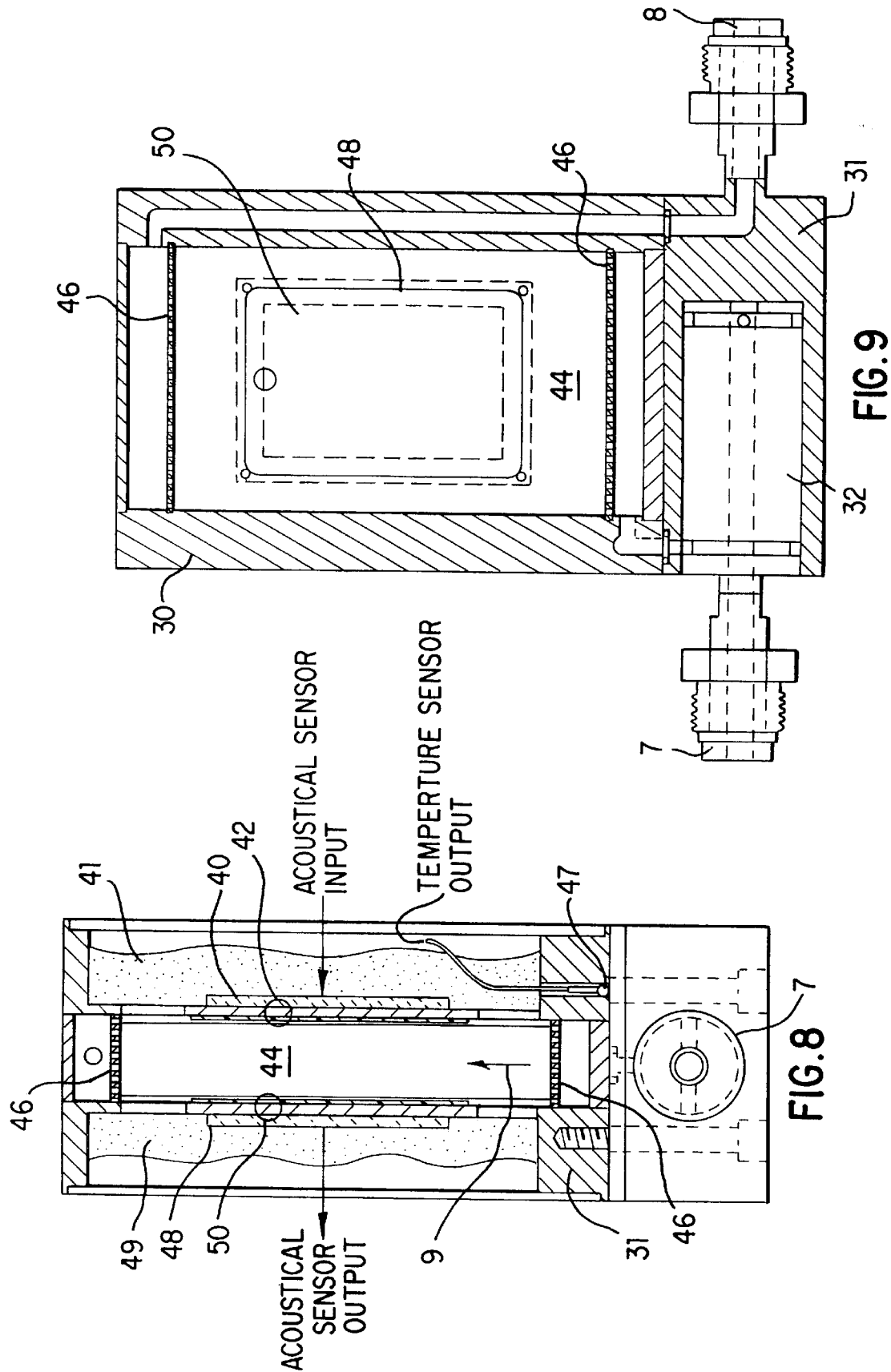

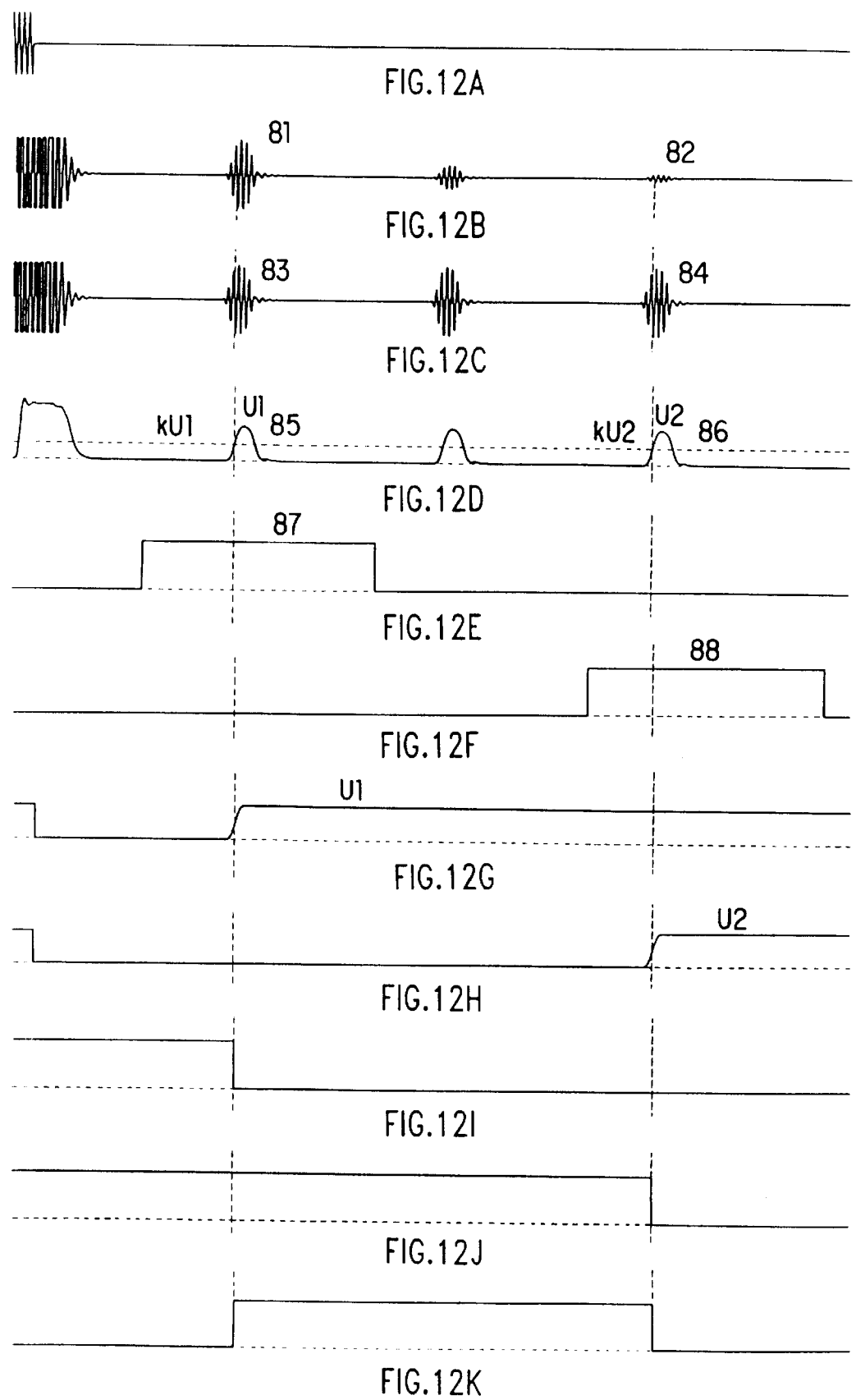

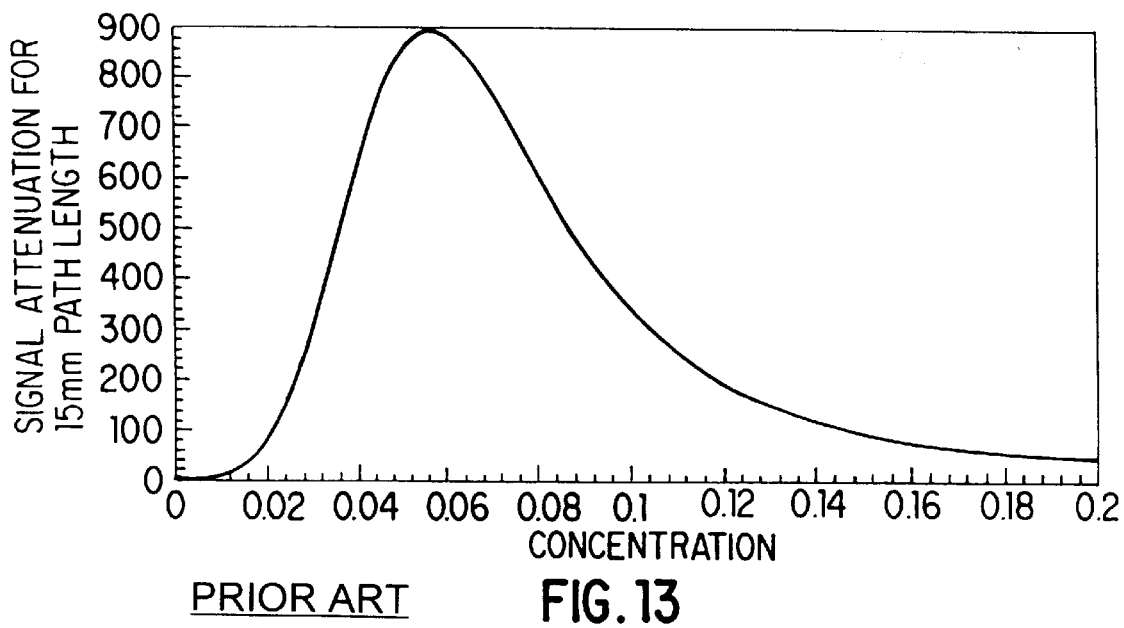
PRIOR ART  FIG. 13
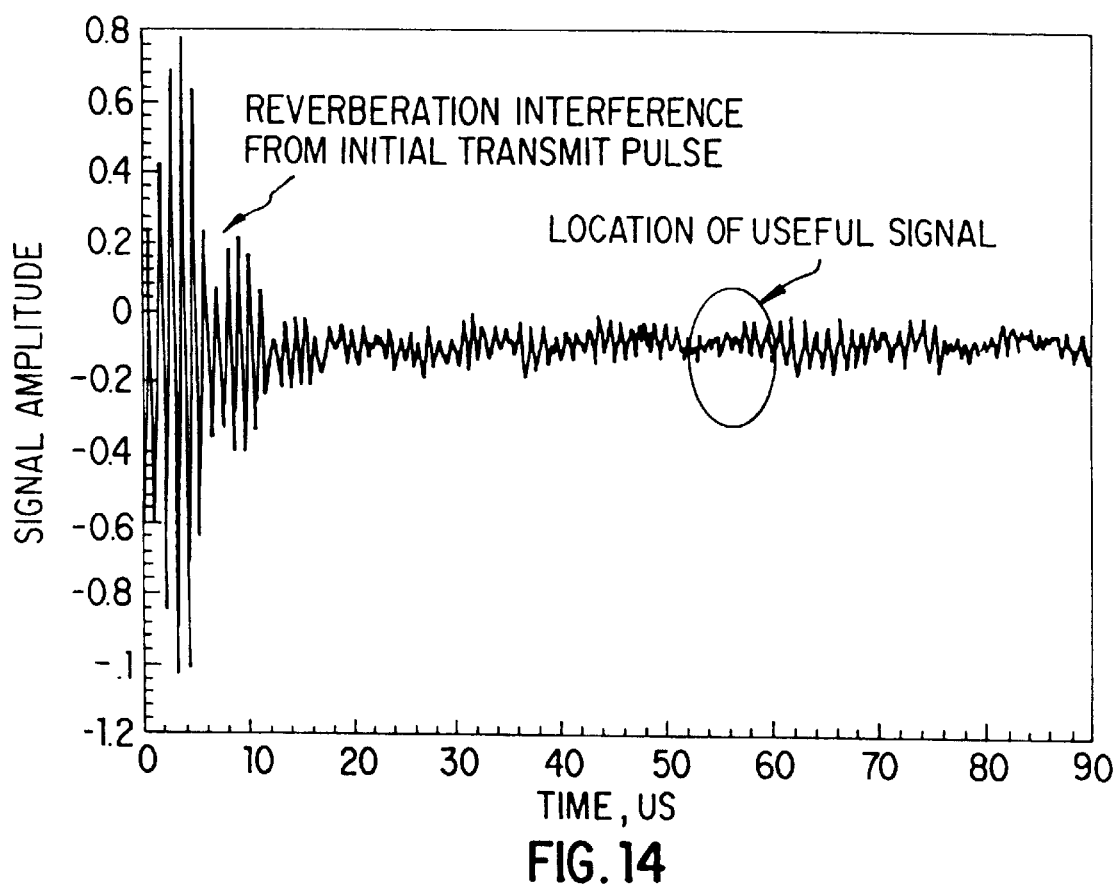
FIG. 14

APPARATUS AND METHODS FOR PERFORMING ACOUSTICAL MEASUREMENTS

CROSS REFERENCE TO RELATED APPLICATIONS

This application is a continuation of co-pending International Application No. PCT/US99/08362 filed on Apr. 16, 1999, which designates the United States, which is a continuation-in-part of U.S. application Ser. No. 09/062,112 filed on Apr. 17, 1998, now U.S. Pat. No. 6,116,080 dated Sep. 12, 2000 the contents of both of which in their entireties are hereby incorporated by reference.

I. FIELD OF THE INVENTION

This invention relates generally to the field of acoustical measurements performed on gases, liquids, and solids. More particularly, in accordance with certain of its aspects, the invention relates to new and improved methods of, and apparatus for, acoustically testing a gas mixture to measure gas concentrations, volumetric flow ratios, and/or mass flow ratios. In accordance with other aspects, the invention relates to the determination and/or the control of the mass (or volume) flow rate of a gas of interest in a carrier gas, where the carrier gas has a known flow rate.

II. BACKGROUND OF THE INVENTION

A. Industrial Setting

Numerous industries employ processes which require accurate delivery of a binary gas mixture consisting of a gas of interest and a carrier gas. To achieve accurate delivery, these industries require precise measurements of the concentration of the gas of interest in the flowing gas mixture, where the gas of interest is typically of high purity and may be highly corrosive. Examples of these processes include: chemical vapor deposition, dopant diffusion in, for example, the semiconductor industry, etching, the operation of high efficiency hydrogen cooled generators, and the like.

Current practice in the above and other industries is to use mass flow controllers upstream of a bubbler (vaporizer) to predict (control) the concentration of the binary gas mixture which is generated in the bubbler. This approach suffers from insufficient accuracy due to, among other things: variations in the bubbler temperature; instability of the temperature and pressure of the binary gas mixture; possible leakages in the gas lines upstream and downstream of the bubbler; and concentration time delays between the mass flow controllers and the points of interest, especially at low flow rates.

In addition, the existing equations used to predict a bubbler's pick-up rate are inaccurate. The following is an example of such an equation, where $G_A$ is the mass pickup rate of gas A (the gas of interest), $Q_B$ is a flow rate of gas B (the carrier gas), P is the pressure of the binary gas mixture, $P_{VA}$ is the vapor pressure of gas A at the bubbler's operating temperature, M is the molecular weight of gas A, T is the temperature of the binary gas mixture, and R is the ideal gas constant:

$$\frac{G_A}{Q_B} = \left(\frac{P_{VA}}{P - P_{VA}}\right)\frac{PM}{RT}.$$

This equation can exhibit an inaccuracy as high as 20% when the bubbler's operating temperature is well below the boiling point of gas A, which is the typical operating condition used in practice.

At present there is a wide variety of concentration sensors on the market which use different measurement approaches, including acoustical (EPISON and MINISON devices sold by Thomas Swan of the United Kingdom), optical (IR-5 device sold by MKS Instruments, Inc., Andover, Mass.), thermal conductivity (Varian Model 3400 Gas Chromatograph, sold by Varian Vacuum Products, Lexington, Mass.), and mass spectroscopy. None of these approaches fulfill all the requirements for a binary gas measuring system, including robustness, maintenance free operation, and the ability to produce highly accurate and repeatable real time concentration measurements of high purity and/or highly corrosive gaseous media.

B. Concentration Sensors Which Employ Acoustical Energy

As discussed above, acoustical measurements have been used in the past in concentration sensors. At their heart, such devices involve a measurement of the speed of sound (or, more accurately, the speed of propagation of acoustical energy) in a medium, with variations in the measured speed being indicative of variations in the concentration of the chemical of interest.

There are two main approaches for measuring the speed of sound in a medium, namely, the phase approach and the pulse approach. The phase approach gives a precise measurement of the phase velocity of acoustical energy in the medium, either by means of a fixed-frequency, variable-path, cylindrical acoustic interferometer or by means of a variable-frequency, fixed-path, spherical acoustic resonator. In accordance with this approach, the speed of sound is assumed to be the same as the phase velocity, which, as discussed below, is not always the case.

The pulse approach provides a direct measurement of wavefront velocity (i.e., speed of sound) and can be implemented either in a shadow format with a separate transmitter and receiver, or an echo format with only one transducer which fulfills both the transmitting and receiving functions (see U.S. Pat. No. 5,325,703). The pulse approach as practiced in the prior art has generally been less accurate than the phase approach.

(1) Phase Approach

Phase methods employ a continuous acoustic wave. The principles of the propagation of sound in finite cylindrical and spherical resonators were worked out by Lord Rayleigh and set forth in his 1877 treatise "The Theory of Sound" (Dover Publ., New York, 1945). From a practical point of view, neither a spherical acoustic resonator nor a cylindrical acoustic interferometer can be used widely for several practical reasons.

For real gases with speeds of sound in the range of 100–1500 meters/second, a spherical resonator requires an efficient broad band acoustic transducer, which does not exist at present. State of the art principles of design of such transducers for liquids are known (see Desilets et al. "The Design of Efficient Broad-Band Piezoelectric Transducers", IEEE Transactions on Sonics and Ultrasonics, Vol. SU-25, No. 3, May 1978, 115–125 and Takeshi Inoue et al. "Design of Ultrasonic Transducers with Multiple Acoustic Matching Layers for Medical Application", IEEE Transaction on Ultrasonics, Ferroelectrics and Frequency Control, Vol. UFFC-34, No. 1, January 1987, 8–16), but their capabilities are very weak for concentration measurements in gaseous media.

A cylindrical acoustic interferometer requires a precision mechanical system with a known distance between a transducer and a moving piston (see Potzick "On the Accuracy of Low Flow Rate Calibrations at the National Bureau of Standards", ISA Transactions, Vol. 25, No. 2, 1986, 19–23). Such a device thus requires continuous maintenance.

In addition to these specific drawbacks, it is important to note that both phase methods use phase velocity as a measure of the speed of sound. Phase velocity and the speed of sound can be different at different frequencies for different gases due to relaxation processes (see Gooberman "Ultrasonics", Hart Publishing Company, Inc., NYC, 1969) and/or shock waves (see Elmore et al. "Physics of Waves", Dover Publications, Inc., NY, 1969). These effects are capable of producing incorrect values for the speed of sound, and, in turn, incorrect concentration measurements.

(2) Pulse Approach

Pulse acoustical concentration measurement methods and instruments for testing binary gases are known. Publications in this area include:

(a) E. Polturak, S. Garrett and S. Lipson, "Precision acoustic gas analyzer for binary mixtures", Rev. Sci. Instrum. 57 (11), American Institute of Physics, November 1986, 2837–2841.

(b) G. Cadet, J. Valdes and J. Mitchell, "Ultrasonic time-of-flight method for on-line quantitation of semiconductor gases", Ultrasonics Symposium, Proceedings, New York, Institute of Electrical and Electronic Engineers, 1991, 295–300.

(c) G. Hallewell and L. Lynnworth, "A simplified formula for the analysis of binary gas containing a low concentration of a heavy vapor in a lighter carrier", Ultrasonics Symposium, Proceedings, New York, Institute of Electrical and Electronic Engineers, 1994, 1311–1316.

(d) J. P. Stagg, "Reagent Concentration Measurements in Metal Organic Vapour Phase Epitaxy (MOVPE) Using an Ultrasonic Cell", Chemtronics, Vol. 3, March 1988, Harlow, Essex, UK, 44–49.

(e) G. Hallewell, G. Crawford, D. McShurley, G. Oxoby and R. Reif, "A Sonar-Based Technique for the Ratiometric Determination of Binary Gas Mixtures", Nuclear Instruments and Methods in Physics Research, A264, 1988, North-Holland, Amsterdam, 219–234.

(f) M. Joos, H. Muller and G. Lindner, "An ultrasonic sensor for the analysis of binary gas mixtures", Sensors and Actuators, B. 15–16, 1993, 413–419.

(g) L. Zipser and F. Wachter, "Acoustic sensor for ternary gas analysis", Sensors and Actuators, B. 26–27, 1995, 195–198.

(h) U.K. Patent GB 2,215,049.

(i) U.S. Pat. Nos. 4,596,133; 4,630,482; 4,850,220; 5,060,507; 5,325,703; 5,351,522; 5,369,979; and 5,392,635.

C. Deficits of Existing Concentration Sensors Which Employ Acoustical Energy None of the prior art acoustical methods perform satisfactory at present. In particular, none of these methods are able to fully meet the fundamental requirements of providing highly accurate concentration measurements without the need for frequent maintenance.

There are a variety of sources of significant error in acoustical concentration measurements. The most important of these are:

(1) Ambiguities in the existing mixing rules used to calculate concentrations from measured values of the speed of sound.

In all of the prior art publications, concentration values are calculated based on the known ideal gas equation for the speed of sound (see, for example, Polturak et al. "Precision acoustic gas analyzer for binary mixtures", Rev. Sci. Instrum. 57 (11), American Institute of Physics, November 1986, 2837–2841 and Cadet et al. "Ultrasonic time-of-flight method for on-line quantitation of semiconductor gases", Ultrasonics Symposium, Proceedings, New York, Institute of Electrical and Electronic Engineers, 1991, 295–300). That is, the calculation of concentration values is ultimately based on the following equation for the speed of sound C in a gas:

$$C = \sqrt{\frac{\gamma RT}{M}} \tag{1}$$

where $$\gamma = \frac{c_p}{c_v} = \frac{c_p}{c_p - R} \tag{2}$$

and where $c_p$ and $c_v$ are the specific heat capacities of the gas at constant pressure and constant volume, respectively, R=8.3144 is the universal gas constant, T is the gas temperature in °K, and M is the gas' molecular weight. As discussed in Reid et al. "The Properties of Gases and Liquids", Fourth Edition, McGraw-Hill, Inc., New York, 1987, $c_p$ can be obtained from the formula:

$$c_p = A_c + B_c T + C_c T^2 + D_c T^3 \tag{3}$$

where the coefficients $A_c$, $B_c$, $C_c$, and $D_c$ are constants whose values depend on the chosen gas.

For a mixture of two gases A and B, equation (1) can be written:

$$C_M = \sqrt{\frac{\gamma_M RT}{M_M}} \tag{4}$$

The challenge in using equation (4) is, of course, determining appropriate values for $\gamma_M$ (the "mixture specific heat ratio") and $M_M$ (the "mixture molecular weight"). Different workers in the art have suggested a variety of mixing rules, which can lead to significantly different values for $M_M$ and $\gamma_M$.

For example, to estimate $M_M$, some publications have proposed simple averaging (see Joos et al. "An ultrasonic sensor for the analysis of binary gas mixtures", Sensors and Actuators, B. 15–16, 1993, 413–419 and Zipser et al. "Acoustic sensor for ternary gas analysis", Sensors and Actuators, B. 26–27, 1995, 195–198):

$$M_M = \sum_i (x_i M_i) \tag{5}$$

where $x_i$ is the volumetric concentration of gas i in the total volume.

On the other hand, more sophisticated mixing rules have been proposed, such as that of Chung et al., "Applications of kinetic gas theories and multiparameter correlation for prediction of dilute gas viscosity and thermal conductivity," Industrial & Engineering Chemistry Fundamentals, 1984, 23:8–13; Reid et al. "The Properties of Gases and Liquids", Fourth Edition, McGraw-Hill, Inc., New York, 1987, 413–414):

$$M_M = \left[ \frac{\sum_i \sum_j x_i x_j \left(\frac{\varepsilon_{ij}}{k}\right) \sigma_{ij}^2 M_{ij}^{1/2}}{\left(\frac{\varepsilon}{k}\right)_M \sigma_M^2} \right]^2 \quad (6)$$

$$\frac{\varepsilon_{ij}}{k} = \frac{T_{ci}}{1.2593}; \frac{\varepsilon_{ij}}{k} = \left(\frac{\varepsilon_{ii}}{k}\frac{\varepsilon_{jj}}{k}\right)^{1/2}; \sigma_{ii} = .809 V_{ci}^{1/3};$$

$$\sigma_{ij} = (\sigma_i \sigma_j)^{1/2}; \sigma_M = \left(\sum_i \sum_j x_i x_j \sigma_{ij}^3\right)^{1/3};$$

$$\left(\frac{\varepsilon}{k}\right)_M = \frac{\sum_i \sum_j x_i x_j \left(\frac{\varepsilon_{ij}}{k}\right) \sigma_{ij}^3}{\sigma_M^3}; M_{ij} = \frac{2 M_i M_j}{M_i + M_j};$$

where $T_{ci}$ and $V_{ci}$ are the critical temperature and critical volume of gas i, respectively.

By substitution of the parameters for a 70:30 hydrogen sulfide/ethyl ether mixture into equations (5) and (6), we obtain $M_M$ values of 46.09 g/mol and 43.738 g/mol, respectively, i.e., a discrepancy of 5.38%. Significantly, the discrepancy between these equations increases for mixtures of gases having higher molecular weight ratios.

Existing mixing rules for calculating $\gamma_M$ values also lead to substantially different results. See Hallewell et al. "A simplified formula for the analysis of binary gas containing a low concentration of a heavy vapor in a lighter carrier", Ultrasonics Symposium, Proceedings, New York, Institute of Electrical and Electronic Engineers, 1994, 1311–1316.

For purposes of comparison with the mixing rule of the present invention, the following formulation of equation (4) will be used since it represents the formulation most commonly used by prior art workers:

$$C_M^* = \left( \frac{RT}{\sum_i x_i M_i} \frac{\sum_i x_i c_{Pi}}{\sum_i x_i c_{Pi} - R} \right)^{1/2} \quad (7)$$

In addition to the discrepancies resulting from different mixing rules, it is also important to note that all prior art methods of acoustical concentration measurement apply to real gases equations which were developed for ideal gases, i.e., they use the ideal gas constant R which implicitly assumes that the compressibility factor of the gas is equal to one. This assumption can cause an error of up to 5% (sometimes even higher) in the speed of sound values obtained from equations (1), (4), or (7). It can also cause errors in the evaluation of the specific heat capacities used in these equations.

For pure gases, this problem can potentially be solved by substitution of R*=zR for R in equations (1) and (2), where z is a compressibility factor. As discussed in Reid et al., supra, at small deviations from ideal gas behavior z can be obtained from the formula:

$$z = 1 + \frac{P_r}{T_r}\left[0.083 - \frac{0.422}{T_r^{1.6}} + \omega\left(0.139 - \frac{0.172}{T_r^{4.2}}\right)\right] \quad (8)$$

where $P_r=P/P_c$ is relative pressure, $T_r=T/T_c$ is relative temperature, P is actual pressure, T is actual temperature, $\omega$ is an "acentric" factor, $T_c$ is the gas' critical temperature, and $P_c$ is its critical pressure, where $\omega$, $T_c$, and $P_c$ are constants for the pure gas. For gases near saturation conditions, Redlich-Kwong, Soave or Peng-Robinson approaches can be used. (See Reid et al., supra, at pages 42–46.)

This problem of compressibility, of course, is much more complicated for a gas mixture since rules for determining the compressibility factor of a gas mixture have not been reported in the literature.

(2) Lack of known thermodynamic properties for many gases.

From equations (1)–(4), we can see that estimation of concentrations requires a priori knowledge of specific heat capacity at both constant pressure and constant volume as a function of temperature.

Coefficients $A_c$, $B_c$, $C_c$, and $D_c$ of equation (3) can be used to calculate $c_p$, and these coefficients have been published for some chemicals. Very often, however, the coefficients have not been published and, indeed, even the manufacturer of the chemical of interest may not have the information needed to estimate the coefficients. For these cases, under the state of the art prior to present invention, it has been impossible to use acoustical methods to measure concentrations.

(3) Insufficient accuracy of existing methods and apparatus for measuring the speed of sound in a gas mixture.

Known acoustic methods and instruments typically employ the shadow acoustic method in which separate transducers are used for transmitting and receiving ultrasonic waves. This approach permits the use of either flexure or radial mode transducers, which have some advantages in comparison to thickness mode transducers, especially for gaseous medium applications. In particular, such transducers have significantly higher electroacoustic efficiency and smaller dimensions (see Folkestad et al. "Chirp Excitation of Ultrasonic Probes and Algorithm for Filtering Transit Times in High-Rangeability Gas Flow Metering", IEEE Transactions on Ultrasonics, Ferroelectrics and Frequency Control, Vol. 40, No. 3, May 1993, 193–215).

The use of separate transducers, however, does have a significant disadvantage which has not been effectively addressed in the prior art. That disadvantage arises from the fact that the acoustic and electronic paths of the transmitted and the received signals are different and thus significant errors can be introduced into the speed of sound determination as a result of:

(a) Spectrum distortion and time delay of the first half-wave of the received signal in the piezoelements, in the transfer layers between the piezoelements and the gaseous medium, and in the electronic networks of the transmitter and receiver. Since these distortions and delays are constant for any given hardware system, this type of systematic error can at least in theory be compensated for during calibration using an ideal or near ideal gas, provided the distance between the two transducers is known to within a few micrometers.

(b) Spectrum distortion of the first half-wave of the received signal as result of operating under far-field conditions as is normally done for systems using the shadow method. That is, the transmitter and the receiver are spaced from one another by an acoustical path length $L_p$ which satisfies the relationship:

$$L_p > \frac{d^2}{4\lambda} - \frac{\lambda}{4} \quad (9)$$

where d is a diameter of the transducer and $\lambda$ is the wavelength of the acoustical energy given by:

$$\lambda = \frac{C}{f} \qquad (10)$$

where is the speed of sound in the testing media and $f$ is the transducer's operating frequency.

Operating in the far-field zone means that an orientation diagram (acoustic field plot) for the transmitter will generally have a spherical shape. More importantly with regard to concentration measurements, operating in the far-field zone means that the orientation diagram will be different for gases with different acoustical properties. As a result, different gas mixtures will produce different distortions of the first half-wave of the received signal, as well as different variations in its duration. Plainly, this type of systematic error is dependent upon the acoustical properties of the gases in the mixture as well as their concentrations, and thus cannot be compensated for during calibration.

(c) Spectrum distortion of the first half-wave of the acoustic signal by the medium which is being tested. The absorption coefficient a of an ideal gas can be estimated from the combined Stokes-Kirchhoffs expression (see Hunter "Acoustics", Englewood Cliffs, N.J., Prentice-Hall, Inc., 1957)

$$\alpha = \frac{2\pi^2 f^2}{\gamma PC}\left(\frac{4}{3}\eta + \frac{\gamma-1}{C_p}k\right) \qquad (11)$$

where $\gamma$ is the gas' specific heat ratio, $\eta$ is its viscosity, $k$ is its thermal conductivity, P is pressure, C is the speed of sound, and $C_p$ is thermal capacitance defined as $c_p/M$ where $c_p$ is the heat capacity at constant pressure and M is molecular weight.

From this equation, it can be seen that gases function as high order low-pass filters, with the characteristics of the filter being dependent on temperature and pressure. The behavior of the filter becomes even more complex for real polyatomic gases, where molecular relaxation effects come into play (see Bhatia, "Ultrasonic Absorption", Dover Publications, Inc., New York, 1985).

As with the far-field effect, the filtering effect depends on the composition and concentrations of the gas mixture, with different mixtures producing different distortions of the first half-wave of the received signal and different changes in its duration. Once again, this type of systematic error cannot be compensated for during calibration.

(d) Spectrum distortion of the first half-wave of the received signal due to side wall reflection interference. This effect occurs during testing of a gas mixture with a low speed of sound. Acoustic chambers are clearly not semi-infinite and thus there are opportunities for the reflection of an acoustic wave having a spherical orientation diagram from the side walls, followed by interference of the reflected wave with the original wave front at the surface of the receiver. This type of systematic error depends upon the acoustical properties of the gas mixture, i.e., the gases making up the mixture and their concentrations.

Of the foregoing four types of systematic error, only the first type is independent of the properties of the gas being tested and can be compensated for during calibration with an ideal or near ideal gas. The other three types of systematic error, which together can achieve several percent, are dependent on the acoustical properties of the gas being tested, and can change significantly with temperature variations. Their reduction is possible only by frequent re-calibration of the instrument with different gases at different concentrations and temperatures, which is clearly undesirable.

D. Summary of the State of the Art

From the foregoing, it can be seen that the existing techniques for performing acoustical measurements suffer from numerous drawbacks and limitations. In particular, all the existing acoustical concentration measurement methods and instruments require frequent maintenance to reduce the total error introduced by different recipes, as well as by temperature and pressure variations. In addition, these techniques are associated with significant inaccuracies and ambiguities in the concentration measurement, which limit their usefulness in producing highly accurate and reliable measurements.

III. SUMMARY OF THE INVENTION

In view of the foregoing, it is an object of the present invention to provide improved methods and apparatus for performing acoustical measurements. More particularly, it is an object of the invention to provide improved methods and apparatus for determining the mass or volume flow rate of a gas of interest in a gas mixture, e.g., a binary mixture. It is also an object of the invention to provide improved methods and apparatus for controlling the flow rate of such a gas of interest.

It is an additional object of the invention to provide improved methods and apparatus for analyzing acoustical measurements performed on a mixture of gases wherein at least one gas in the mixture is compressible.

It is a further object of the invention to provide methods and apparatus for analyzing acoustical measurements performed on a gas whose thermodynamic properties have not been experimentally measured. The acoustical measurements which are to be analyzed may be performed on the gas by itself or when mixed with other gases, where such other gases may or may not have known thermodynamic properties.

It is another object of the invention to provide improved methods and apparatus for performing pulse acoustical measurements on a gas mixture, e.g., a binary gas mixture. As discussed below, one aspect of achieving this object involves measuring the propagation time between two chosen received signals. In this way, the measured acoustic signals have the same electronic and acoustic paths. Advantages which derive from this approach include enhanced repeatability and the absence of drift.

Other aspects of improving pulse acoustical measurement techniques include using high frequencies in the range from 0.5 to 10 MHz which allow for the achievement of high resolution of the received signals, a high sampling rate, and small dimensions of the sensor. In particular, frequencies in this range allow the system to have both a practical sensor size and to operate in the near field zone with plane waves whose divergence coefficient is essentially zero.

Further aspects in the improvement of pulse acoustical measurement techniques include providing an acoustic transducer which includes a piezoelement which: (1) is significantly damped both acoustically and electrically, (2) is operated at its thickness mode frequency, (3) is excited by a high frequency driver, and (4) transfers mechanical vibrations to a test medium through a multilayer acoustical transformer comprising a plurality of impedance matching layers.

The foregoing and other objects are achieved by the following aspects of the invention, which can be used separately or in combination:

A. Operation of the Sensor Under Near-Field Conditions

In accordance with this aspect, the invention provides apparatus for acoustically determining a property of a gas comprising:

(a) a chamber for receiving the gas;
(b) a transmitter which, during use of the apparatus, transmits a pulse of acoustical energy through the gas in the chamber, said transmitter having a characteristic dimension and said pulse of acoustical energy comprising a plurality of oscillations of the acoustical energy, said plurality of oscillations having a center frequency $f_c$; and
(c) a receiver which, during use of the apparatus, detects the pulse after the pulse has passed through the gas in the chamber, said passing of the pulse through the gas defining an acoustical path length $L_p$;

wherein the transmitter has a near field zone of length $L_n$ and the characteristic dimension, the center frequency, and the acoustical path length are chosen so that, during use of the apparatus, the receiver is within said near field zone.

The invention also provides a method for acoustically determining a property of a gas comprising:
(a) generating a pulse of acoustical energy, said generation defining a near-field zone;
(b) passing the pulse through the gas; and
(c) detecting the pulse after its passage through the gas; wherein step (c) is performed while the pulse is within the near-field zone.

The gas can be a pure gas or a mixture of gases, e.g., a binary mixture. In the case of a pure gas, the property which is determined can be the compressibility, heat capacity, molecular weight, temperature, or similar characteristic of the gas. In the case of a gas mixture, the property will typically be the concentration of one or more components of the mixture or a parameter derived from the concentration, e.g., an absolute or relative mass or volume flow, although properties of the type determined for a pure gas can also be determined for a gas mixture if desired.

The length $L_n$ of the near field zone is determined from the following equation:

$$L_n = \frac{d^2}{4\lambda} - \frac{\lambda}{4}$$

where d is the characteristic dimension of the transmitter (e.g., the diameter of the transmitter's piezoelement in the case of a circular element or the element's minor dimension in the case of a rectangular element), and $\lambda$ is the wavelength of the acoustical energy which is given by:

$$\lambda = \frac{C}{f_c}$$

where C is the speed of sound for the gas whose property is to be determined.

Preferably, $f_c$ and $L_p$ satisfy the following relationships:
$0.5$ megahertz $\leq f_c \leq 10$ megahertz; and/or
$L_p \leq 0.5 \, L_n$.

Passage of the pulse through the gas will generally comprise movement of the pulse in alternating directions between first and second spaced apart points within the chamber, e.g., a first point at the gas-contacting surface of the transmitter and a second point at the gas-contacting surface of the receiver such that a line between the points is perpendicular to the gas-contacting surfaces.

In certain embodiments, the transmitter comprises a first transducer located in the vicinity of the first spaced apart point and the receiver comprises a second transducer located in the vicinity of the second spaced apart point, wherein each of the first and second transducers is operated in its thickness mode.

In connection with these embodiments, the transmitter preferably comprises a high frequency driver and an electrical matching circuit which electrically connects the high frequency driver to the first transducer, said electrical matching circuit serving to efficiently couple the output of the high frequency driver to the electrical impedance of the transducer associated with the transducer's thickness mode, inefficiently couple said output to the electrical impedance of the transducer associated with its radial mode, and electrically damp electrical signals produced by mechanical oscillations of the first transducer after the first transducer has transmitted a pulse. This aspect of the invention can be used irrespective of whether the acoustical path length $L_p$ is greater or less than $L_n$. It also can be used with both gases and liquids.

The receiver preferably comprises a current-to-voltage converter electrically connected to the second transducer, an electrical matching circuit electrically connected to the current-to-voltage converter, and an amplifier electrically connected to the electrical matching circuit wherein the current-to-voltage converter has (i) a low input and output resistance and (ii) an output electrical impedance which is in resonance with the electrical matching circuit when the second transducer undergoes thickness mode vibrations. Again, this aspect of the invention can be used irrespective of whether the acoustical path length $L_p$ is greater or less than $L_n$, and can be used for gases and liquids.

In other embodiments, the transmitter and receiver comprise a common transducer, operated in its thickness mode, which is located in the vicinity of the first spaced apart point and the apparatus comprises a reflecting surface at the second spaced apart point.

In connection with these embodiments, the transmitter preferably comprises a high frequency driver and an electrical matching circuit which electrically connects the high frequency driver to the common transducer, said electrical matching circuit serving to efficiently couple the output of the high frequency driver to the electrical impedance of the common transducer associated with the transducer's thickness mode, inefficiently couple said output to the electrical impedance of the common transducer associated with its radial mode, and electrically damp electrical signals produced by mechanical oscillations of the common transducer after the transducer has transmitted a pulse. This aspect of the invention can be used irrespective of whether the acoustical path length $L_p$ is greater or less than $L_n$. It also can be used with both gases and liquids.

For this embodiment, the receiver preferably comprises a current-to-voltage converter electrically connected to the common transducer, an electrical matching circuit electrically connected to the current-to-voltage converter, and an amplifier electrically connected to the electrical matching circuit wherein the current-to-voltage converter has (i) a low input and output resistance and (ii) an output electrical impedance which is in resonance with the electrical matching circuit when the common transducer undergoes thickness mode vibrations. Again, this aspect of the invention can be used irrespective of whether the acoustical path length $L_p$ is greater or less than $L_n$, and can be used for gases and liquids.

Whether one or two transducers are used, each transducer is preferably coupled to the gas by a multilayer acoustical transformer which serves to match the acoustical impedance of the transducer to the acoustical impedance of the gas. The transformer can, for example, comprise an inner aluminum layer which contacts the transducer and an outer PVDF layer which contacts the test medium. Alternatively, a metal layer can be sandwiched between an aluminum layer which contacts the transducer and a tetrafluoroethylene layer which contacts the test medium. Similarly, whether one or two transducers are used, a mechanical damper is preferably associated with each transducer. These aspects of the invention can be used irrespective of whether the acoustical path length $L_p$ is greater or less than $L_n$.

In further embodiments, the property of the gas is determined as the gas flows through the chamber, e.g., in a direction which is substantially perpendicular to a line between the first and second spaced apart points. In connection with these embodiments, flow control means are preferably employed to provide a substantially uniform flow of the gas in the region of the chamber between the first and second spaced apart points. In addition to regulating the flow of gas, the flow control means preferably also regulates the gas' temperature.

B. Determination of the Time Difference Between Two Detections of an Acoustical Pulse at a Receiver In accordance with this aspect, the invention provides apparatus for. acoustically determining a property of a gas, liquid, or solid comprising:

(a) a transmitter which, during use of the apparatus, produces a pulse of acoustical energy which moves in alternating directions between first and second spaced apart points in the gas, liquid, or solid;

(b) a receiver which, during use of the apparatus, detects the pulse; and (c) detecting means associated with the receiver for detecting the pulse after the pulse has made n passages between the first and second spaced apart points (the n-passage pulse) and after it has made m passages between those points (the m-passage pulse), where a passage constitutes movement of the pulse between the first and second spaced apart points in either direction, m and n are integers, and $$m-n=2i$$

where i is an integer.

The invention also provides a method for acoustically determining a property of a gas, liquid, or solid comprising:

(a) producing a pulse of acoustical energy which moves in alternating directions between first and second spaced apart points in the gas, solid, or liquid; and (b) detecting the pulse after it has made n passages between the first and second spaced apart points (the n-passage pulse) and after it has made m passages between those points (the m-passage pulse), where a passage constitutes movement of the pulse between the first and second spaced apart points in either direction, m and n are integers, and $$m-n=2i$$

where i is an integer.

As with the aspects of the invention relating to operating in the nearfield zone, the property of the gas, liquid, or solid which is determined from the time difference between two detections of an acoustical pulse at a receiver can be essentially any physical or chemical property which is responsive to acoustical energy.

Preferably, the detecting means comprises assigning means for assigning a time $t_n$ to the n-passage pulse and a time $t_m$ to the m-passage pulse. The assigned time can comprise a sample number for a digitized signal, as opposed to an actual time in, for example, seconds. Such assigning means can, for example, comprise:

(i) equaling means for substantially equal the amplitudes of the n-passage and m-passage pulses; and (ii) identifying means for identifying reference points for the amplitude equalized n-passage and m-passage pulses. The equalizing means and the identifying means can preferably have following properties:

(i) the equalizing means produces an n-passage pulse whose maximum amplitude is $U_n$ and a m-passage pulse whose maximum amplitude is $U_m$, where $U_n$ substantially equals $U_m$;

(ii) the identifying means comprises means for producing rectified envelopes of the amplitude equalized pulses; and (iii) the reference points for the amplitude equalized n-passage and m-passage pulses comprise those points where the rectified envelopes of those pulses have amplitudes of $kU_n$ and $kU_m$, respectively, where $$0<k<1.$$

A preferred value for k is 0.5.

C. Cross-Correlation Technique for Detecting an Acoustical Pulse

In accordance with this aspect, the invention provides apparatus for use with (i) a transmitter which produces a pulse of acoustical energy (the "original pulse") which passes through a gas, liquid, or solid, and (ii) a receiver which detects the pulse after its passage through the gas, liquid, or solid (the "detected pulse"), said apparatus comprising:

(a) cross-correlating means associated with the receiver for performing a cross-correlation between a waveform representing the original pulse and the detected pulse, said cross-correlating means producing a cross-correlation function for the detected pulse; and (b) peak determining means for determining the peak of said cross-correlation function, said peak being indicative of the time the detected pulse was detected by the receiver.

The invention also provides a method for testing a gas, liquid, or solid comprising:

(a) producing a pulse of acoustical energy which passes through the gas, solid, or liquid (the "original pulse");

(b) detecting the pulse after it has passed through the gas, solid, or liquid (the "detected pulse");

(c) performing a cross-correlation between a waveform representing the original pulse and the detected pulse, said cross-correlation producing a cross-correlation function for the detected pulse; and (d) determining the peak of said cross-correlation function, said peak being indicative of the time the detected pulse was detected in step (b).

The cross-correlation techniques of this aspect of the invention, including the preferred embodiments thereof discussed below, can be used. to perform the assigning function for the n-passage and m-passage pulses discussed above.

The waveform representing the original pulse is preferably determined using a gas which has: (i) a known specific heat, compressibility, and molecular weight, or, equivalently, a known speed of sound; and (ii) a close to ideal gas behavior at the center frequency of the acoustical oscillations making up the original pulse. Preferably, that waveform is obtained by averaging a large number of detected and stored pulses.

In certain preferred embodiments, the cross-correlation is performed by:

(i) performing a fast Fourier transform of the detected pulse to produce a Fourier transformed detected pulse;

(ii) multiplying the Fourier transformed detected pulse by the complex conjugate of a Fourier transform of the waveform representing the original pulse (the "template waveform") to produce a Fourier space cross-correlation function; and (iii) performing an inverse fast Fourier transform of said Fourier space cross-correlation function determined in step (ii) and taking the real part of said inverse fast Fourier transform to produce said cross-correlation function.

The foregoing three steps and apparatus for performing those steps can be used generally whenever a cross-correlation between a template (e.g., the waveform representing the original pulse) and a signal (e.g., the detected pulse) is desired.

In other preferred embodiments, the peak of the cross-correlation function is determined by:

(i) identifying the largest amplitude of the cross-correlation function and two amplitudes adjacent to the largest amplitude;

(ii) fitting a second order polynomial to said three amplitudes; and (iii) determining the peak of the cross-correlation function from said second order polynomial.

In still further preferred embodiments, the original pulse is:

(i) windowed whereby the leading and trailing cycles of the pulse taper from zero to full amplitude; and/or (ii) frequency modulated.

D. Determination of the Speed of Sound for a Gas Whose Thermodynamic Properties Have Not Been Experimentally Determined In accordance with this aspect, the invention provides apparatus for acoustically determining a property of a gas, said gas comprising a molecular species which has $n_a$ atoms per molecule, said molecule having a molecular mass $m_m$, said apparatus comprising:

(a) a transmitter which, during use of the apparatus, produces acoustical energy which passes through the gas;

(b) a receiver which, during use of the apparatus, detects the acoustical energy; and (c) computing means for determining the property of the gas based on the equations:

$$n_f = 6(n_a - 1); \text{ and}$$
$$C = ((2 + n_f)(kT)/(n_f m_m))^{1/2}$$

where C is the speed of sound in the gas, T is the temperature of the gas, and k is Boltzmann's constant.

The invention also provides a method for determining a property of such a gas comprising:

(a) producing acoustical energy which passes through the gas;

(b) detecting the acoustical energy after it has passed through the gas; and (c) determining the property of the gas based on the above equations.

E. Determination of the Speed of Sound for a Compressible Gas Mixture

In accordance with this aspect, the invention provides apparatus for acoustically determining a property of a gas, said gas comprising a mixture of at least two molecular species, said apparatus comprising:

(a) a transmitter which, during use of the apparatus, produces acoustical energy which passes through the gas;

(b) a receiver which, during use of the apparatus, detects the acoustical energy; and (c) computing means for determining the property of the gas based on the equation:

$$C_M = \left( \frac{RT}{\sum_i x_i \frac{M_i}{z_i}} \times \frac{\sum_i x_i c_{Pi}}{\sum_i x_i (c_{Pi} - z_i R)} \right)^{1/2}$$

where $C_M$ is the speed of sound in the mixture, T is the temperature of the mixture, R is the universal gas constant, and $x_i$, $c_{pi}$, $M_i$, and $z_i$ are the volumetric concentration, specific heat, molecular weight, and compressibility factor, respectively, of the $i^{th}$ molecular species.

The invention also provides a method for determining a property of such a gas comprising:

(a) producing acoustical energy which passes through the gas;

(b) detecting the acoustical energy after it has passed through the gas; and (c) determining the property of the gas based on the above equation.

F. Calibration of an Acoustical Sensor by Determining the Time Difference Between Two Detections of an Acoustical Pulse at the Sensor's Receiver In accordance with this aspect, the invention provides a method for calibrating an acoustical sensor which comprises a test chamber, said method comprising:

(a) introducing a gas, solid, or liquid into the test chamber, said gas, solid, or liquid having a known speed of sound $C_N$;

(b) producing a pulse of acoustical energy which moves in alternating directions between first and second spaced apart points in the gas, solid, or liquid;

(c) detecting the pulse after it has made n passages between the first and second spaced apart points (the n-passage pulse) and after it has made m passages between those points (the m-passage pulse), where a passage constitutes movement of the pulse between the first and second spaced apart points in either direction, m and n are integers, and $$m - n = 2i$$

where i is an integer; and (c) determining the distance L between the first and second spaced apart points from the equation:

$$L = \frac{C_N \times (t_2 - t_1)}{2i}$$

where $t_2$ and $t_1$ are the detection times of the m-passage and n-passage pulses, respectively.

As discussed above, $t_2$ and $t_1$ need not be actual times, but can be sample numbers. In particular, when the cross-correlation techniques discussed above are used, the difference in sample numbers for the peaks of the correlograms for the m-passage and n-passage pulses can be directly used as a time difference measurement. In addition to being used during calibration, such sample numbers for the peaks of the correlograms can also be used when a medium is being acoustically tested.

For an acoustical sensor which has a transmitter at the first spaced apart point and a receiver at the second spaced apart point and for m=3 and n=1, the sum of the time delays in the transmitter and the receiver can be calculated from $t_2$ and $t_1$ in accordance with the following equation:

$$\tau = t_{trans} = t_{rcve} = \frac{3t_1 - t_2}{2}$$

where $t_{trans}$ is the delay in the transmitter, $t_{rcve}$ is the delay in the receiver, and $\tau$ is the overall delay. Tau can be used to determine the speed of sound for a test gas, liquid, or solid ($C_{test}$) from the one-passage pulse in accordance with the following equation:

$$C_{test} = \frac{L}{(t_1 - \tau)}$$

where $t_1$ is the detection time of the one-passage pulse.

G. Calibration of an Acoustical Sensor To Determine the Stray Path Signal

In accordance with this aspect, the invention provides a method for calibrating an acoustical sensor which comprises a transmitter, a receiver, and a test chamber, said method comprising:

(a) evacuating the test chamber;

(b) activating the transmitter to produce a pulse of acoustical energy and recording the resulting signal at the receiver;

(c) repeating step (b) to produce a plurality of recorded signals; and (d) averaging the plurality of recorded signals to produce a stray path signal.

Once obtained, the stray path signal is subtracted from the signal recorded during use of the sensor when the test chamber contains the gas, liquid, or solid which is to be acoustically tested. The subtraction is performed before the signal is analyzed, e.g., before the signal is analyzed by the cross-correlation techniques discussed above.

H. Feedback Control of a Gas of Interest by Controlling The Flow of a Carrier Gas In accordance with this aspect, the invention provides apparatus for controlling the composition of a mixture of a gas of interest and a carrier gas, said apparatus comprising:

(a) carrier gas flow control means (e.g., a mass flow controller) for controlling the flow of the carrier gas;

(b) mixing means (e.g., a bubbler) for producing the mixture of tie gas of interest and the carrier gas;

(c) determining means for determining a property of the mixture, said property being indicative of the composition of the mixture (e.g., the property can be the mass flow of the gas of interest provided by the mixture); and (d) control means operatively connected to the carrier gas flow control means and the determining means for controlling the carrier gas flow control means based on a difference between the property of the mixture determined by the determining means and a desired value for that property.

The invention also provides a method for controlling the composition of a mixture of a gas of interest and a carrier gas, said method comprising:

(a) determining a property of the mixture (e.g., the mass flow of the gas of interest provided by the mixture); and (b) controlling the flow of the carrier gas by determining the difference between the property of the mixture determined in step (a) and a desired value for that property.

The accompanying drawings, which are incorporated in and constitute part of the specification, illustrate the various aspects (preferred embodiments) of the invention, and together with the description, serve to explain the principles of the invention. It is to be understood, of course, that both the drawings and the description are explanatory only and are not restrictive of the invention.

IV. BRIEF DESCRIPTION OF THE INVENTION

FIG. 1 is an acoustic cell timing diagram illustrating certain features of the invention.

FIG. 2 is a block diagram of various hardware elements which can be used to implement the analog signal processing aspects of the invention. This block diagram is for an acoustic sensor which employs a single transducer which serves as a component of both an acoustical pulse transmitter and an acoustical pulse receiver.

FIG. 3 is a cross-sectional schematic view of a first embodiment of an acoustical sensor employing a single transducer.

FIGS. 4 and 5 are cross-sectional views of a second embodiment of an acoustical sensor employing a single transducer.

FIG. 7 is a cross-sectional schematic view of a first embodiment of an acoustical sensor employing two transducers.

FIGS. 8 and 9 are cross-sectional views of a second embodiment of an acoustical sensor employing two transducers.

FIG. 12 shows typical voltage waveforms at locations A through K of FIGS. 2 and 6.

FIG. 13 is a graph showing the increase in acoustical attenuation at 1 MHz due to molecular relaxation for a mixture of hydrogen and carbon dioxide at one atmosphere. The vertical axis is plotted in attenuation units relative to ideal gas with attenuation normalized to one.

FIG. 14 shows a received signal for a hydrogen/carbon dioxide mixture having a concentration which corresponds to the molecular relaxation peak of FIG. 13.

Figure 16A:
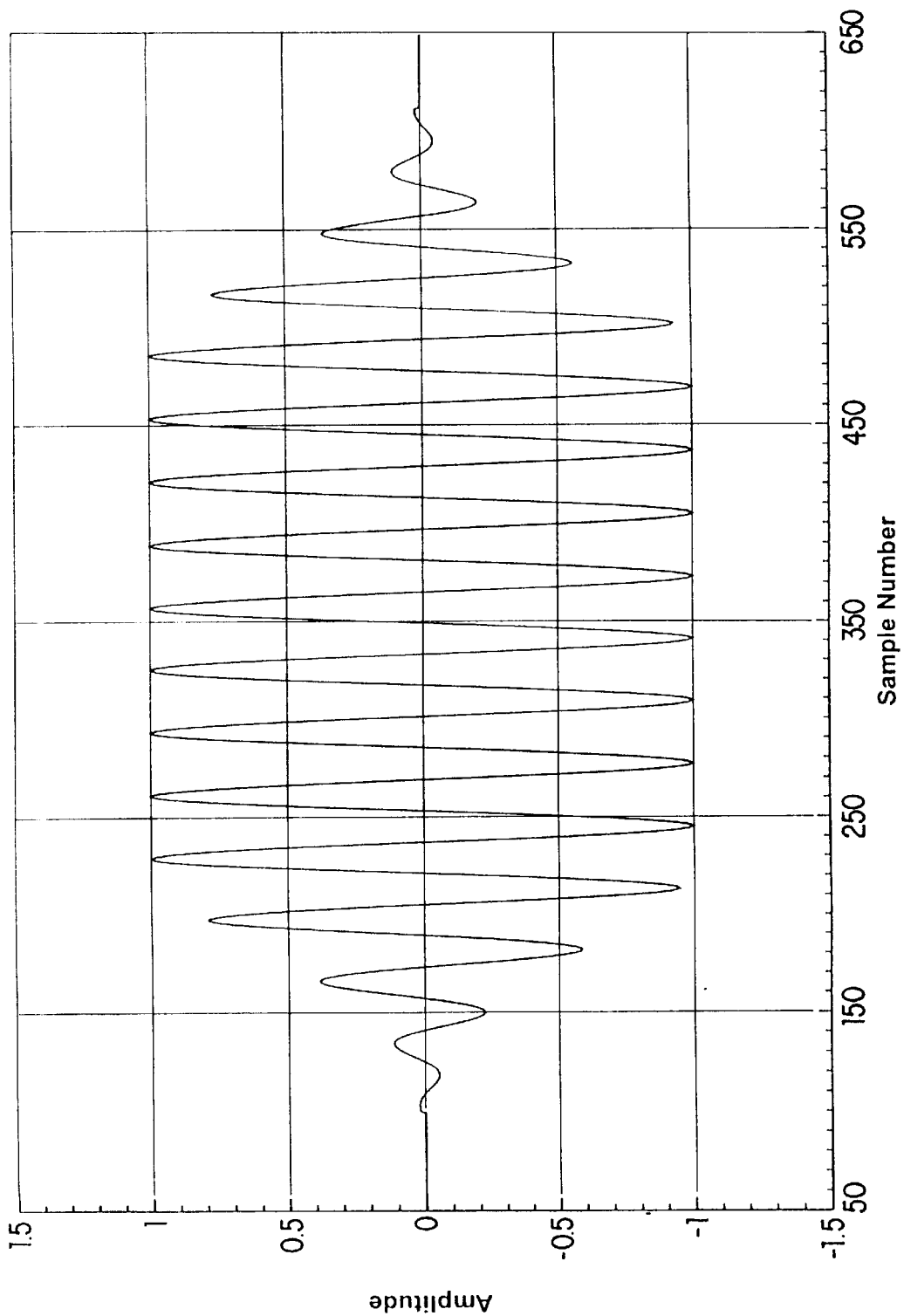
Figure 16B:
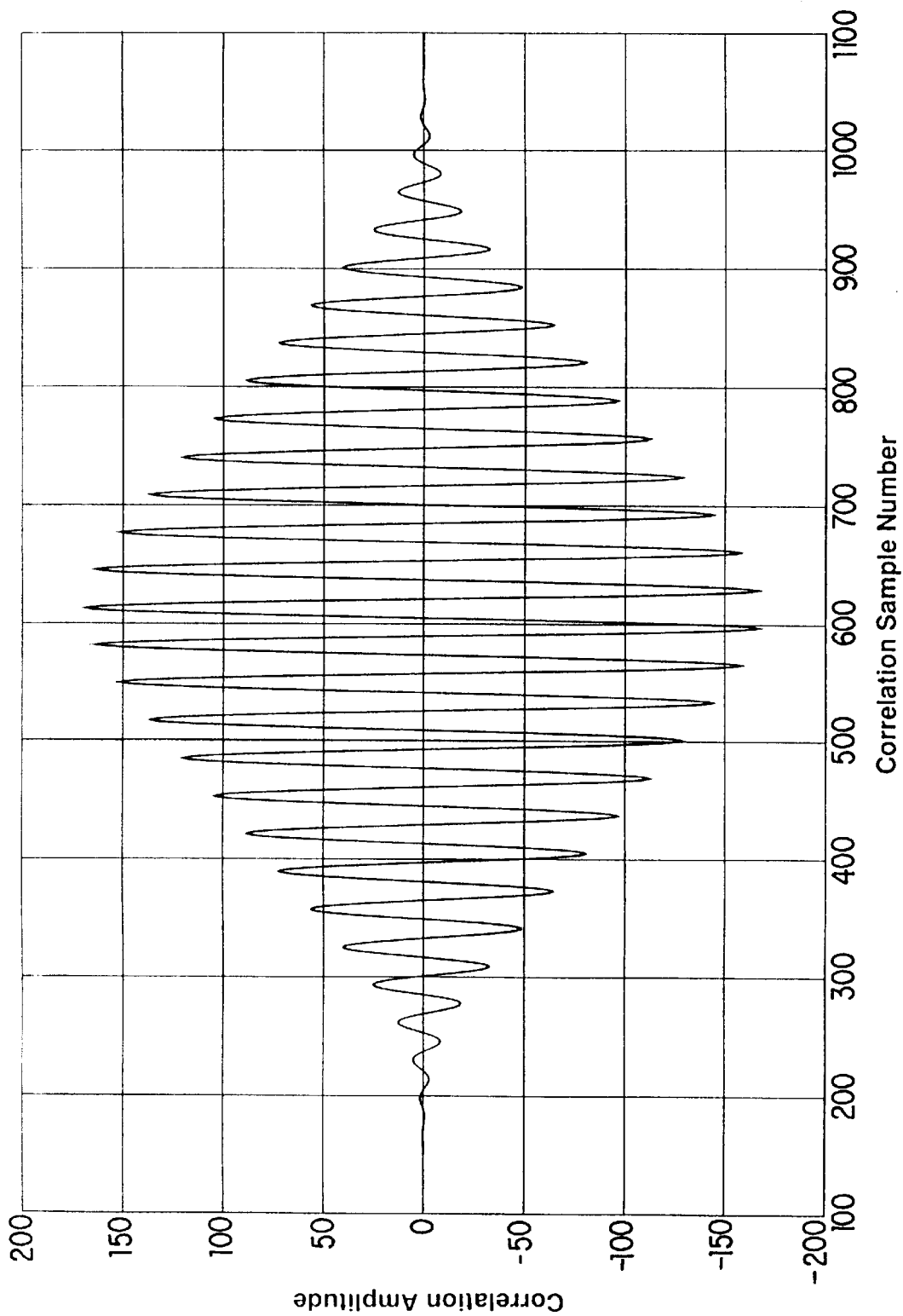
Figure 16C:
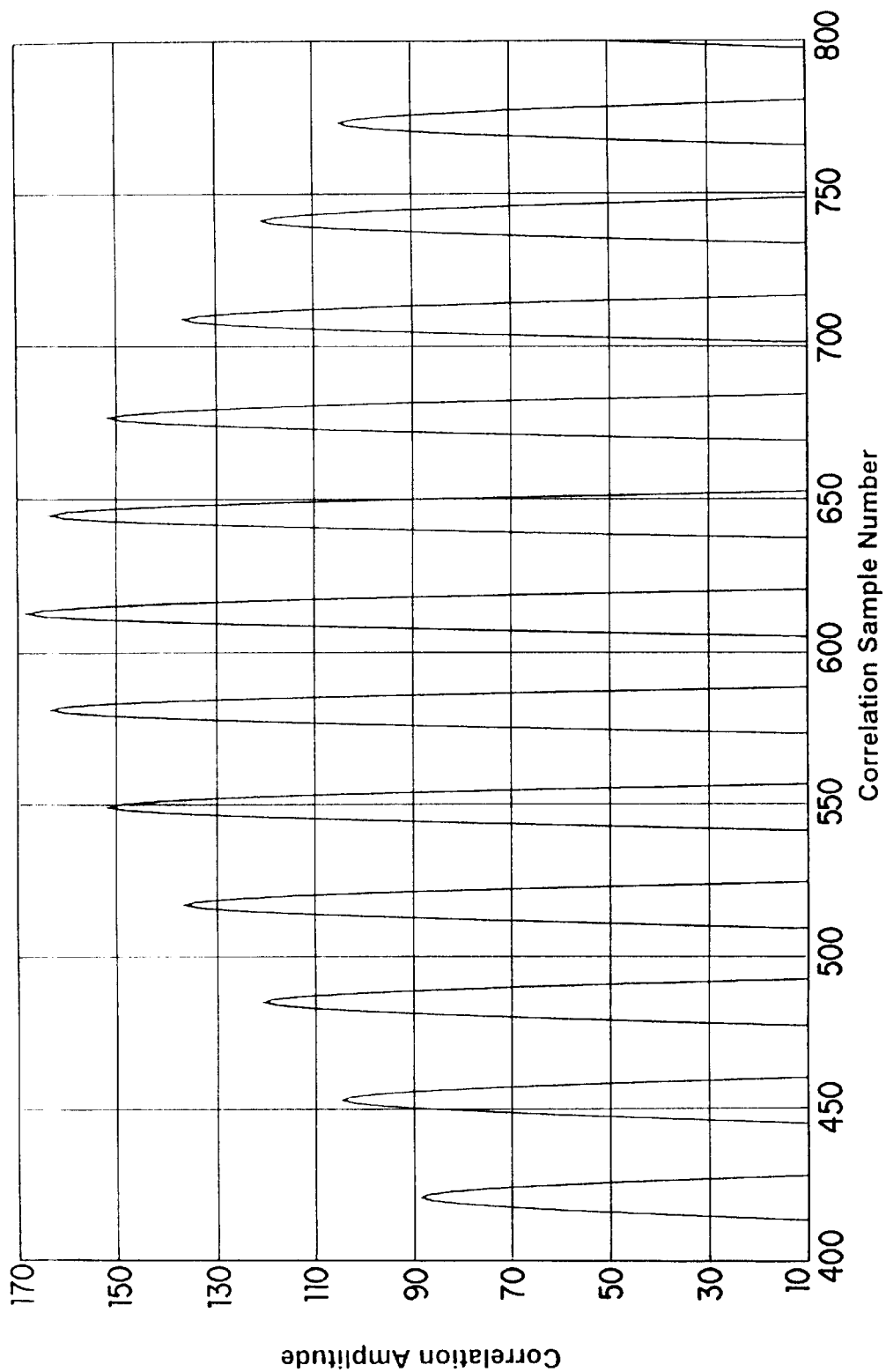

FIG. 16A is a plot of a noise-free, windowed, 16 cycle signal with no frequency modulation; FIG. 16B is a plot of the cross-correlation function for the signal of FIG. 16A and has a central correlation peak at sample number 613; FIG. 16C is an expanded view of the correlation function around the central correlation peak of FIG. 16B.

Figure 17A:
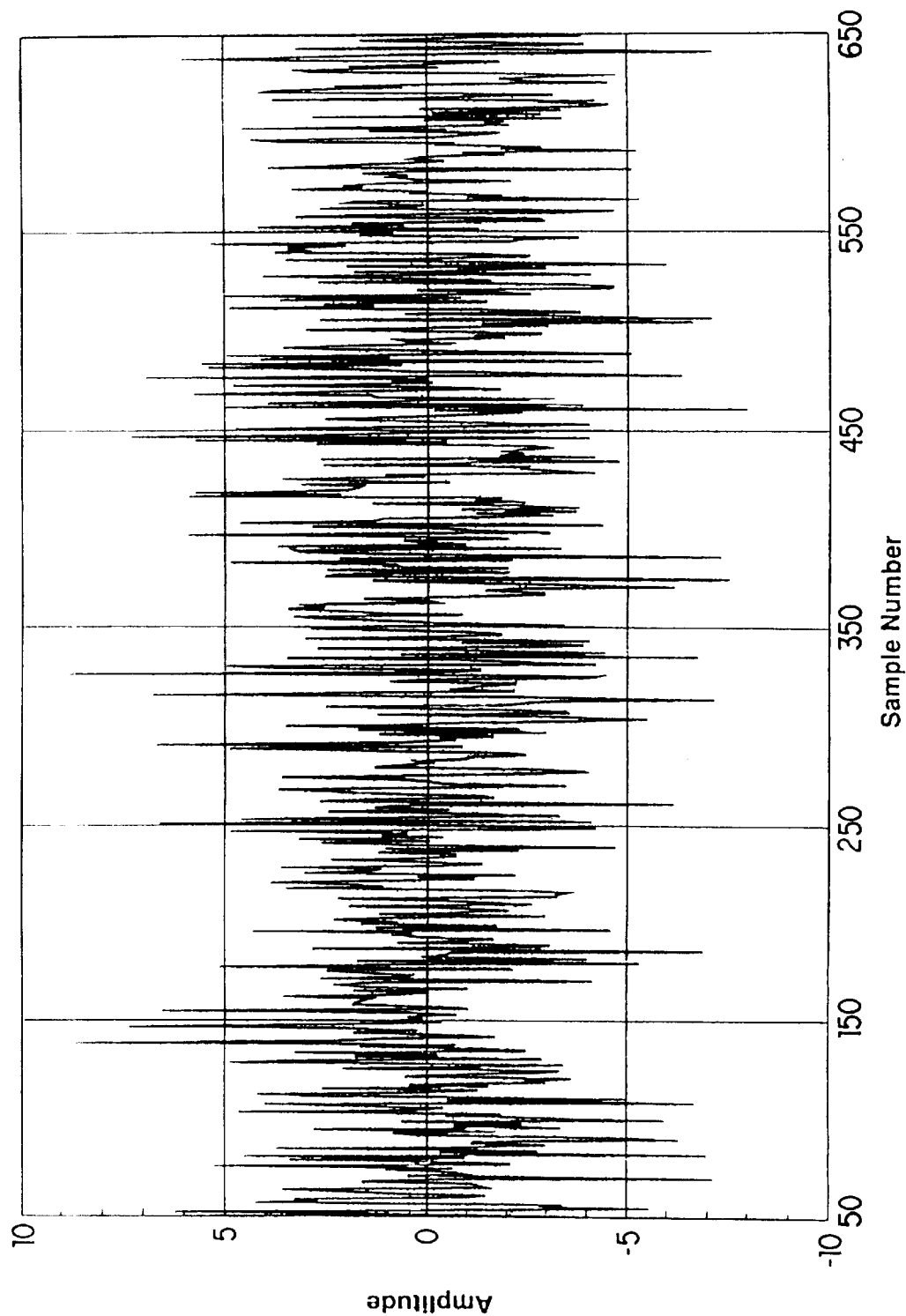
Figure 17B:
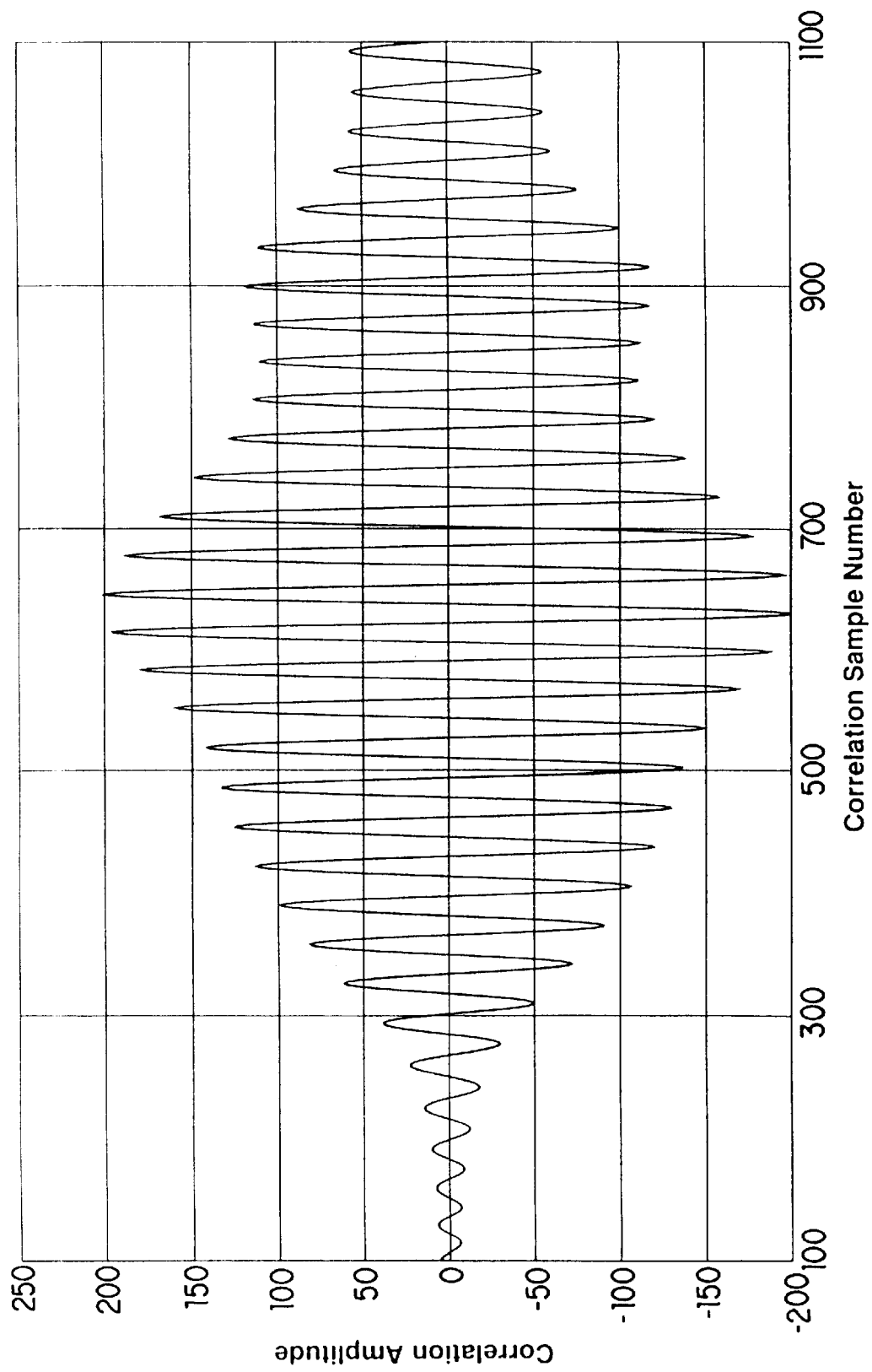
Figure 17C:
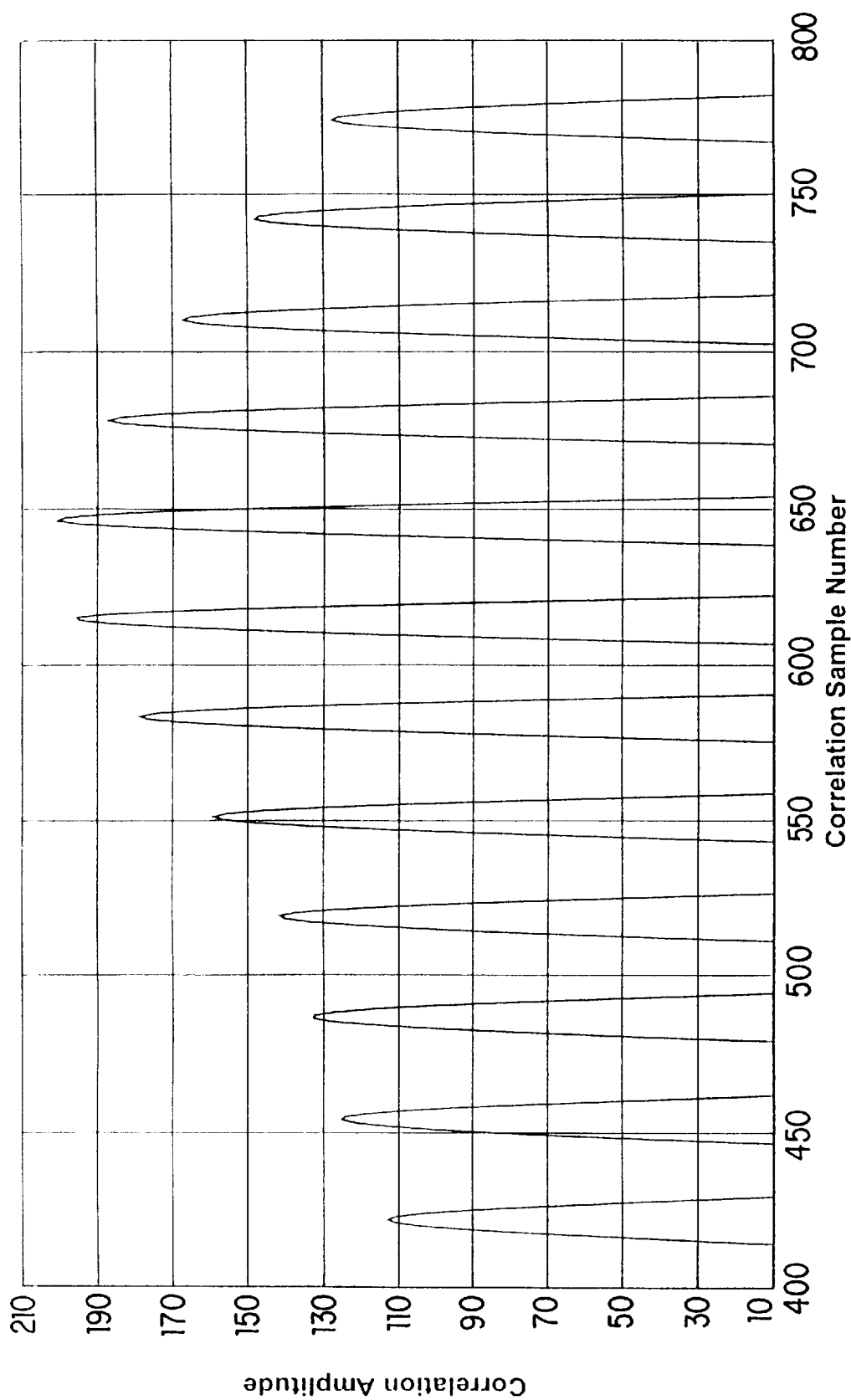

FIG. 17A is a plot of the signal of FIG. 16A with noise added;

FIG. 17B is a plot of the cross-correlation function for the signal of FIG. 17A which has a maximum amplitude correlation peak to the right of sample number 613; FIG. 17C is an expanded view of the correlation function around the maximum amplitude correlation peak of FIG. 17B.

Figure 18A:
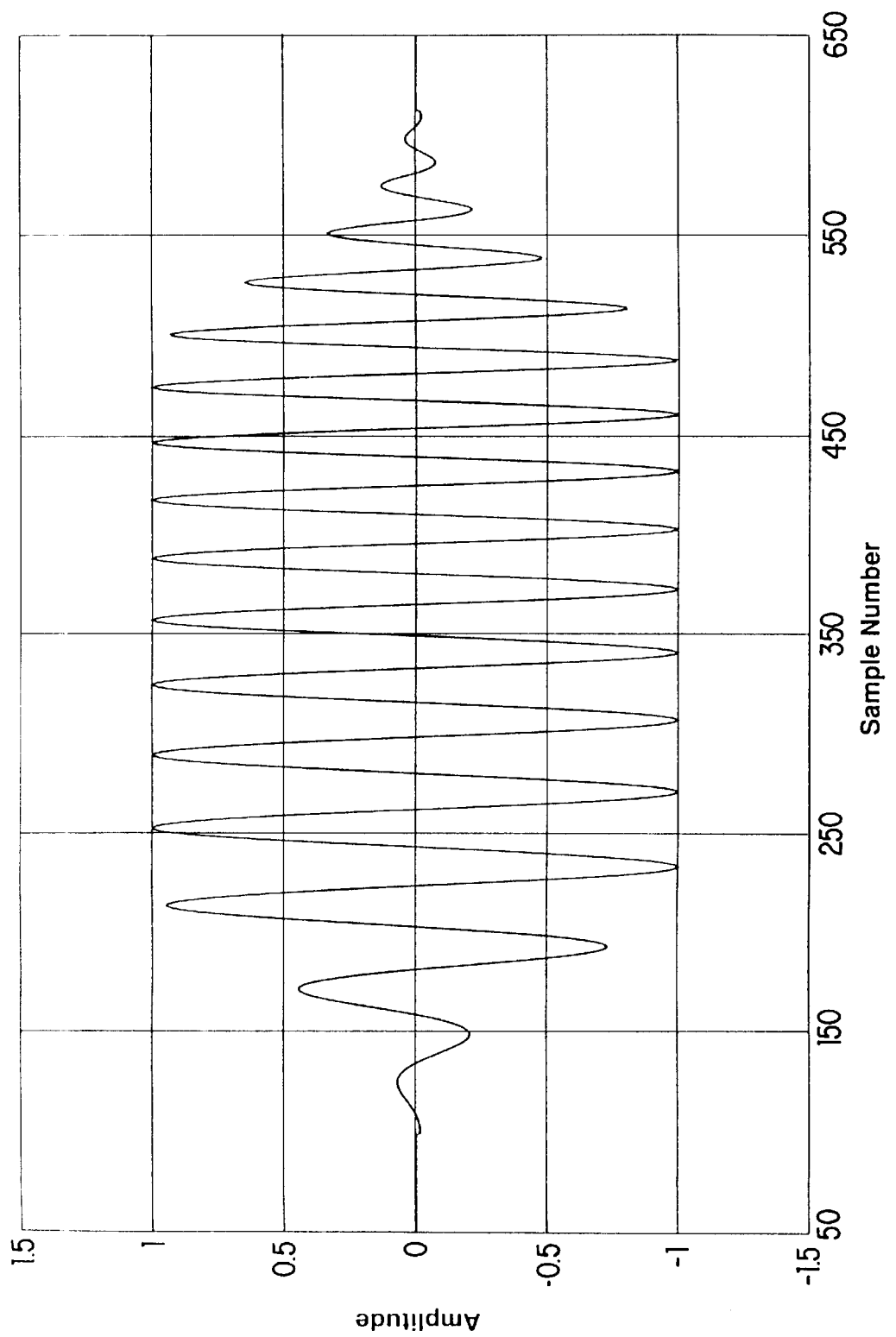
Figure 18B:
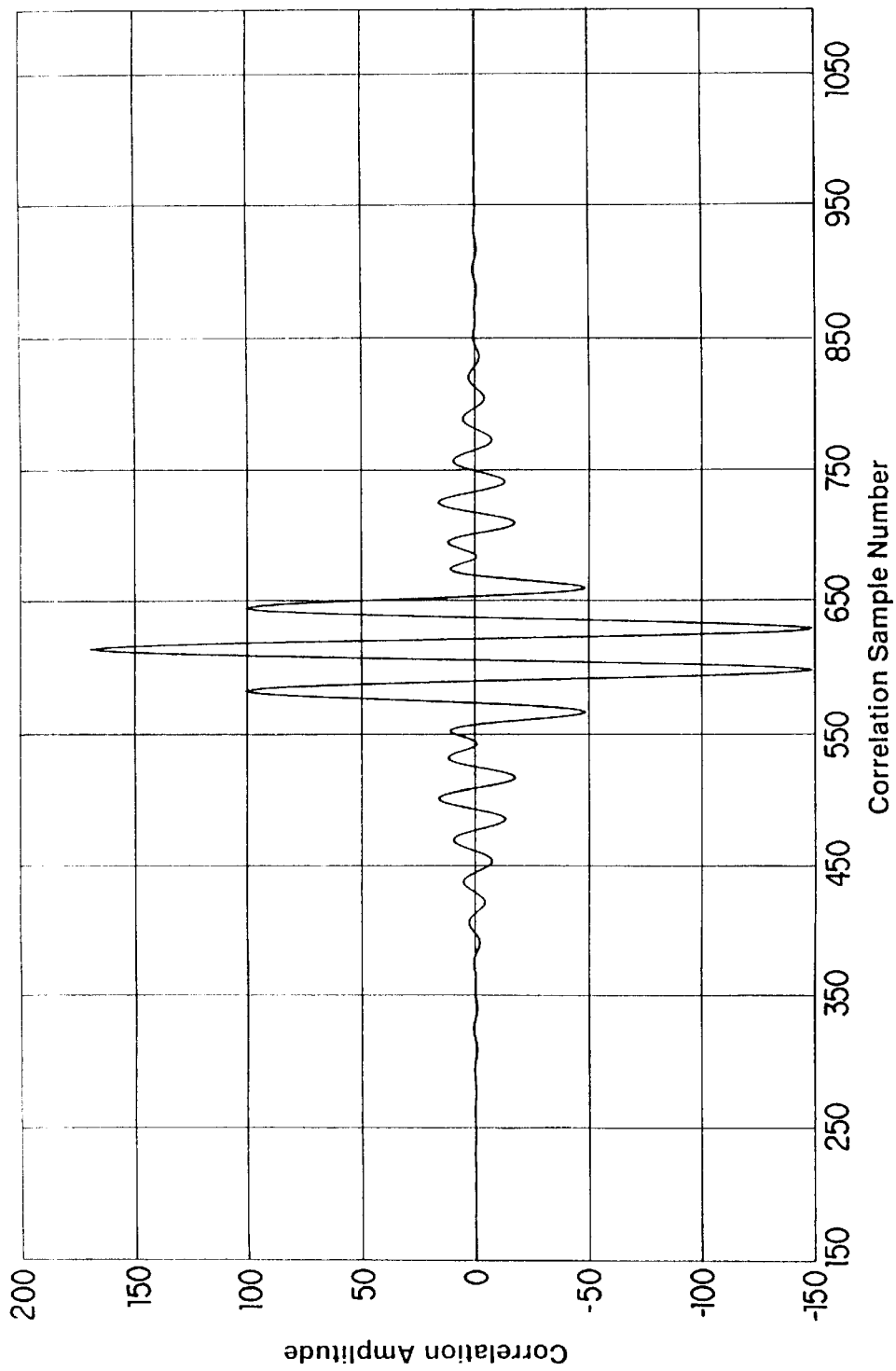
Figure 18C:
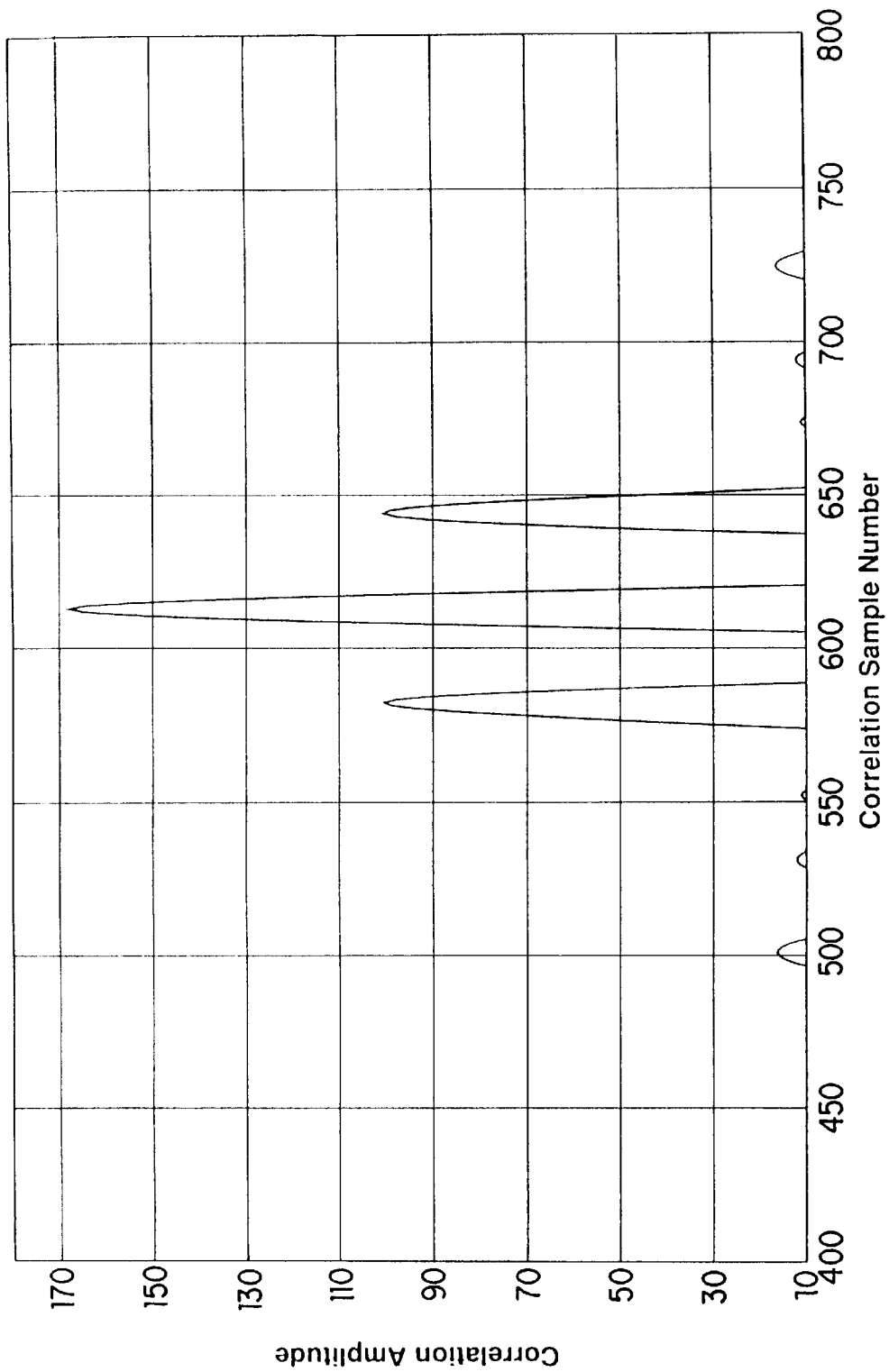

FIG. 18A is a plot of a noise-free, windowed, 16 cycle signal with frequency modulation; FIG. 18B is a plot of the cross-correlation function for the signal of FIG. 18A which has a central correlation peak at sample number 613; FIG. 18C is an expanded view of the correlation function around the central correlation peak of FIG. 18B.

Figure 19A:
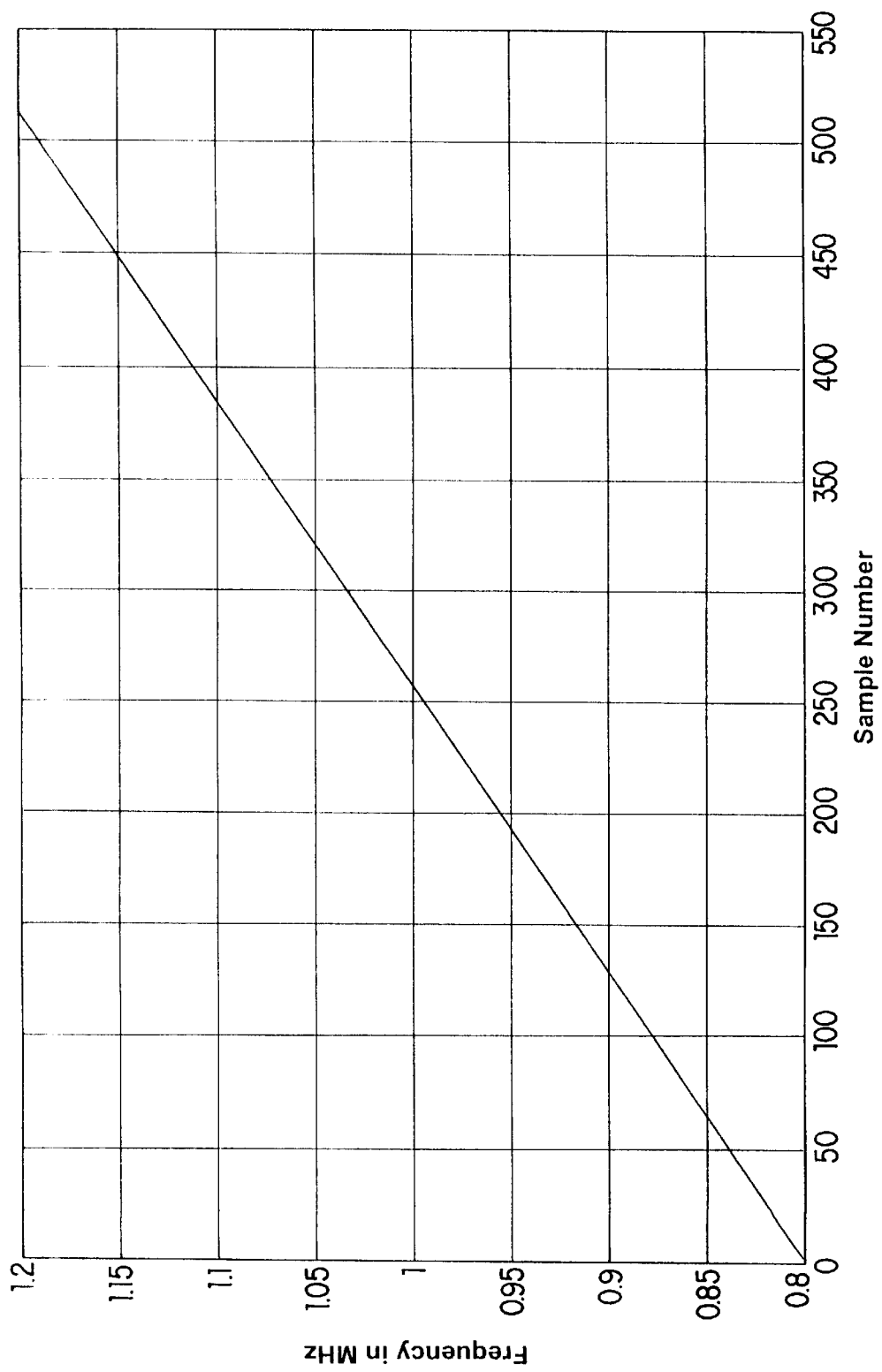
Figure 19B:
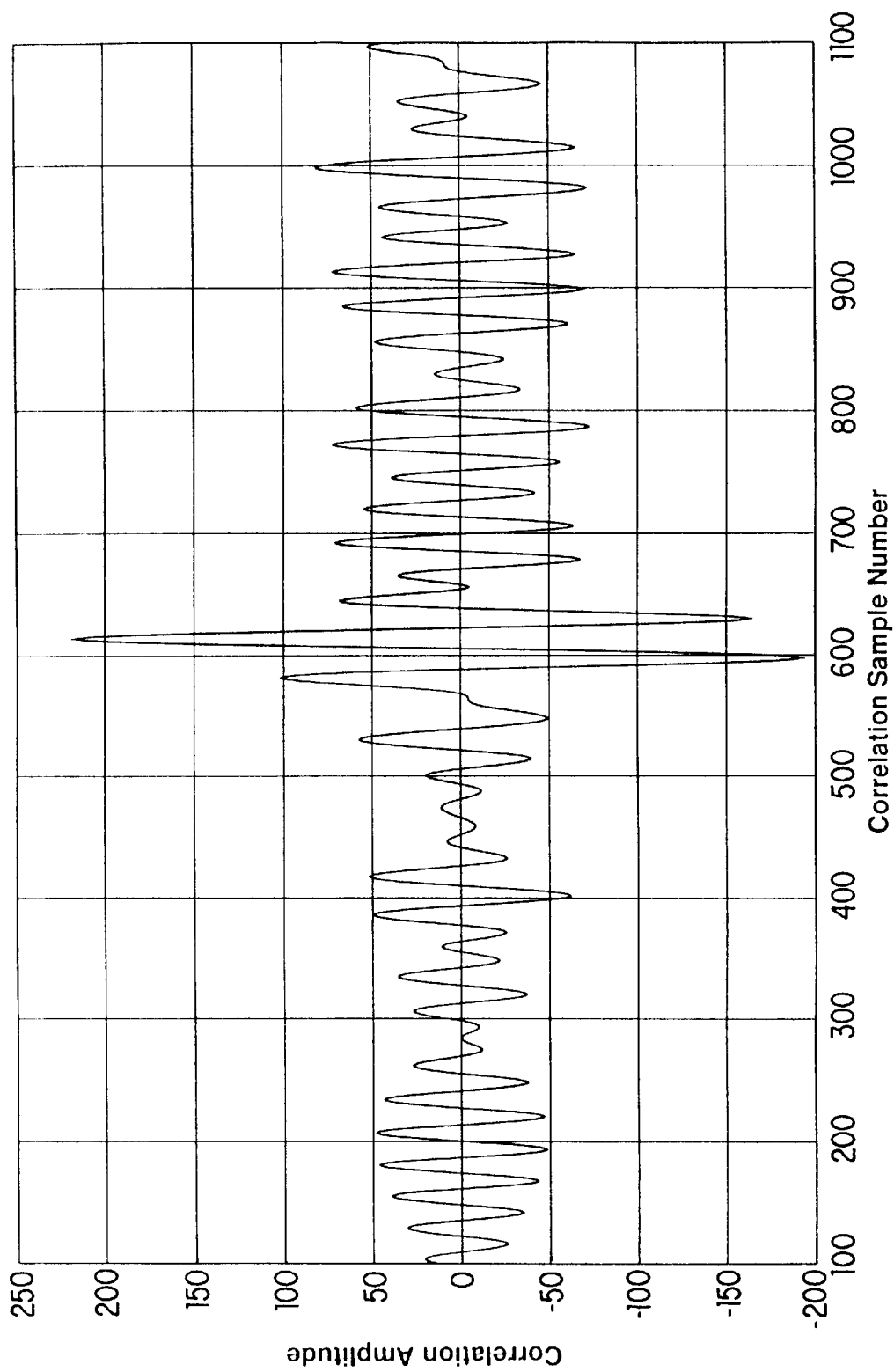
Figure 19C:
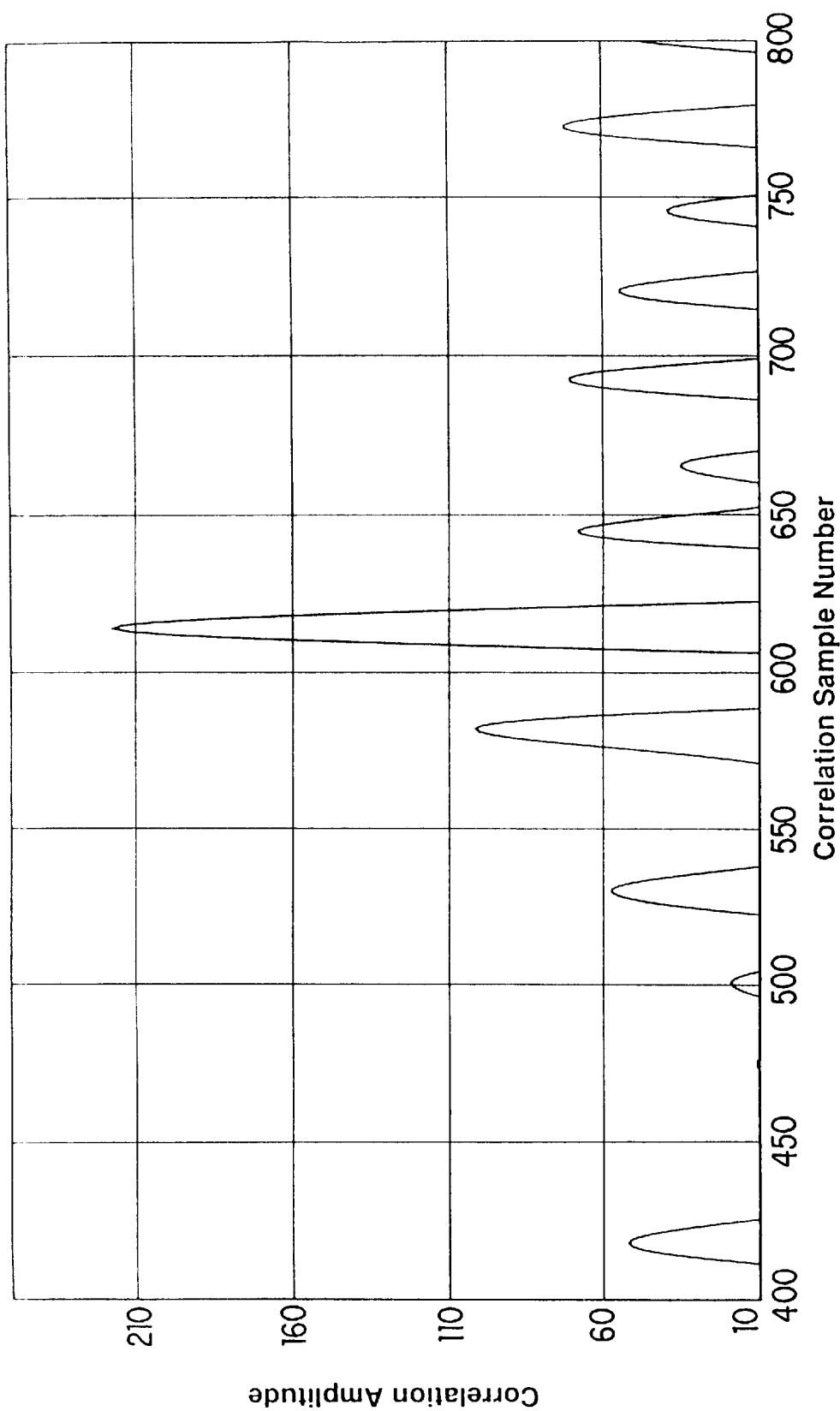

FIG. 19A is a plot of the frequency modulation vector used to produce the signal of FIG. 18A; FIG. 19B is a plot of the cross-correlation function for the signal of FIG. 18A after addition of the same noise vector used to produce FIG. 17A showing that the cross-correlation function has a central correlation peak at sample number 613; FIG. 19C is an expanded view of the correlation function around the central correlation peak of FIG. 19B.

Figure 20:
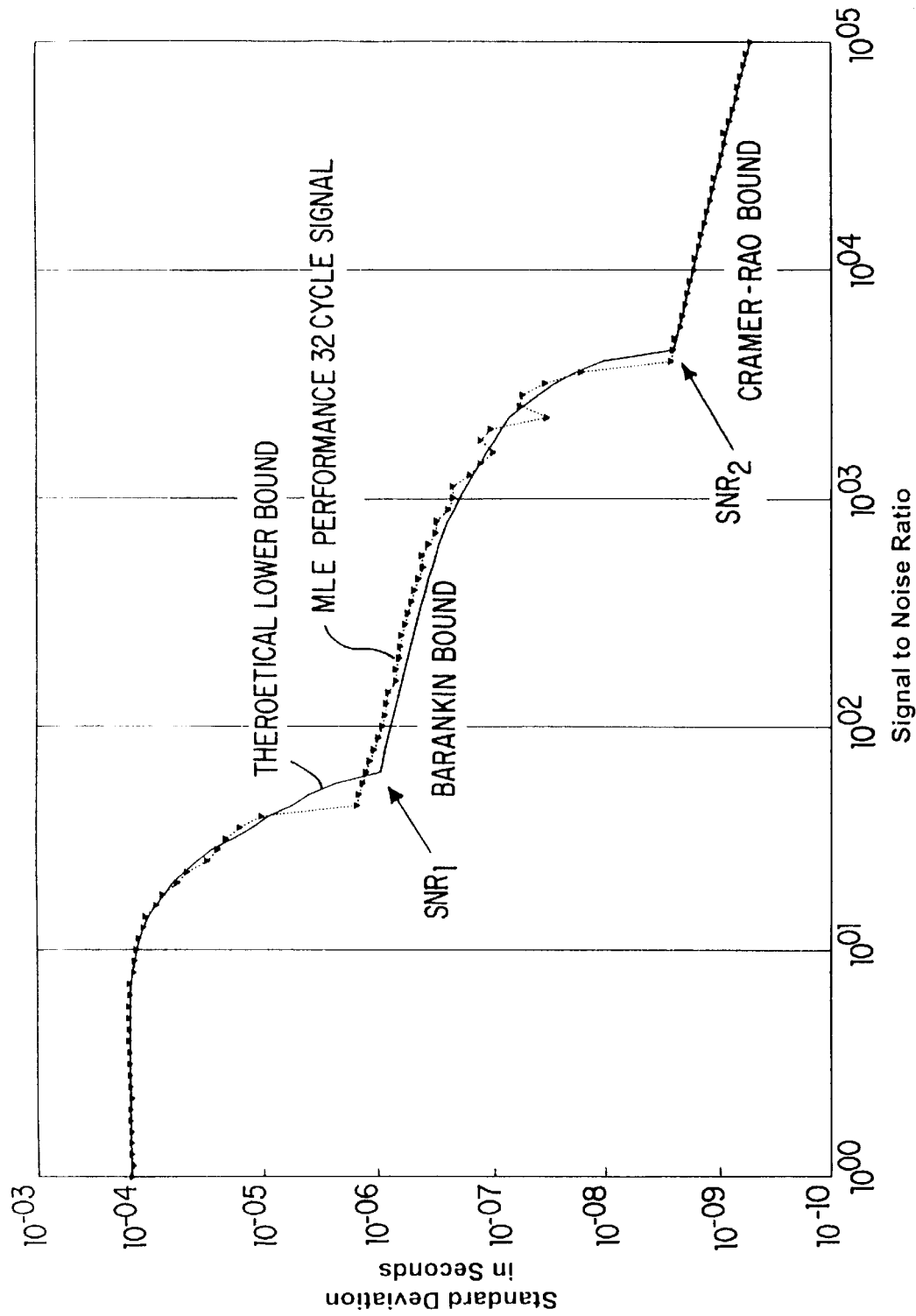

FIG. 20 is a plot of standard deviation in seconds versus signal to noise ratio as defined by Zeira and Schultheiss. The plot illustrates the performance of the maximum likelihood estimator for a 32 cycle unmodulated signal compared to realizable lower bounds.

Figure 21:
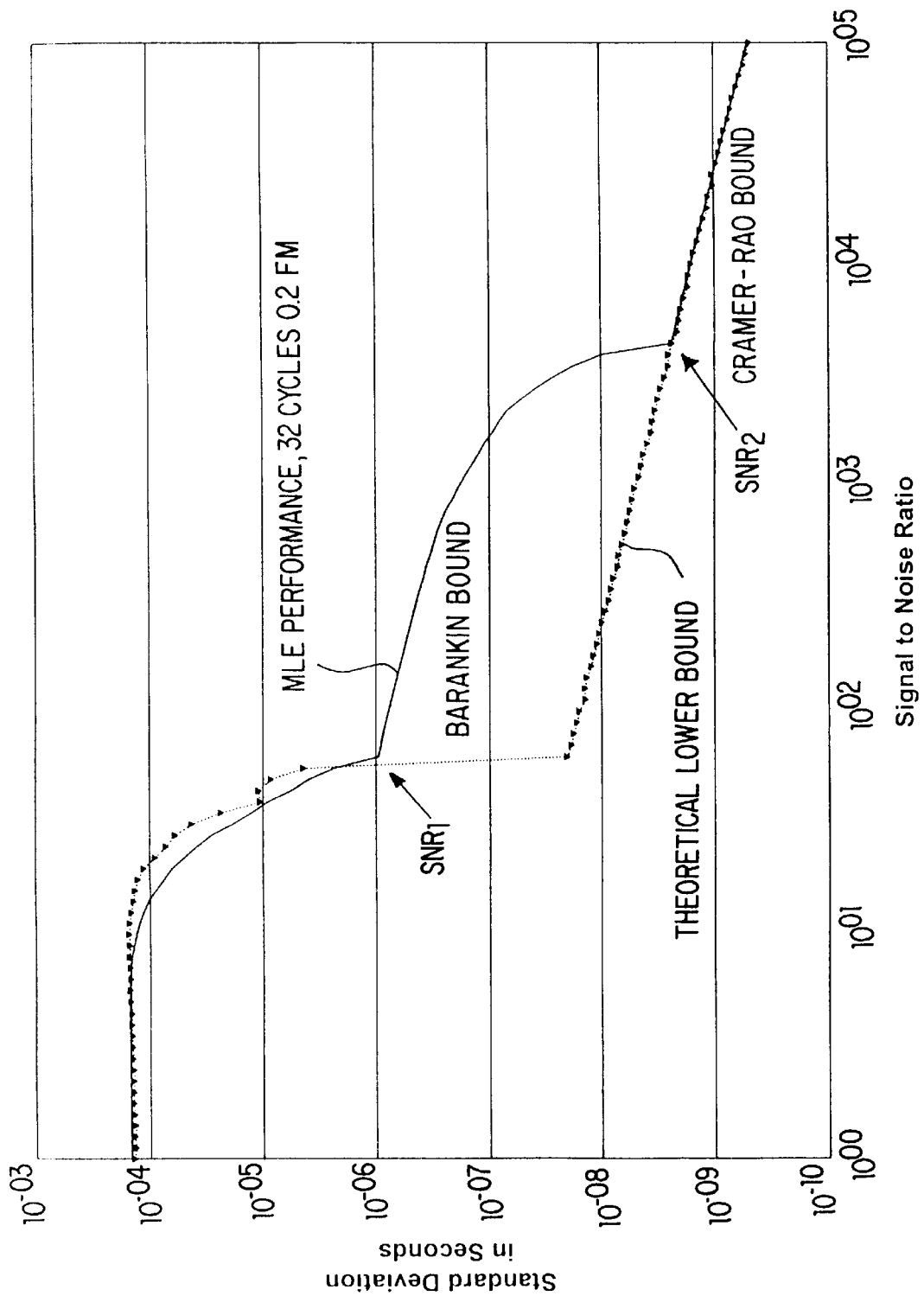

FIG. 21 is a plot of standard deviation in seconds versus signal to noise ratio as defined by Zeira and Schultheiss. The plot illustrates the performance of the maximum likelihood estimator for a 32 cycle, 0.2 frequency-modulated signal compared to realizable lower bounds.

Figure 22A:
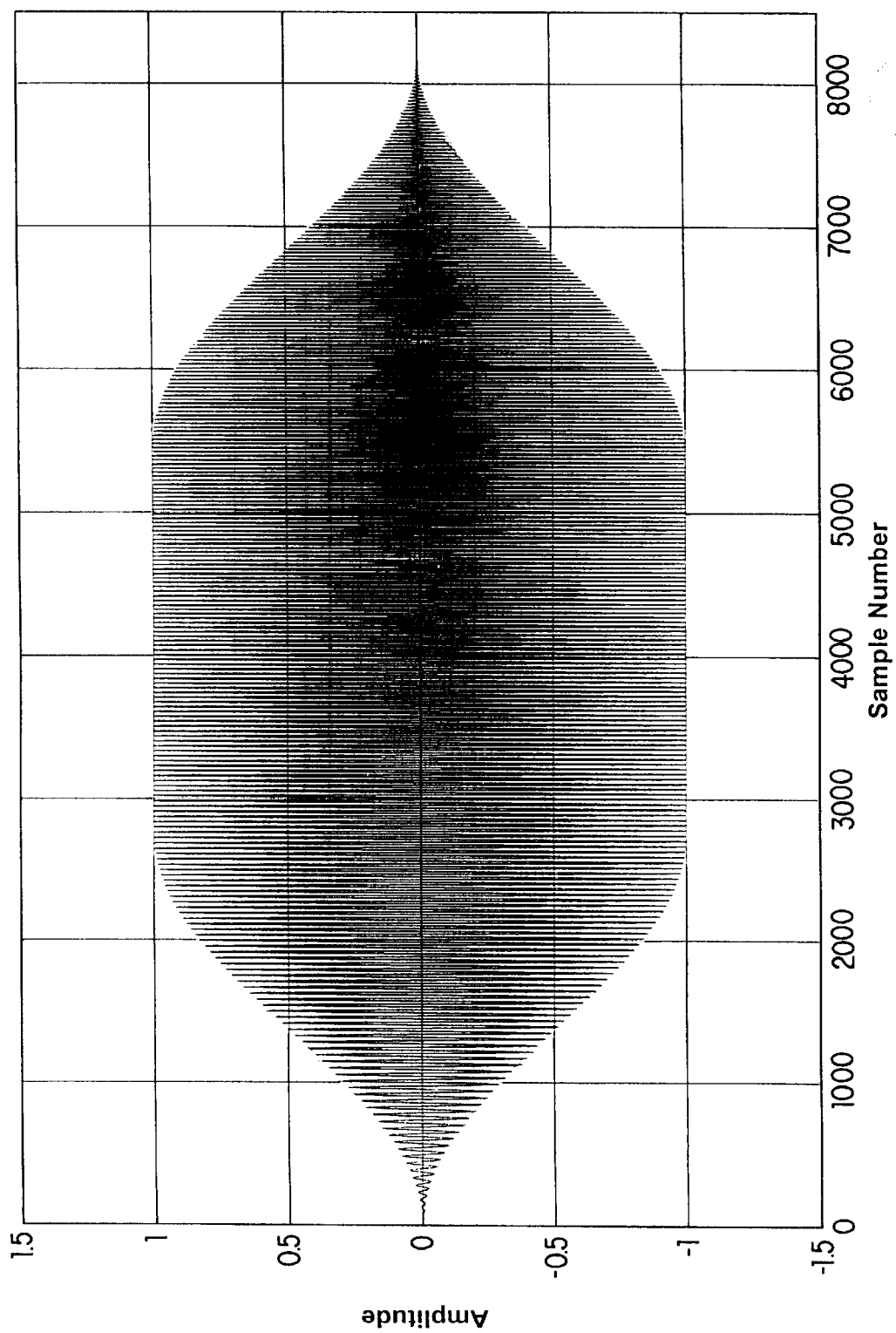
Figure 22B:
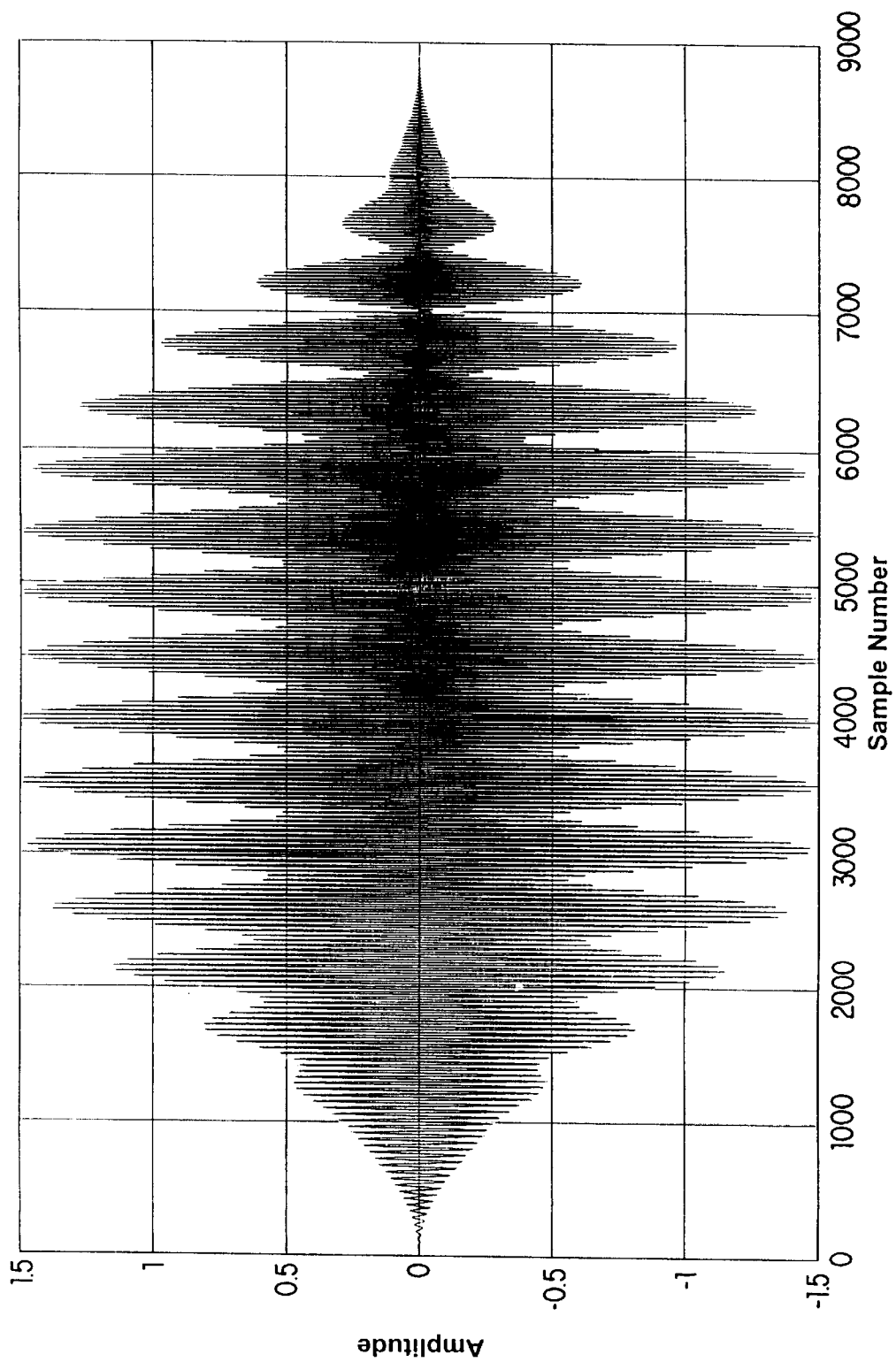
Figure 22C:
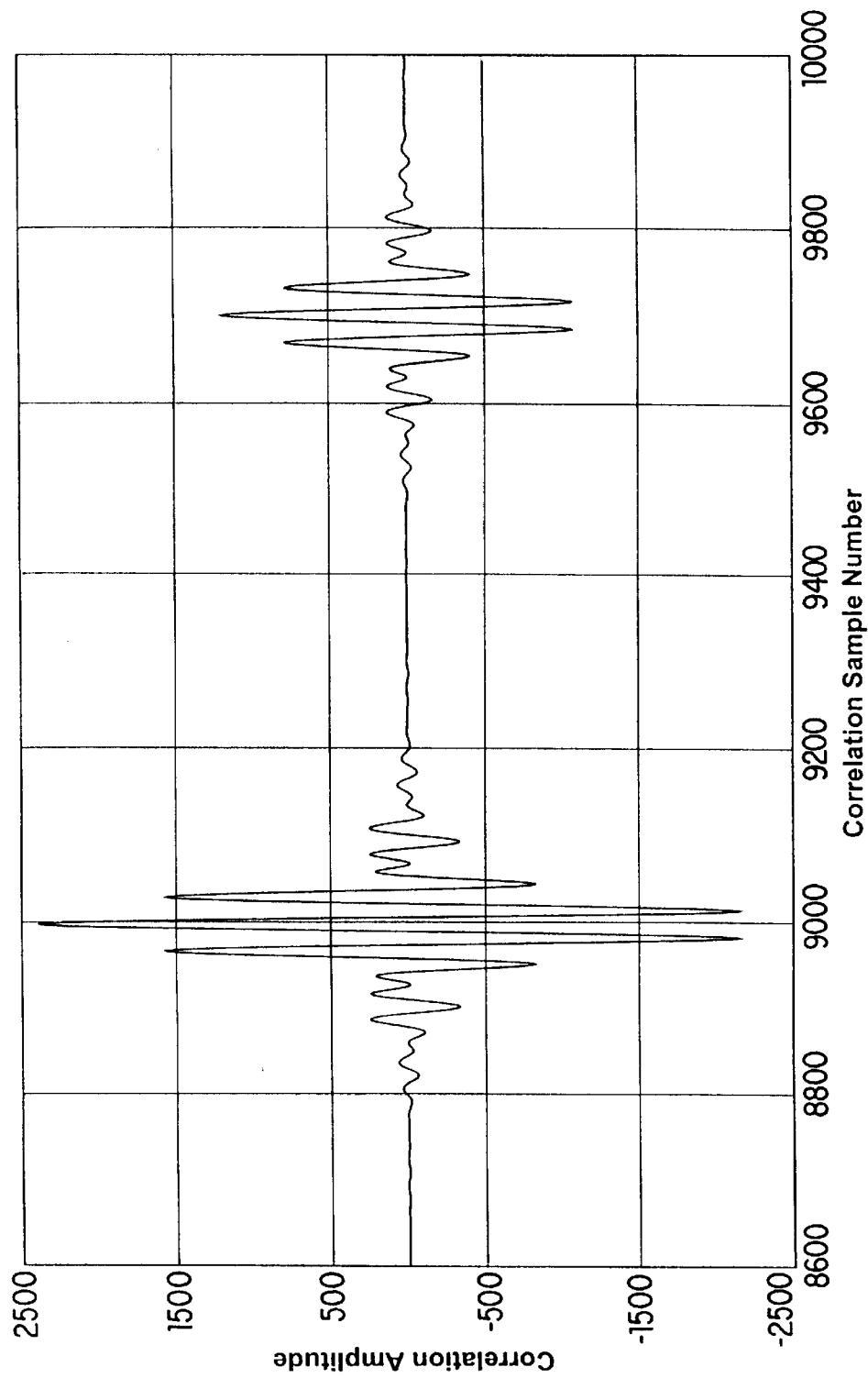

FIG. 22A is a plot of a noise-free, windowed, 256 cycle, 0.2 frequency-modulated signal. FIG. 22B is a plot of the signal of FIG. 22A added to a delayed (22 $\mu$sec) and attenuated (0.5×) copy of itself FIG. 22C is a plot of the cross-correlation function for the signal of FIG. 22B.

Figure 23A:
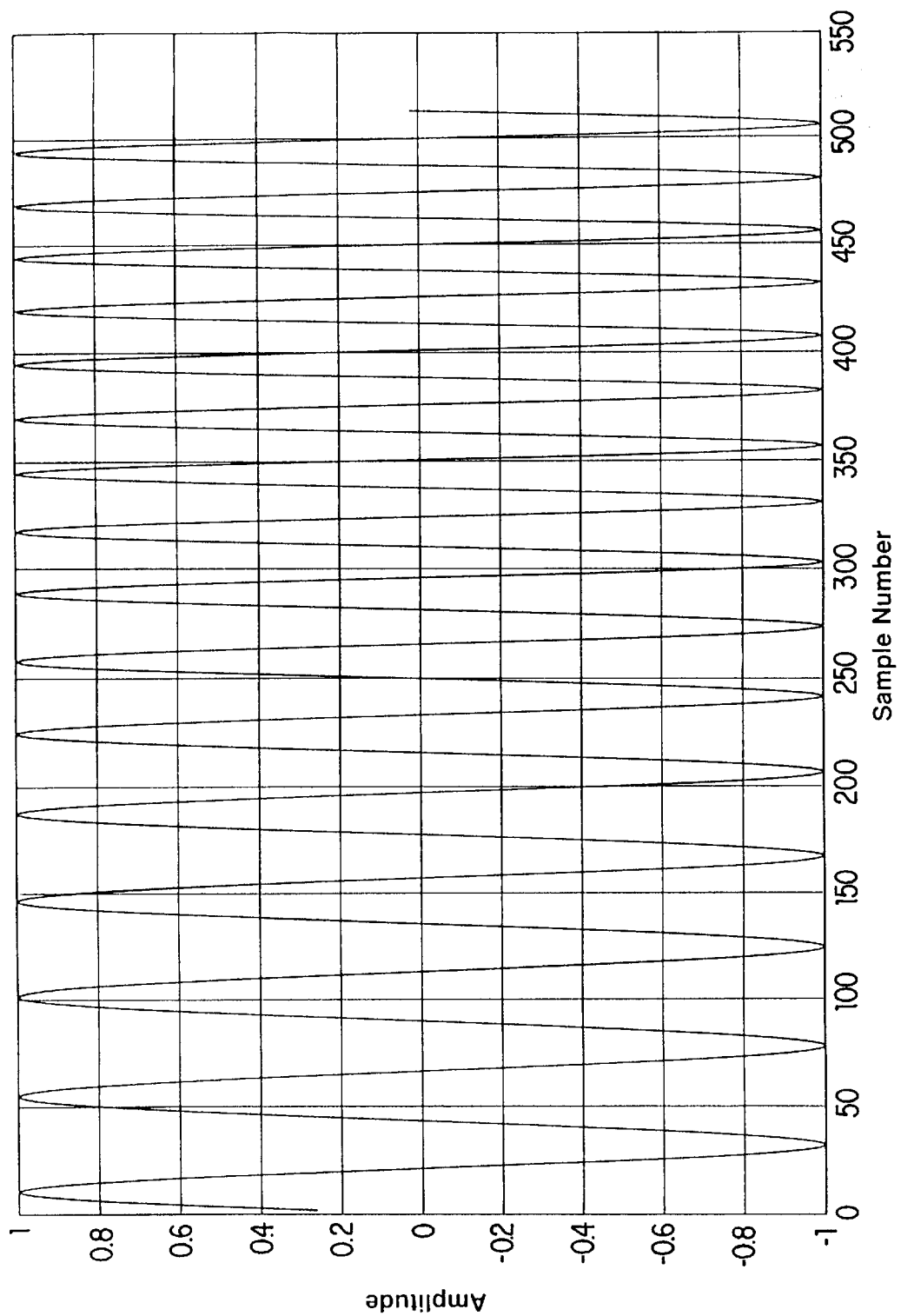
Figure 23B:
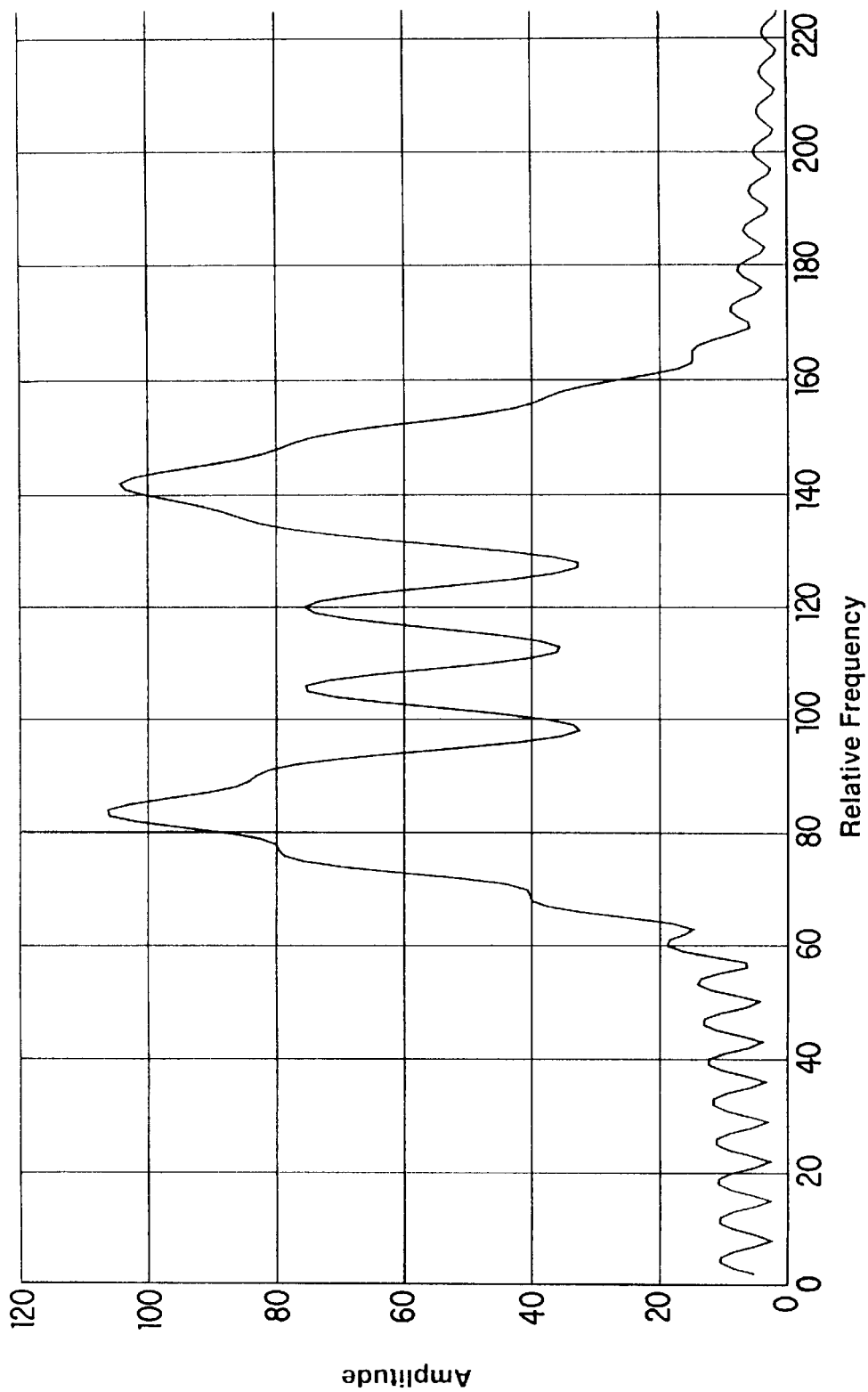

FIG. 23A is a plot of a noise-free, unwindowed, 16 cycle, 0.2 frequency-modulated signal; FIG. 23B is a plot of the frequency spectrum of the signal of FIG. 23A showing the signal's "ringing".

Figure 24A:
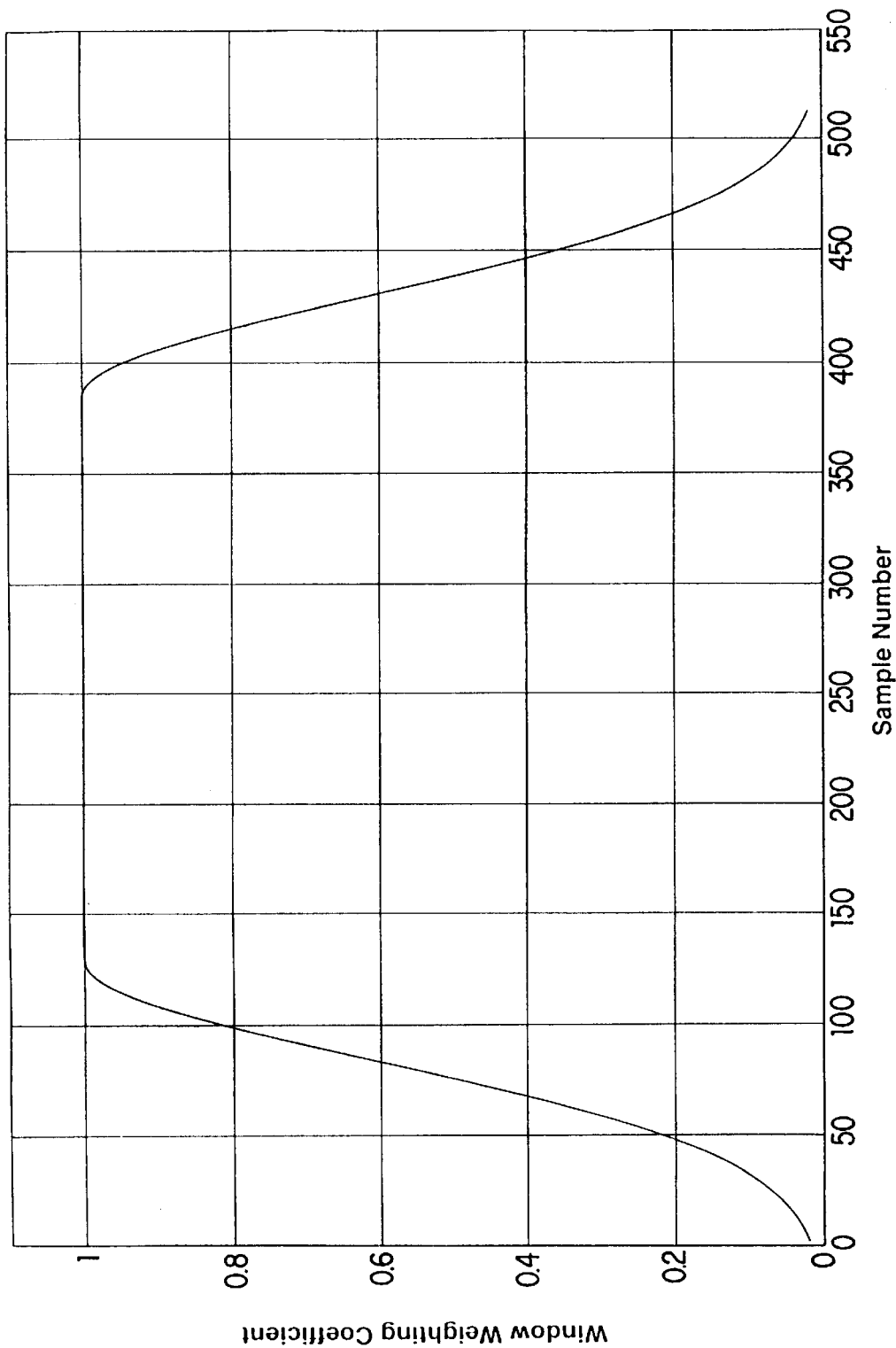
Figure 24B:
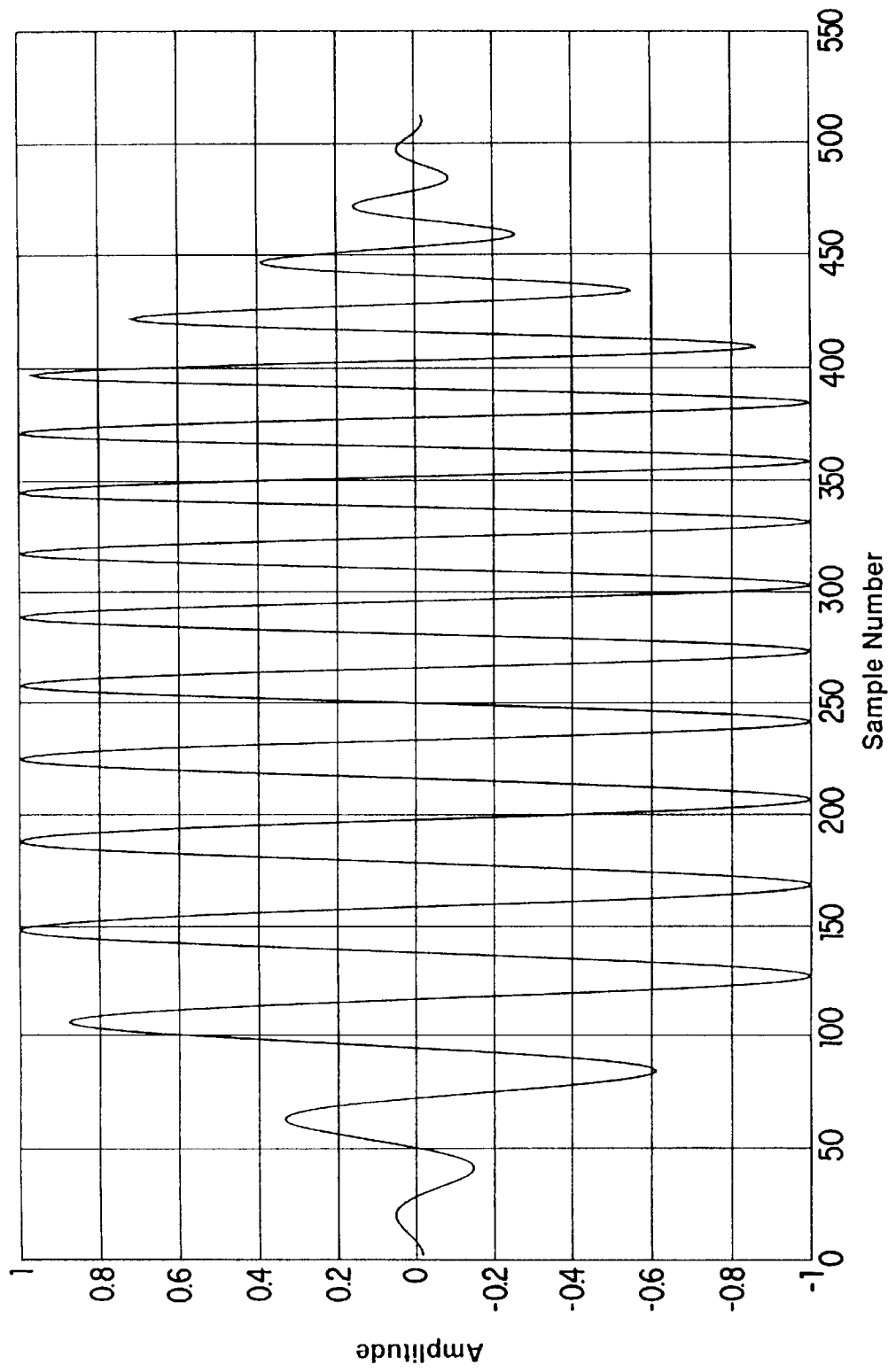
Figure 24C:
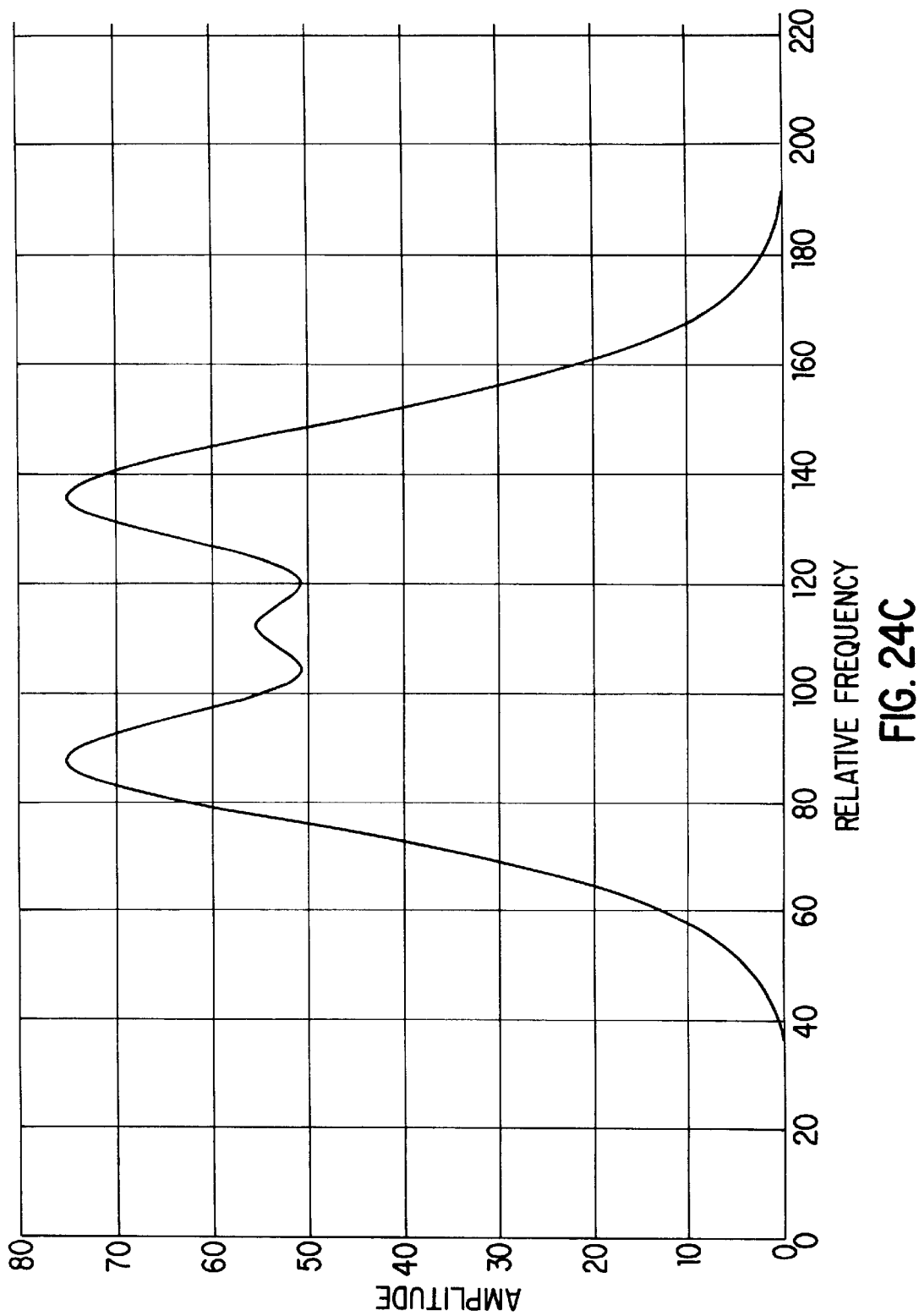

FIG. 24A is a plot of the window function used to produce the windowed, 16 cycle, 0.2 frequency-modulated signal of FIG. 24B; FIG. 24C is a plot of the frequency spectrum of the signal of FIG. 24B showing the elimination of "ringing". To obtain higher resolution in the frequency spectra of FIGS. 23B and 24C, padding zeros were added to the signals of FIGS. 23A and 24B before the spectra of those signals were calculated. The relative frequency values plotted in FIGS. 23B and 24C are given by f·3583/$F_s$ where f is the calculated frequency value and $F_s$ is the sampling frequency.

Figure 25:
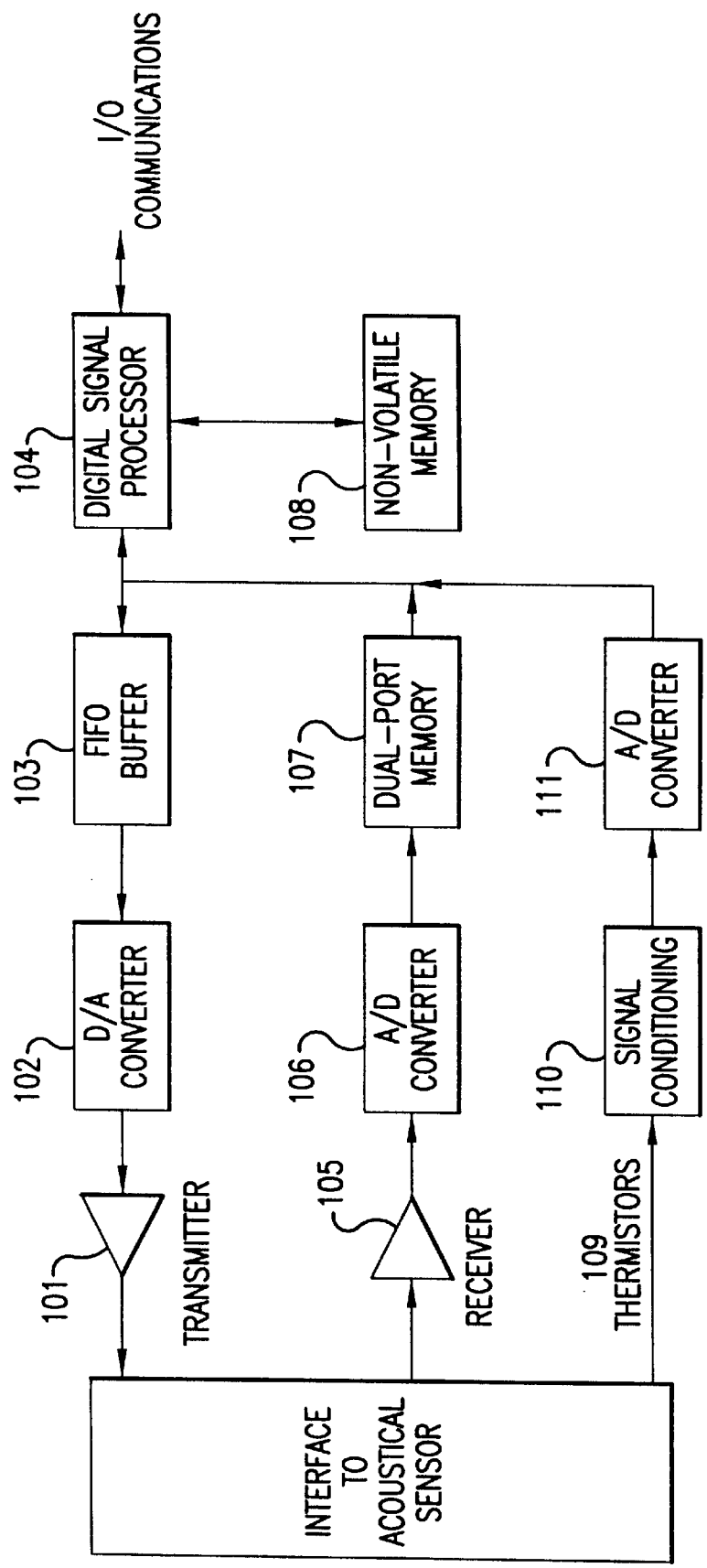

FIG. 25 is a block diagram of various hardware elements which can be used to implement the digital signal processing aspects of the invention This block diagram is for an acoustic sensor which employs two transducers, one of which serves as a component of an acoustical pulse transmitter and the other of which serves as a component of an acoustical pulse receiver.

Figure 26A:
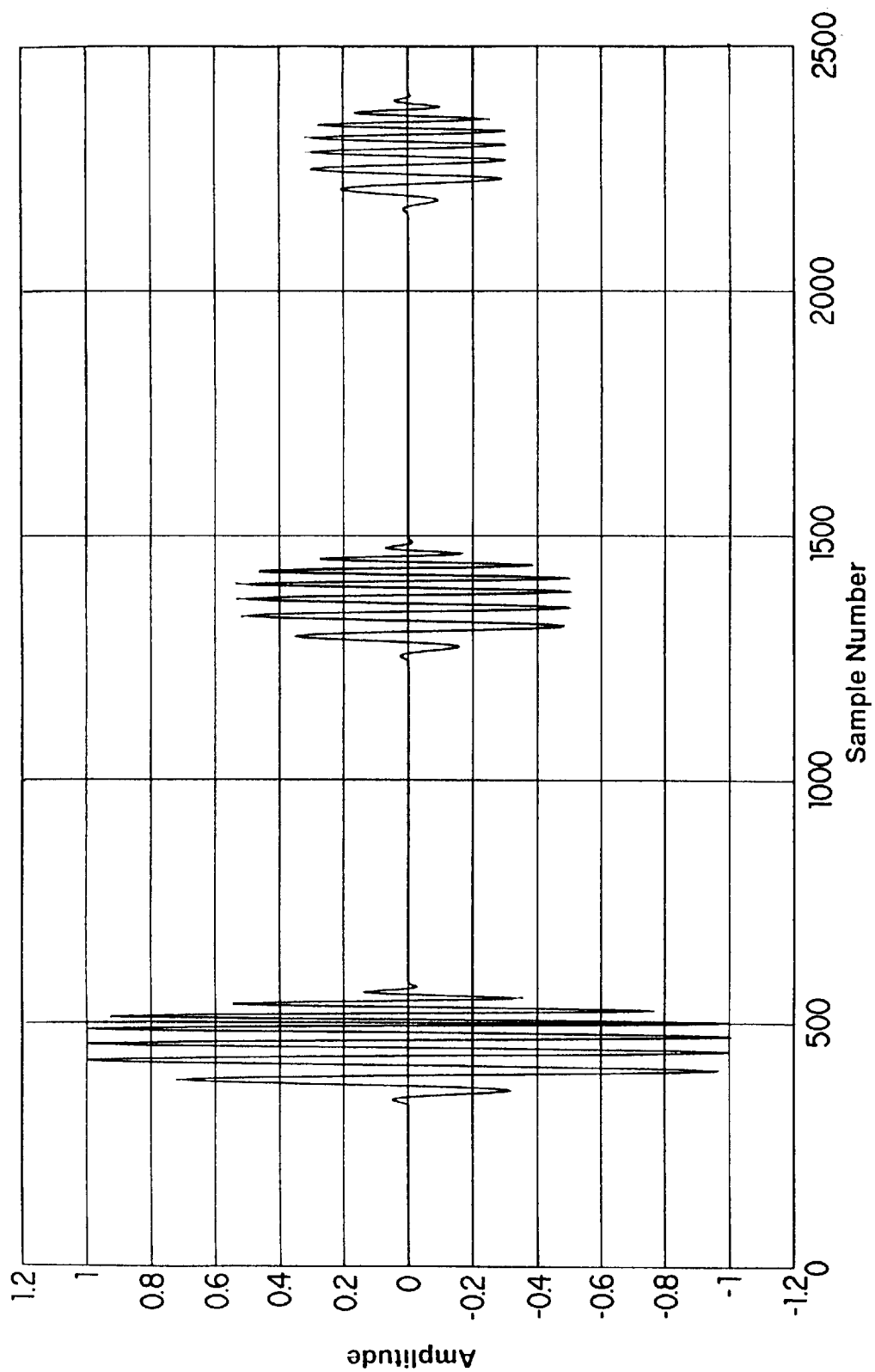
Figure 26B:
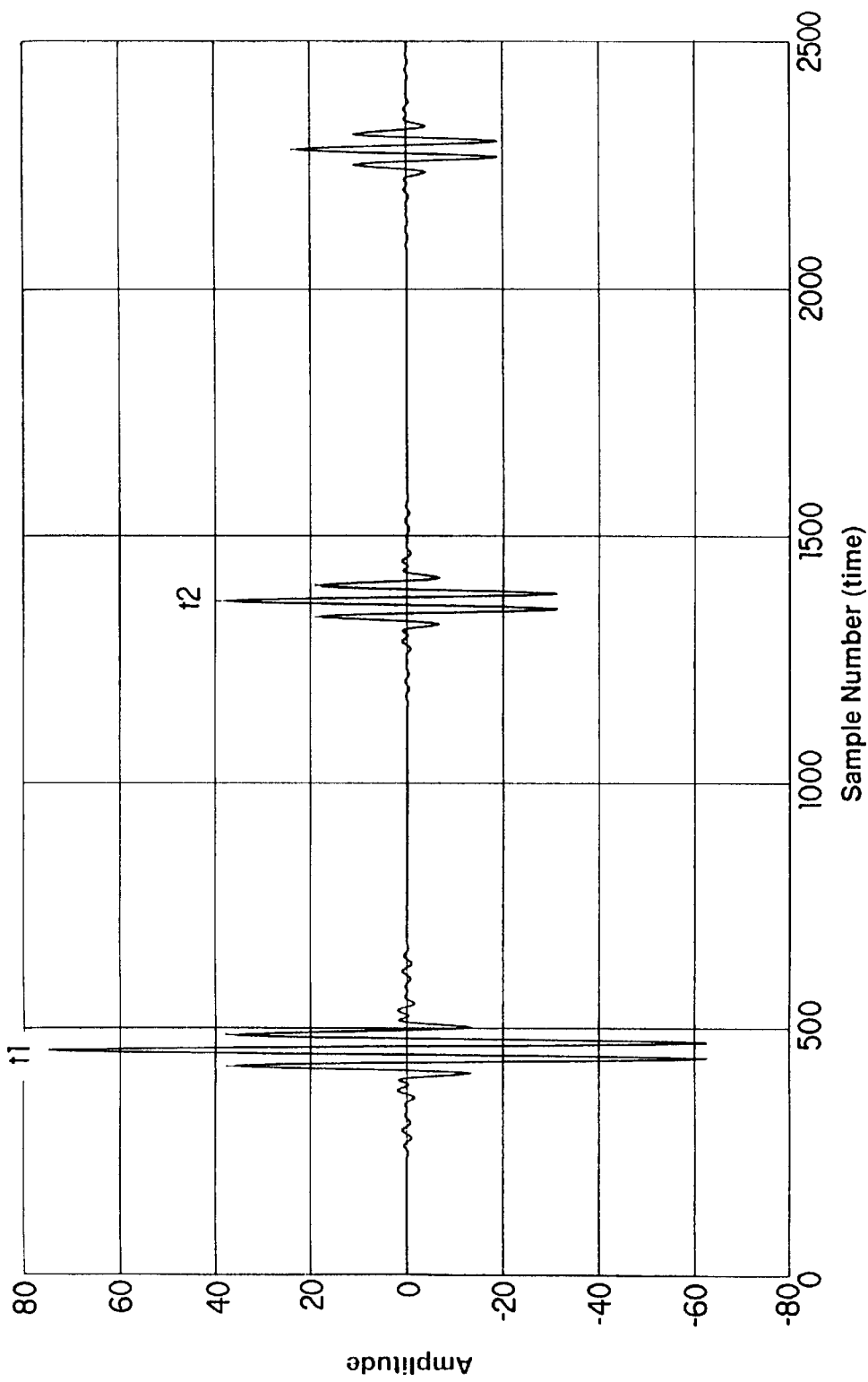

FIG. 26A is a plot of a received signal showing the first three waveforms, namely the direct path signal and two successive echo signals; FIG. 26B shows the results of cross-correlating a stored template signal with the received signal of FIG. 26A. The times $t_1$ and $t_2$ are measured from the initiation of the transmitted pulse to the respective first two cross-correlation peaks.

Figure 27:
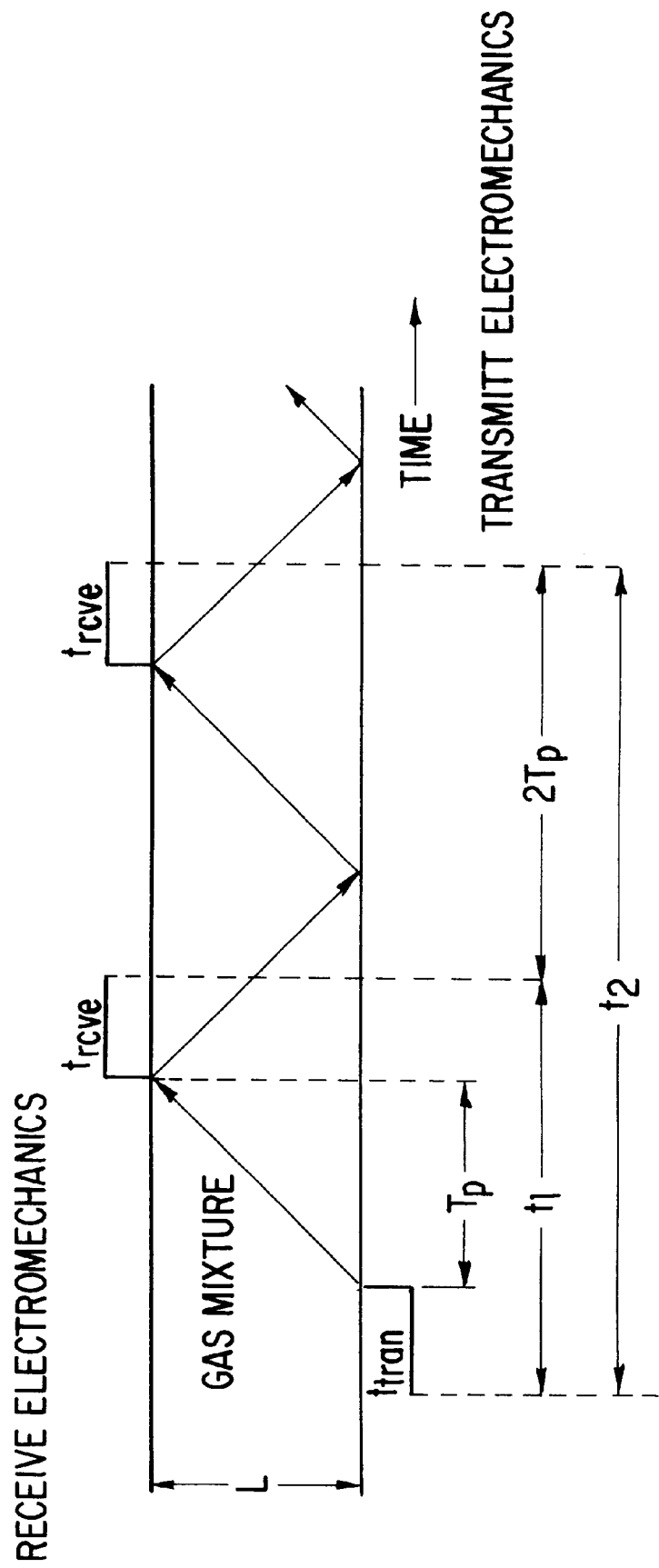

FIG. 27 is a timing diagram for a transmitter and receiver separated by a distance L.

Figure 28A:
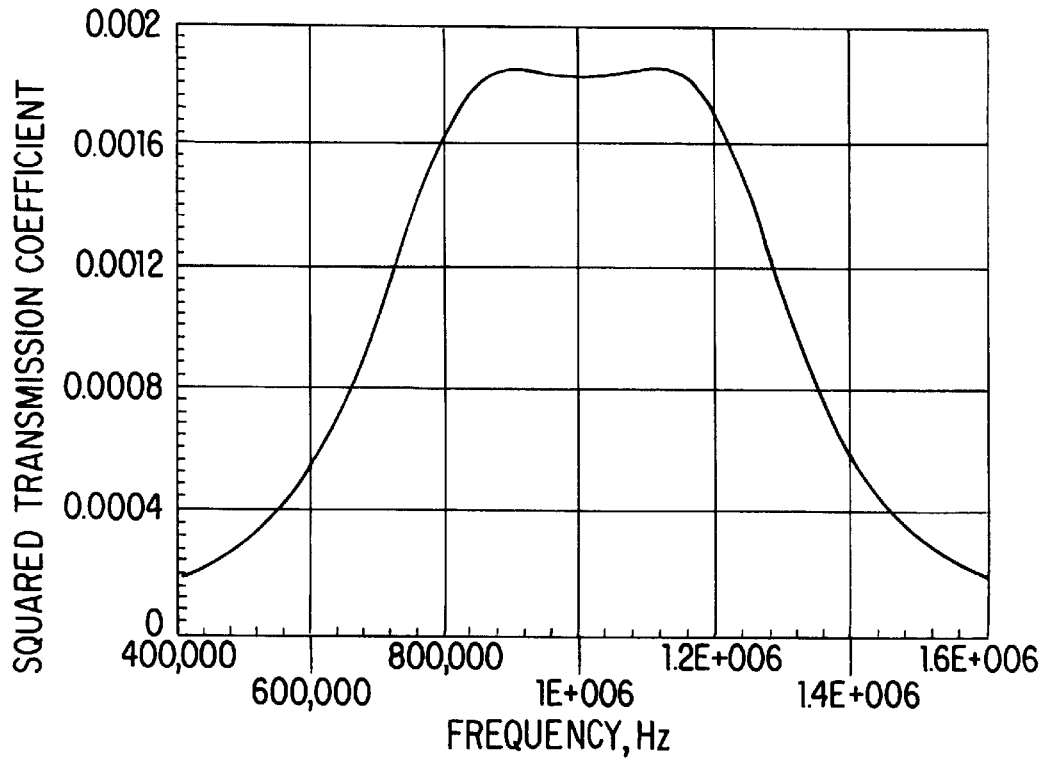

FIG. 28A is a graph showing the squared transmission coefficient of an acoustical transformer having an aluminum layer and a PVDF layer.

Figure 28B:
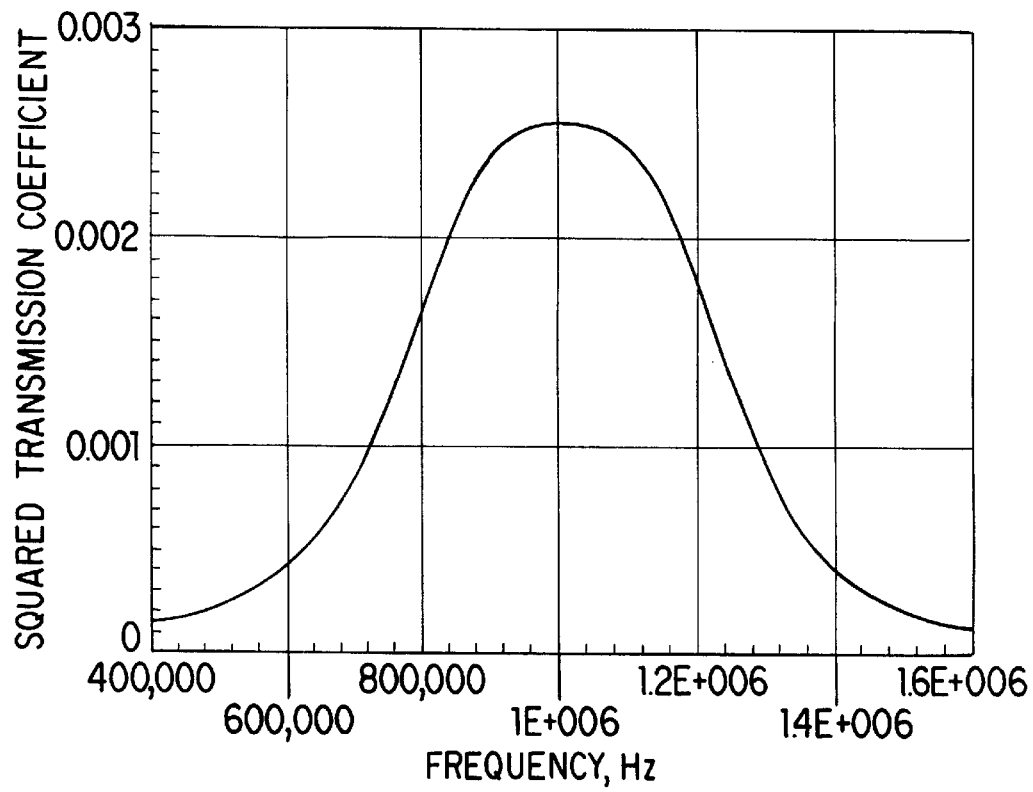

FIG. 28B is a graph showing the squared transmission coefficient of an acoustical transformer having an aluminum layer, an INCONEL layer, and a TEFLON layer.

Figure 29:
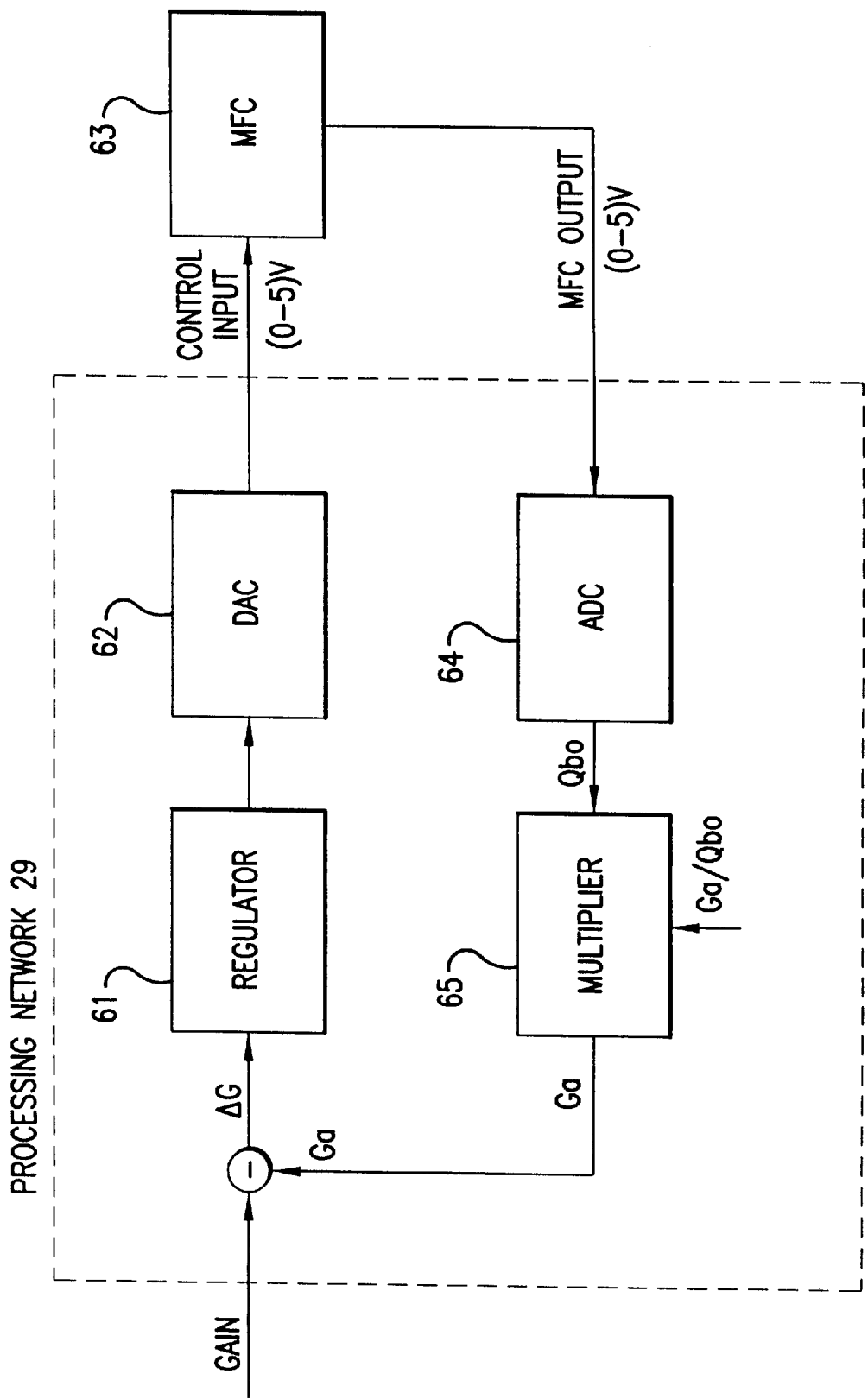

FIG. 29 is a block diagram of various hardware elements which can be used to implement the mass flow control aspects of the invention.

Figure 30A:
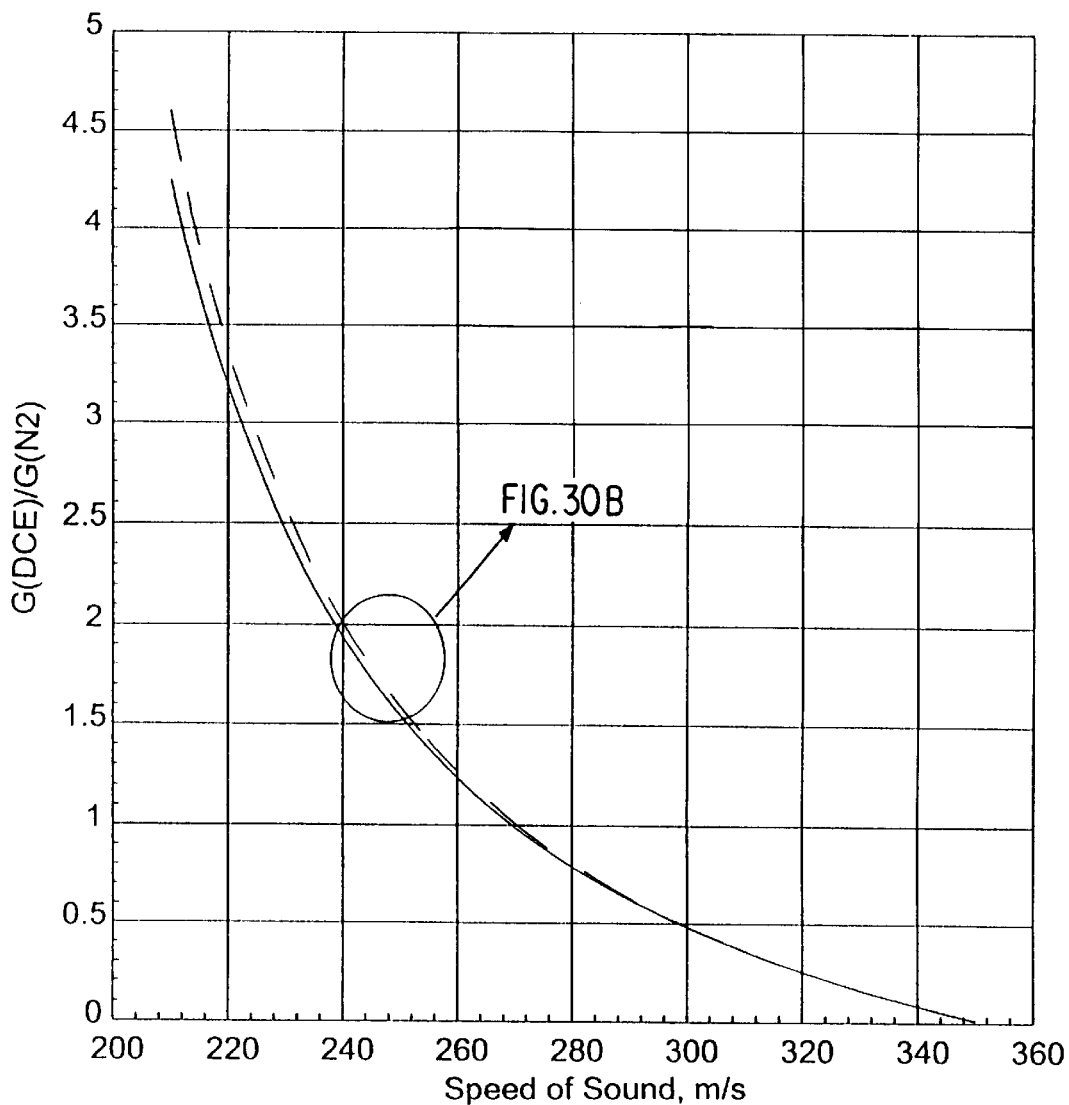
Figure 30B:
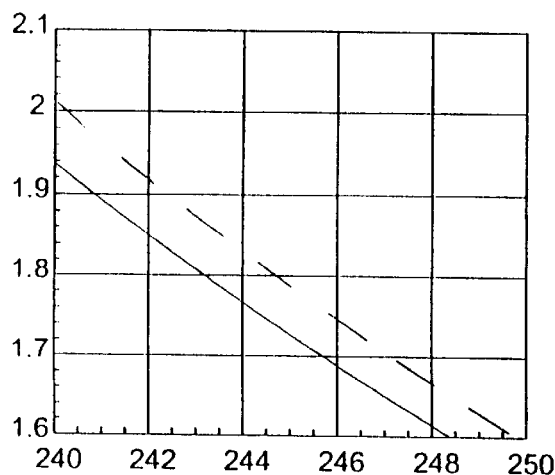

FIG. 30 is a graph comparing the mixing rule of the prior art (dashed line) with the mixing rule of the present invention (solid line) for a mixture of trans-1,2-dichloroethylene and nitrogen.

V. DETAILED DESCRIPTION OF THE INVENTION AND ITS PREFERRED EMBODIMENTS

A. Introduction

As discussed above, the present invention relates to measurements performed on gases, liquids, and solids using a pulse of acoustical energy.

The most common applications of the invention involve measuring concentrations, volumetric flow ratios, and/or mass flow ratios of a binary gas mixture, although the invention can also be used to measure the compressibility, heat capacity, molecular weight, and/or temperature of a pure gas. Similarly, the invention can be used with gas mixtures containing more than two components. Also, various aspects of the invention can be employed in performing acoustical measurements on liquids and solids.

For ease of discussion, the following description of the invention will concentrate on the application of the invention to a binary gas mixture, it being understood that the use of this particular application to explain the invention is not intended to limit the scope of the invention as defined by the appended claims in any way.

In overview, the invention can be practiced in either a shadow format, with a separate transmitter and receiver, or an echo format, with only one transducer. The echo format is, in general, preferred but, as explained below, cannot always be used due to excessively high attenuation of the acoustical pulse by the test mixture.

FIG. 1 illustrates some of the basic elements of the invention. As shown therein, a pulse of acoustical energy having a leading edge 5 and a trailing edge 6 is emitted by transducer 1 and coupled into a test chamber by one or more matching layers 2, which serve to match the acoustical impedance of the transducer to that of the gaseous medium. In this way, efficient energy transfer is achieved between the transducer and the medium. The pulse of acoustical energy produced in this way constitutes the transmitted signal S(t).

Considering first the case of an echo format, the transmitted signal is reflected by reflector 3 and returns to the matching layer(s)/transducer combination which now functions as a receiver to produce first received signal $r_1(t)$. Part of the returning pulse is reflected by the outermost matching layer and returns to reflector 3, where it is again reflected back to the matching layer(s)/transducer combination for detection as second received signal $r_2(t)$. This process continues with the received signal becoming weaker with each passage through the medium until it can no longer be detected at the matching layer(s)/transducer combination.

In accordance with certain aspects of the invention, the speed of sound is preferably determined by the time difference between two received pulses. In most cases, the two received pulses will be the first and second received pulses as shown in FIG. 1, although any two received pulses can be used, e.g., one can use received pulses 1 and 3, 2 and 4, 2 and 3, etc. Similarly, multiple pairs of pulses can be used if desired, with the time differences for the various pairs being averaged.

For ease of reference, the received pulse which is detected later in time will be referred to herein and in the claims as the "m-passage pulse" and the pulse detected earlier in time as the "n-passage pulse", where "m" and "n" are the number of passages which the pulse made in either direction across the chamber before being detected, "m" being greater than "n". Thus, in FIG. 1, $r_1(t)$ is a 2-passage pulse and $r_2(t)$ is a 4-passage pulse. It should be noted that the difference between "m" and "n" is an even number, i.e., m−n=2i, where "i" is an integer.

Turning to the case of a shadow format, instead of reflector 3, this format uses one or more matching layers and a receiving transducer 4. Again, the matching layers serve to efficiently couple acoustical energy between the test medium and the transducer. As with the echo format, the speed of sound is preferably determined using the time difference between two received pulses, e.g., the first and second received pulses $r'_1(t)$ and $r'_2(t)$ in FIG. 1. In terms of the m-passage and n-passage nomenclature, in this case, the first received pulse is a 1-passage pulse, while the second received pulse is a 3-passage pulse. Note that m−n is again an even number.

As shown in FIG. 1, the echo format uses a single transducer while the shadow format uses two transducers. These transducers are piezoelectric elements which transform electrical energy to mechanical energy and vice versa. Such elements inherently have a number of modes of vibration, namely, a radial mode, a flexure mode, and a thickness mode.

Each of these modes has a fundamental frequency and overtones (harmonics) of the fundamental.

For purposes of the preferred embodiments of the invention, all modes and harmonics other than the fundamental thickness mode represent undesirable spurious signals. Excitation of flexure modes can be minimized through the use of a piezoelectric element having only two electrodes symmetrically located on each side of the element. Although effective against flexure modes, this arrangement does not suppress the radial mode which is directly excited along with the thickness mode.

To a large extent, errors due to excitation of radial mode vibrations are automatically dealt with as a result of operating the system in its preferred configuration where the receiver is in the near field zone of the transmitter. Such operation means that the characteristic dimension of the piezoelectric element (e.g., the diameter in the case of a circular element and the shortest side in the case of a rectangular element) is in general large compared to the thickness dimension. This results in the mechanical resonant frequency of the fundamental radial mode being considerably lower than the fundamental mechanical resonant frequency of the thickness mode so that excitation of the thickness mode does not substantially excite the radial mode. To further suppress the effects of radial mode excitation it is desirable to design the electrical interface(s) with the piezoelectric element(s) to achieve efficient coupling with thickness mode vibrations and inefficient coupling with radial mode vibrations. Circuits for achieving such coupling are discussed below.

For either the echo or shadow format, the speed of sound ($C_M$) of a binary gas mixture can be obtained from the basic equation:

$$C_M = 2L/t_M \tag{12}$$

where $t_M$ is the measured time between two successive pulses at the receiver (e.g., in terms of the nomenclature of FIG. 1, $t_M$ equals $\Delta t$ for an echo format and $\Delta t'$ for a shadow format) and L is the distance between matching layer of the transmitter and the reflecting surface for an echo format or between the matching layers of the transmitter and receiver in the case of a shadow format.

Note that in the general case of the detection of an n-passage pulse followed by the detection of a m-passage pulse, the speed of sound is given by:

$$C_M = 2iL/(t_M - t_n) \tag{12a}$$

where m−n=2i and $t_m - t_n$ is the measured time difference between the pulses.

As can be seen from equation (12) or (12a), the accuracy of the speed of sound determination depends on the accuracy of a time measurement (i.e., $t_M$ or $t_m - t_n$) and a distance measurement (L). The time measurement aspects of the invention will be discussed first, followed by a discussion of procedures for accurately determining the distance "L".

B. Accurate Measurement of the Time Component of the Speed of Sound Determination (1) Acoustical Cell Structure and Electronics FIGS. 2–11 illustrate suitable apparatus for making accurate time measurements in both echo and shadow formats.

Figure 6:
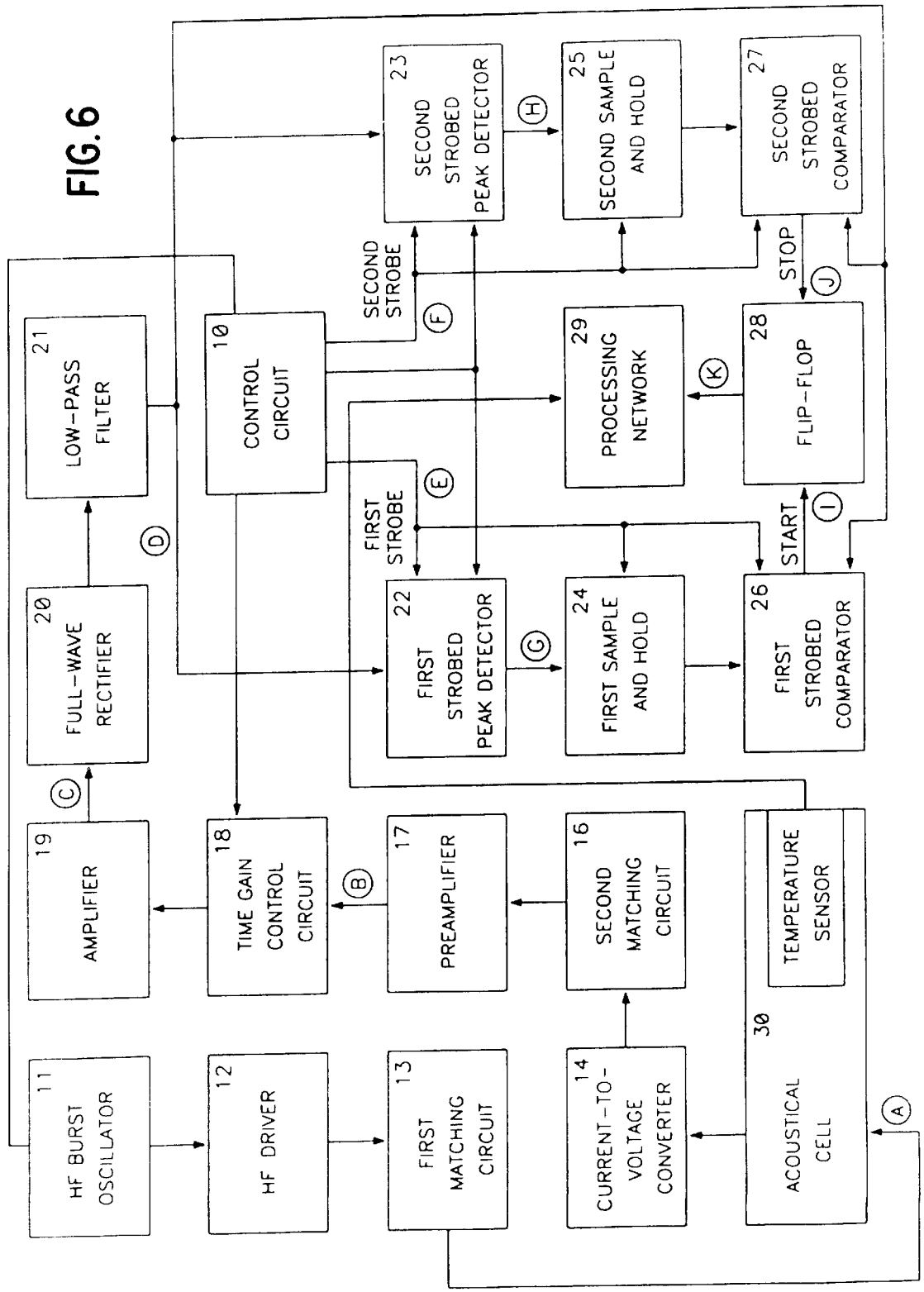
FIG. 6 is a block diagram of various hardware elements which can be used to implement the analog signal processing aspects of the invention. This block diagram is for an acoustic sensor which employs two transducers, one of which serves as a component of an acoustical pulse transmitter and the other of which serves as a component of an acoustical pulse receiver.
Figure 10:
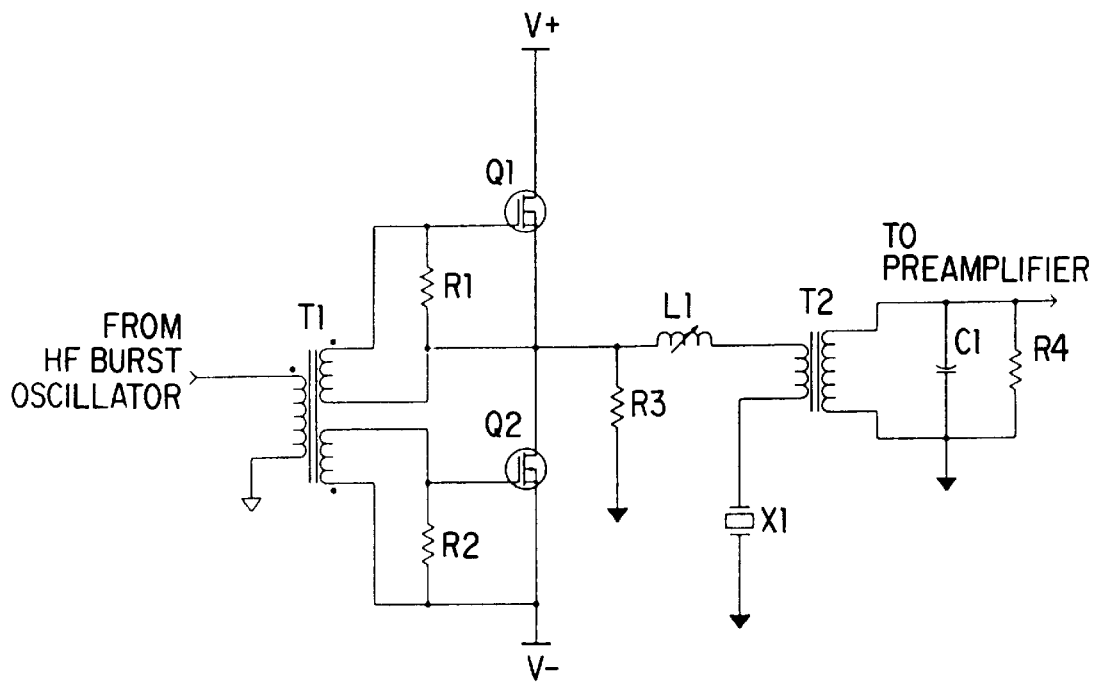
FIG. 10 is a schematic of representative electronic components which can be used with the single transducer embodiments of the invention.
Figure 11:
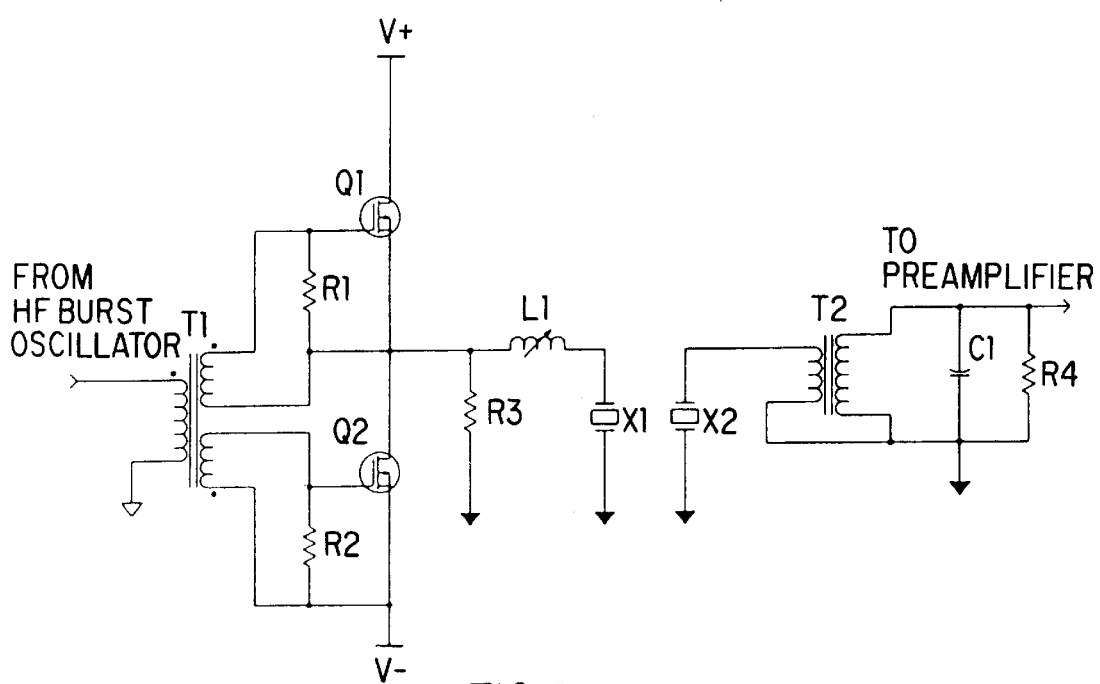
FIG. 11 is a schematic of representative electronic components which can be used with the two transducer embodiments of the invention.

In particular, FIG. 2 is a block diagram of suitable electronic assemblies which can be used in making echo format time measurements, while FIGS. 3 and 4–5 show the structures of two alternate embodiments of an acoustical cell 15 which can be used with this format. Similarly, FIG. 6 is a block diagram of suitable electronic assemblies for making shadow format time measurements, while FIGS. 7 and 8–9 show the structures of two alternate embodiments of an acoustical cell 30 for this format. FIGS. 10 and 11 show circuitry which can be used to implement the functions of various of the electronic assemblies of FIGS. 2 and 6, respectively.

Beginning with FIGS. 3–5 and 7–9, these figures show constructional layouts for echo format and shadow format acoustical cells, respectively. Body 31 of these cells, which defines test chamber 44, is composed of a high purity, corrosion resistive material, such as, stainless steel, quartz, a fluoropolymer, or the like. Stainless steel, e.g., 316L stainless steel, is a particularly preferred material for body 31.

Each of the acoustical cells includes a temperature sensor 47 for use in transforming speed of sound measurements to concentration measurements. This sensor can, for example, be a thermistor, such as a TO501/B2-P60BB103M-CQOGA manufactured by Thermometrics, Edison, N.J. The cells of FIGS. 4–5 and 8–9 are equipped with inlet and outlet VCR connectors 7,8 which facilitate incorporation of the cell into a production facility. These embodiments also include core 32 which together with body 31 equalizes the temperature of the incoming gas mixture with the core-body temperature.

Flow of the test mixture through test chamber 44 is indicated by arrow 9. For the embodiments of FIGS. 3 and 7, the center line of the test chamber is aligned with the cell's gas inlet and outlet, while for the embodiments of FIGS. 4–5 and 8–9, the center line and the inlet and outlet are orthogonal to one another. This later configuration allows for a more compact construction for the acoustical cell, as is desired for installation in a production facility.

Turning to FIG. 2, the electronic assemblies of this figure are designed to measure the concentration of a binary gas in an echo format using a single transducer which functions as both a transmitter and a receiver.

The overall apparatus is synchronized by a control circuit 10, which initiates a high frequency (HF) burst oscillator 11 that applies a short packet of sinusoidal electrical vibrations having a square-shaped envelope to HF driver 12. The frequency of these vibrations must be close to the thickness mode frequency of piezoelement 40. The piezoelement is selected to have a thickness mode operating frequency which is as high as possible in order to obtain highly accurate time measurements and to simultaneously provide a suitable signal-to-noise ratio and a suitable amplitude range for the detected pulses.

HF driver 12 amplifies the packet of electrical vibrations and applies them to first matching circuit 13 which is connected to current-to-voltage converter 14. The current-to-voltage converter is, in turn, connected to piezoelement 40.

First matching circuit 13 is designed both to increase the signal-to-noise ratio and to suppress interfering radial mode vibrations of the acoustic transducer by optimizing the electrical coupling to the transducer's electrical impedance at its thickness mode frequency. First matching circuit 13 supplies the acoustic transducer with the short packet (pulse) of sinusoidal vibrations during transmission and also provides electrical damping of the piezoelement.

The acoustical transducer of acoustical cell 15, i.e., piezoelement 40, converts electrical vibrations to mechanical and vice versa. As shown in FIGS. 3–5, piezoelement 40 is preferably significantly damped by mechanical damper 41. Mechanical damper 41 can be composed of, for example, tungsten powder mixed with a low viscosity epoxy, the proportions used depending upon the specific configuration and components of the sensor. In general terms, the proportions of tungsten powder and epoxy should be chosen to maximize the amount of tungsten powder while keeping the epoxy as the continuous phase component of the mixture. In practice, it has been found that hand mixing of about 30% tungsten powder (12 micron particle size; Aldrich Chemical Company, Inc., Milwaukee, Wis.) and about 70% epoxy (Duralco 4461 low viscosity resin and hardener mixed and cured in accordance with the manufacturer's instructions; Cotronics Corporation, Brooklyn, N.Y.) produces a mixture of this type. Mechanical dampers having other compositions can, of course, be used in the practice of the invention.

As noted above, first matching circuit 13 also damps the piezoelement, the damping in this case being electrical. This combination of mechanical and electrical damping achieves high resolution of the received signals.

The operating surface of piezoelement 40 is acoustically matched to the low acoustical impedance of the test medium by means of a broadband and high efficiency multilayer acoustical transformer 42. The last layer of acoustical transformer 42 should be chemically inert to the chemicals making up the test medium. The use of these layers is especially important for a gaseous test medium because the ratio of the acoustical impedance of a ceramic piezoelement to the acoustical impedance of a gaseous medium is typically extremely high (e.g., over $10^5$). A discussion of preferred constructions for the acoustical transformer is set forth below.

For the echo format, acoustical vibrations propagate through the test medium inside acoustical chamber 44 to reflecting surface 45, and reflect back to the acoustic transducer. A small amount of the returning acoustical energy is converted to electrical vibrations by piezoelement 40, forming the first reflected signal, but most of the acoustical energy is reflected by acoustical transformer 42 and is directed back to the reflecting surface 45 through the test medium, and so on, forming the subsequent reflected electrical signals. The amplitudes of the received signals of course become progressively smaller due to absorption of the acoustical energy by the medium.

In some applications, specifically, when both the speed of sound in the test mixture and the absorption of the mixture are high (e.g., a hydrogen-carbon dioxide binary mixture), the transmitted pulse reverberation does not allow reliable separation of the first several reflections. A shadow format using a separate transmitter and receiver is preferred under these conditions.

FIGS. 6–9 show suitable apparatus for practicing this embodiment of the invention. The operation of the components of these figures is essentially the same as the corresponding components of FIGS. 2–5. The primary difference between the two embodiments is that the acoustical cell used with the shadow format has two piezoelements 40 and 48, rather than just one element. The two elements are preferably constructed in such a way that the resonance frequency of the transmitter is close to the antiresonance frequency of the receiver's transducer. For broad band transducers this condition is always fufilled by simply choosing the same type of piezoelement for both transducers. The frequency of operation of the system needs to be close to the thickness mode frequency of both elements. As with the single transducer embodiment, the frequency of operation of the system should be as high as possible to obtain highly accurate time measurements and to simultaneously provide a suitable signal-to-noise ratio and a suitable amplitude range for the detected pulses.

For the shadow method embodiment, piezoelement 40 serves as an acoustical transmitter and converts electrical vibrations to mechanical vibrations, while piezoelement 48 serves as an acoustical receiver and converts mechanical vibrations back to electrical vibrations. Both piezoelements are significantly damped acoustically by dampers 41 and 49 and electrically by first matching circuit 13 and second matching circuit 16. Dampers 41 and 49 are preferably composed of the same material although different materials can be used if desired. As discussed above, a preferred damping material is tungsten powder mixed with a low viscosity epoxy.

The operating surfaces of piezoelements 40 and 48 are acoustically matched with the low impedance test medium by means of broadband, high efficiency, multilayer acoustical transformers 42 and 50. Preferably, acoustical transformers 42 and 50 have the same construction, although different constructions can be used if desired. As with the single transducer embodiment, the layer of each transformer which contacts the test medium should be chemically inert to the chemicals contained in the medium. Also as with that embodiment, acoustical transformers 42 and 50 perform the important function of ameliorating the effects of the impedance mismatch between the ceramic piezoelements and the gaseous test medium. As indicated above, a discussion of preferred constructions for such transformers is set forth below.

In operation, acoustical vibrations generated by piezoelement 40 propagate through acoustical transformer 42 and then through the flowing test medium inside acoustical chamber 44 to reach acoustical transformer 50. A small amount of the acoustical energy is converted to electrical vibrations by piezoelement 48, forming the first received signal, but most of the acoustical energy is reflected back to acoustical transformer 42. At that transformer, most of the acoustical energy is again reflected and directed back to acoustical transformer 50 through the test medium, and so on, forming the following received electrical signals. As with the single transducer embodiment, the amplitudes of the received signals become progressively smaller due to absorption of the acoustical energy by the medium.

As shown in FIGS. 3–5 and 7–9, acoustical cells 15 and 30 preferably include at least one and in some embodiments two diffusers 46 which provide a substantially uniform flow of the test medium in the region through which the acoustical beam passes, even at high flow rates. The diffuser(s) and the overall dimensions of the acoustical cell should be selected to avoid excessively turbulent flow at the anticipate maximum flow rate for the system. In this way, stable and repeatable time measurements which are essentially independent of the flow rate can be obtained. In addition to providing uniform flow, the diffuser also can provide the test medium with a stable and uniform temperature. To perform this function, the diffuser should have a high thermal conductivity and a thermal capacity which is much higher than the thermal capacity of the flowing test medium.

Although the diffuser can take various forms, a construction which has been found to work successfully in practice constitutes a matrix of small holes or slits in a metallic body. For example, the diffuser can be implemented as a rectangular 9 by 27 array of 0.031" (0.79 mm) diameter holes on 0.0625" (1.59 mm) centers in a 0.040" (1.02 mm) thick sheet of metal such as a sheet of 316L stainless steel. This configuration has been found to produce undeveloped laminar flow in the region of chamber 44 which includes the acoustical path, i.e., the flow has been found to be non-turbulent with a substantially rectangular velocity profile so that the velocity of the flowing gas mixture is nearly constant throughout the volume of gas through which the acoustical beam passes.

For both the echo and shadow formats, the operating frequency of the system is chosen based on the expected speed of sound in the test medium, any molecular relaxation effects which the test medium is expected to exhibit, the path lengths for the m-passage and n-passage pulses, and the range of concentrations to be measured. The operating frequency will generally be between 0.5 megahertz and 10 megahertz.

As shown in FIGS. 2 and 6, all received electrical signals pass through current-to-voltage converter 14, second matching circuit 16, and high sensitivity, linear preamplifier 17. It is known that a major source of noise for any apparatus which detects ultrasonic waves is random thermal motion of electrons in the electrical resistance at the apparatus' input. The rms value of this thermal noise is given by the Nyquist equation:

$$\bar{u} = \sqrt{4kTR_a \Delta f} \tag{13}$$

where k is Boltzmann's constant for an ideal gas; T is absolute temperature in °K; $R_a$ is the input resistance; and $\Delta f$ is the electrical bandwidth of the amplifier.

By using a current-to-voltage converter 14 which has a low output resistance and an output impedance which is in resonance with second matching circuit 16 at the operating frequency of the acoustic transducer, a significant reduction of two constituents in the above equation, i.e., the resistance $R_a$ and the bandwidth $\Delta f$, can be achieved. Such electrical coupling not only reduces the rms noise, but also allows a significant improvement in the signal-to-noise ratio in comparison with the traditional solution, where the acoustic transducer is connected directly to the voltage preamplifier (see Sirota et al. "On the improvement of the ultrasonic devices sensitivity", Defectoscopy, Vol. 3, 1986, Academy of Sciences of the USSR, Moscow, USSR).

Circuitry which can be used to implement the functions of first matching circuit 13, current-to-voltage converter 14, and second matching circuit 16 of FIG. 2 is set forth in FIG. 10. FIG. 11 sets forth similar circuitry for the corresponding electronic assemblies of FIG. 6. Suitable values for the various electrical components employed in these circuits are set forth in these figures.

On the transmitting side, these circuits supply the acoustical transducer with the sinusoidal electrical vibrations having a close to square-shaped envelope produced by HF burst oscillator 11 and HF driver 12. In these circuits, inductance L1 forms a resonance circuit with the transducer's capacitance at the transducer's thickness mode frequency and resistance R3 provides electrical damping.

On the receiving side, the circuits provide a current-to-voltage converter with the following properties: (1) an input electrical impedance that is close to zero; (2) an output impedance which is in resonance with the second matching circuit at the operating frequency of the acoustic transducer; and (3) an output resistance that is close to zero.

In practice, the circuitry of FIGS. 10 and 11, when used as part of the overall systems of FIGS. 2–5 and 6–9, allows time propagation measurements to be made at high frequencies for a variety of gas mixtures encountered in practice. In particular, this circuitry works successfully for signal amplitude ranges of up to 30 dB and signal-to-noise ratios of at least 30–40 dB. Circuitry other than that shown in these figures can, of course, be used in the practice of the invention. Similarly, the invention can be implemented using overall circuit configurations and acoustical cell structures other than those shown in FIGS. 2–5 and 6–9.

(2) Analog Signal Processing

FIG. 12 shows a series of time tracings identified by the letters A through K which occur at various locations in the block diagrams of FIGS. 2 and 6 during use of the apparatus of these figures (see the circled letters A through K in FIGS. 2 and 6). In this figure, tracing A shows the electrical waveform applied to piezoelement 40 and tracing B shows a typical output voltage waveform of preamplifier 17 during one frame, where, for purposes of illustration, signal 81 has been chosen as the first received signal and signal 82 as the second received signal.

In order to provide an accurate measurement of propagation time, one needs to measure the time interval between the same reference points of the envelopes of two chosen received signals. Because analog processing circuits, such as full-wave rectifiers, peak detectors, comparators, and the like, are most accurate when the signals are near full scale, the achievement of high accuracy time measurements is in general only possible if the signals being compared have similar amplitudes. The received signals for an acoustical propagation time measurement, however, are typically significantly different, a ratio logarithm of 20–40 dB being not uncommon; that is, because of the acoustical absorption of a gas medium, each successive received signal is typically 20–40 dB down from the preceding one. Tracing B of FIG. 12 illustrates the problem where it can be readily seen that the amplitudes of the first chosen received signal 81 and the second chosen received signal 82 are not at all close.

In accordance with the invention, this problem is addressed and solved by using time gain control circuit 18, which approximately equalizes the amplitudes of the signals from the output of preamplifier 17. The output voltage of the time gain control circuit 18 is applied to amplifier 19. The output from this amplifier for one measurement frame is shown in tracing C of FIG. 12, where reference number 83 represents the first chosen received signal and reference number 84 represents the second chosen received signal, in each case after processing by time gain control circuit 18 and amplifier 19.

As mentioned above, to achieve precise amplitude and time measurements it is necessary to detect the same reference points of the envelopes of two chosen received signals. This function is fulfilled by linear full-wave rectifier 20 of FIGS. 2 and 6, together with low-pass filter 21. The resulting typical voltage waveform during one frame is shown in tracing D of FIG. 12, where reference numbers 85 and 86 represent the normalized envelopes of the first chosen received signal and the second chosen received signal, respectively, after rectification and low-pass filtering.

Processing of the output voltage of low-pass filter 21 is performed by first strobed peak detector 22 and second strobed peak detector 23. In particular, first strobed peak detector 22 selects the envelope of the first chosen received signal 85 and detects its peak when first strobe signal 87 of tracing E of FIG. 12 is active. Similarly, second strobed peak detector 23 selects the envelope of the second chosen received signal 86 and detects its peak when second strobe signal 88 of tracing F of FIG. 12 is active. Strobe signals 87 and 88 are generated by control circuit 10. Sampling conditions of both strobed peak detectors are activated at the beginning of each frame by a synchronizing pulse, also generated by control circuit 10.

The output signals of strobed peak detectors 22 and 23 are illustrated in tracings G and H of FIG. 12, respectively. These signals are applied to first sample and hold circuit 24 and second sample and hold circuit 25, respectively. The sampling conditions of both sample and hold circuits are activated by the falling edges of the corresponding strobes. First sample and hold circuit 24 and second sample and hold circuit 25 form DC voltages $kU_1$ and kU2 of tracing D of FIG. 12, where voltages $U_1$ and U2 are the amplitudes of the envelopes of the first received signal 85 and second received signal 86, respectively, and k is a coefficient (0<k<1), that should neither be very high because the steepness of the usable envelopes drops as k increases, causing higher instability of the measurements, nor very low to avoid noise problems. A preferred value for this coefficient is 0.5.

Voltages kU1 and kU2 are applied to the referent inputs of corresponding first strobed comparator 26 and second strobed comparator 27. To their control inputs are applied first strobe signal 87 and second strobe signal 88, respectively, and to their signal inputs is applied the output signal of low-pass filter 21. The application of first strobe signal 87 and second strobe signal 88 to the respective comparators achieves separation of the corresponding envelopes of chosen received signals 85 and 86.

First strobed comparator 26 generates the signal shown in tracing I of FIG. 12, while second strobed comparator 27 generates the signal shown in tracing J. The signal from first strobed comparator 26 sets flip-flop 28, which is then reset by the signal of second strobed comparator 27. The duration of the flip-flop output pulse, shown by tracing K of FIG. 12, precisely represents the actual time interval between two chosen signals, as is desired.

For an echo format and the representative tracings of FIG. 12, the time interval between the beginning of a transmitted signal and the reference point of the first chosen received signal can be written:

$$t_{r1} = \Delta t_t + 2t + \Delta t_r \tag{14}$$

where $\Delta t_t$ is the total delay time during transmitting, which includes a time delay in the electronic transmission circuit and an acoustic time delay of the sound wave between the surface of the piezoelement and the emitting surface of the multilayer acoustical transformer; t is the time of acoustic wave propagation between the emitting surface of the multilayer acoustical transformer and the reflecting surface, which is the same in both directions; and $\Delta t_r$ is the total delay time during receiving, which includes a time delay in the electronic receiving circuit and an acoustic time delay of the sound wave between the emitting surface of the multilayer acoustical transformer and the surface of the piezoelement.

Similarly, the time interval between the beginning of a transmitted signal and the reference point of the second chosen received signal can be written:

$$t_{r2} = \Delta t_t + 6t + \Delta t_r \tag{15}$$

Because we measure the time interval between the first and the second received signals and because those signals have the same electronic and acoustic paths, the time interval of the ffip-flop output pulse is:

$$t_{ff} = t_{r2} - t_{r1} = 4t \tag{16}$$

This formula shows that by using the above approach, we exclude systematic errors in time measurements, an important advantage of the invention. A similar analysis shows that the same is true for the shadow format embodiments of the invention which employ the time difference between two received signals at the receiving piezoelement.

The flip-flop output pulse is supplied to processing network 29, where its duration is converting to a digital form. A second input of processing network 29 is connected to temperature sensor 47 of FIGS. 3–4 and 7–8. In FIGS. 3 and 7, this sensor measures the temperature of diffuser 46, while in FIGS. 4 and 8, it measures the temperature of the body 31 of the acoustical cell. In each case, this measured temperature can be considered to be the same as the test gas temperature to, for example, 0.1° C.

It is important to recognize that the above approach, in contrast to prior art acoustic methods, excludes the possibility of systematic errors because the measured acoustical received signals have the same electronic and acoustic paths. This approach avoids the need for frequent recalibration, which is an important advantage of the invention. In addition, it also allows for accurate measurement of the distance between the transmitting and reflecting surfaces of the acoustical chamber, the details of which are discussed below.

(3) Digital Signal Processing

In some applications, it is necessary to measure the concentration of mixture of gases, e.g., a binary mixture, at low pressures or under onditions of high attenuation of the acoustical signal due to molecular relaxation effects. The foregoing analog signal processing approach has been found to provide insufficiently accurate time measurements at certain concentrations of such gas mixtures.

In particular, the analog signal processing approach has been found not to work successfully when the relaxation frequency of the mixture becomes close to the operating frequency of the acoustical sensor. The relaxation frequency of a binary mixture, in turn, has been found to be proportional to the volumetric concentrations of the components of the mixture.

The attenuation of a binary mixture of hydrogen and carbon dioxide as a function of concentration illustrates the problem. It is known that the molecular relaxation frequency of carbon dioxide at a pressure of 1 atm is around 20 kHz, while for hydrogen under the same conditions, this parameter is around 18 MHz. FIG. 13 shows the results of a computer simulation for a mixture of these two gases. In particular, this figure shows the increase in acoustical attenuation at 1 MHz due to molecular relaxation for a mixture of these gases at one atmosphere. The vertical axis in this figure is in attenuation units relative to an ideal gas with attenuation normalized to one. The horizontal axis shows the volumetric hydrogen concentration relative to the total volume of the mixture.

As can be seen in this figure, the peak molecular relaxation attenuation is predicted to occur at 5.7% of hydrogen in the total volume. At this ratio, assuming a distance of 15 mm between transmitter and receiver, the signal should drop approximately 900 times compared to the situation where molecular relaxation is not present, i.e., the peak attenuation is nominally 900 times larger than the classical attenuation predicted by the Stokes-Kirchhoff model. Experimental results confirmed these theoretical calculations both in terms of relaxation frequency and relaxation strength.

An example of a recorded signal for the above mixture, which was obtained using an A/D converter connected to a computer, is shown in FIG. 14. As is evident, the received pulse is completely covered by noise. Under these circumstances, the above analog signal processing approach gives inaccurate results and instead the following digital signal processing procedures are employed.

In overview, the digital signal processing procedures of the invention were obtained by first theoretically establishing the optimal performance of the system, using the mean square error (MSE) of the estimates as the performance criterion, and then deriving methods which achieve or approach this performance level and which can be implemented in practice.

As discussed above, the problem of acoustically measuring the concentration of a gas mixture is one of estimating the time between any two received echoes or, alternatively, between a transmitted acoustical signal and the nth received signal. This in turn is equivalent to the problem of estimating time delay. Lower bounds for time delay estimation have been published by Zeira and Schultheiss. See Ariela Zeira and Peter M. Schultheiss, Realizable Lower Bounds for Time Delay Estimation, IEEE Transactions on Signal Processing, Vol. 41, No. 11, November 1993; and Ariela Zeira and Peter M. Schultheiss, Realizable Lower Bounds for Time Delay Estimation: Part 2—Threshold Phenomena, IEEE Transactions on Signal Processing, Vol. 42, No. 5, May 1994.

Figure 15:
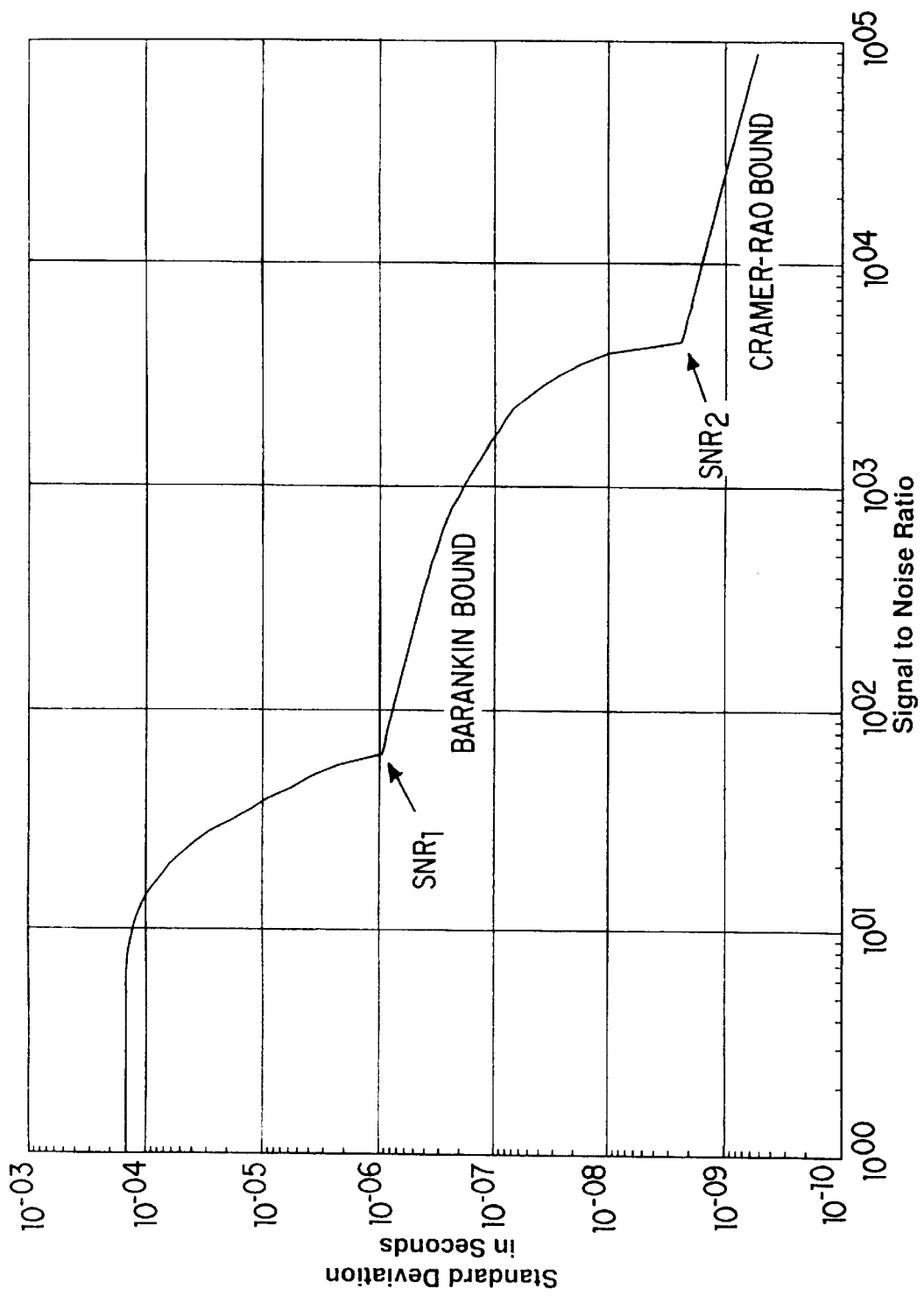
FIG. 15 is a plot of standard deviation in seconds versus signal to noise ratio as defined by Zeira and Schultheiss. It illustrates the realizable lower limits on an unbiased estimator's ability to estimate time delay as a function of signal to noise ratio.

As shown by Zeira and Schultheiss, the lower bounds for time delay estimation divide the domain of signal to noise ratios into several disjointed segments separated by thresholds as shown in FIG. 15. For extremely low signal to noise ratios (SNR), the plot of standard deviation of delay estimation as a finction of SNR is essentially flat. As the SNR increases, a threshold is encountered ($SNR_1$) at which the standard deviation drops to a new, lower value. For $SNR>SNR_1$, the plot of standard deviation versus SNR assumes a straight line with negative slope. This segment defines the domain of SNR governed by the Barankin bound (BB). At still higher SNR a second threshold is encountered ($SNR_2$), where the standard deviation drops again to yet a lower bound, the Cramer-Rao lower bound (CRLB), which is a special case of the Barankin bound. The CRLB is also a straight line with a minus one slope. These bounds define the lower limit on any estimator's ability to estimate time delay.

The CRLB for a single echo (or multiple echoes each separated by several signal correlation times) is $$\sigma^2 = \frac{1}{\omega^2 SNR} \tag{17}$$

where ω is the signal frequency and $$SNR = \frac{E}{\pi N_0} \tag{18}$$

where E is the total signal energy $$E = \int_{-\infty}^{\infty} s^2 \, dt \tag{19}$$

and $N_0$ is the spectral power density of the noise $$N_0 = \frac{\sigma_n^2}{2\pi W} \tag{20}$$

where $\sigma_n^2$ is the noise variance and W is the Nyquist bandwidth of the noise.

The Barankin bound BB for a single echo (or multiple echoes each separated by several signal correlation times) is $$\sigma^2 = \left(\frac{1}{\beta^2} + \frac{1}{\omega^2}\right)\frac{1}{SNR} \tag{21}$$

where β is the bandwidth of the signal, defined as $$\beta^2 = \frac{\int_{-\infty}^{\infty} (\omega - \omega_0)^2 |S(\omega)|^2 \, d\omega}{\int_{-\infty}^{\infty} |S(\omega)|^2}$$

here S(ω) is the Fourier transform of the signal s(t).

The BB region intersects the CRLB at $$SNR_2 = \frac{\omega^2}{\beta^2} \tag{22}$$

At the lowest SNR levels the plot becomes horizontal at a standard deviation value of $$\sigma = \frac{\text{Range of Search}}{\sqrt{12}}$$

This value results from the estimator's inability to find the correct peak such that the probability density finction becomes uniform over the allowed range of search. Such a uniform probability density function has the following statistical properties $$\bar{x} = \int_0^a \frac{x}{a}dx = \frac{a}{2} \quad \text{and} \quad \overline{x^2} = \int_0^a \frac{x^2}{a}dx = \frac{a^2}{3}$$

thus giving the above value for $\sigma$ $$\sigma^2 = \overline{x^2} - (\bar{x})^2 = \frac{a^2}{12} \tag{23}$$

The Barankin and Cramer-Rao bounds do not tell one how to construct an estimator. Rather, they simply place a lower limit on the performance of any estimator.

Equation (17) states that if the signal to noise ratio is held constant, then it is theoretically possible for an estimator to do a progressively better job as the signal frequency increases. However, from equation (11), the acoustical attenuation of a gas increases with frequency as $$e^{Af^2 L_p}$$

$$\left(\text{where } A = \frac{\alpha}{f^2}\right),$$

which can lead to a significant reduction of SNR even if great care is taken in the design of the electrical and mechanical coupling between the sensor system and the gas mixture as described herein.

Equation (22) states that the location of the transition region which separates the CRLB from the BB is proportional to $\omega^2/\beta^2$. Accordingly, the region governed by the lower and thus more desirable Cramer-Rao bound can be extended to lower SNR levels, i.e., to the left in FIG. 15, by increasing the bandwidth of the signal.

In their development of realizable lower bounds for time delay estimation, Zeira and Schultheiss defined signal to noise ratio and signal energy as shown above in equations (18) and (19), respectively. Zeira and Schultheiss' choice of SNR results in certain invariances with changes in signal energy due to the fact that their definition requires that the spectral noise level track the signal energy when SNR is held constant. This can lead to false conclusions when ranking different delay measurement methods.

For example, it would be unusual to find a real situation where the noise level increased along with signal energy, but Zeira and Schultheiss' SNR definition implicitly assumes this to be the case. A direct application of this definition would lead to the incorrect conclusion that increasing the duration of the signal produces no benefit in terms of extending operation to lower signal levels. For acoustical gas concentration measurements, the dominant contributors to system noise are thermal noise associated with the piezoceramic element and the preamplifier input. Both these noise sources are essentially independent of the signal energy; thus, for this application, increasing signal duration (energy) will, other things being held equal, reduce the standard deviation of the measurement. For these reasons, the definition of SNR employed by Zeira and Schultheiss is used herein only as a standard against which to compare the performance of the concentration estimator of the present invention to the CRLB.

For purposes of the present invention, the SNR is defined as $$SNR = \frac{\sigma_{signal}}{\sigma_{noise}}$$

In practice, this definition yields more insightful conclusions when evaluating simulation results for different signal lengths (i.e., number of cycles) and sampling rates for an acoustical concentration sensor.

The key variables involved in choosing the number of cycles to use in a particular application are: anticipated signal to noise ratio which depends on the acoustical attenuation of the gas mixture being tested and processing throughput requirements. Basically, for a given noise level, the more signal energy, i.e., the more cycles, the smaller the standard deviation of the measurement.

To aid in comparing numerical simulation results with the analytical results of Zeira and Schultheiss, their results can be rewritten in terms of a sampled data system as follows:

$$E = \frac{1}{f_s}\sum_{k=1}^{K} s_k^2(t) \text{Watt} \cdot \text{sec} \quad \text{and} \tag{24}$$

$$N_0 = \frac{\sigma_n^2}{2\pi \frac{f_s}{2}} = \frac{\frac{1}{N}\sum_{n=1}^{N} n_n^2(t)}{2\pi \frac{f_s}{2}} \frac{\text{Watt} \cdot \text{sec}}{\text{rad}} \tag{25}$$

where $f_s$ is the sampling frequency and $1/f_s$ is used to convert from units of samples to seconds. Conversion from "samples" to "seconds" helps avoid reasoning errors in system design using statistical methods. In the discussion below, the standard deviation and variance of the delay estimation error are thus given in units of seconds not samples. Also, a one watt load is implicitly assumed so that spectral power density can have the units of watts.

Substituting equations (24) and (25) into the equation for SNR and simplifying we have $$SNR = \frac{\frac{1}{f_s}\sum_{k=1}^{K} s_k^2(t)}{\pi \frac{\frac{1}{N}\sum_{n=1}^{N} n_n^2(t)}{2\pi \frac{f_s}{2}}} = \frac{\frac{1}{f_s}\sum_{k=1}^{K} s_k^2(t)}{\frac{1}{f_s N}\sum_{n=1}^{N} n_n^2(t)} = \frac{\sum_{k=1}^{K} s_k^2(t)}{\frac{1}{N}\sum_{n=1}^{N} n_n^2(t)} \tag{26}$$

Substituting this expression for SNR into Zeira's CRLB equation yields $$\sigma_{CRLB}^2 = \frac{1}{\omega^2 SNR} = \frac{\frac{1}{N}\sum_{n=1}^{N} n_n^2(t)}{\omega^2 \sum_{k=1}^{K} s_k^2(t)} \tag{27}$$

According to this relationship, the Cramer-Rao lower bound on the variance of estimated delay error is related to the constituent parameters as follows:

$$\sigma_{CRLB}^2 \approx \frac{1}{\omega^2} \quad n_n^2, f_s, s_k^2, R_s(0) \text{ constant} \quad (28)$$

$$\sigma_{CRLB}^2 \approx \sigma_n^2 \quad n_n^2, \omega, f_s, R_s(0) \text{ constant} \quad (29)$$

$$\sigma_{CRLB}^2 \approx \frac{1}{R_s(0)} \quad n_n^2, \omega, f_s, s_k^2 \quad \text{constant} \quad (30)$$

where $R_s(0)$ is the auto-correlation value when the two waveforms are in perfect alignment:

$$\left(\sum_{k=1}^{K} s_k(t) \times s_k(t+\tau)\right)\bigg|_{\tau=0} = \sum_{k=1}^{K} s_k^2(t) = R_s(0) \quad (31)$$

Several key observations can now be made: (1) from equation (28), it is seen that the theoretical lower bound on standard deviation for a delay estimator is inversely proportional to the signal frequency, assuming SNR remains unchanged; (2) from equations (26) and (27), it is seen that the theoretical lower bound on standard deviation for a delay estimator is inversely proportional to the square root of the duration of the signal assuming the standard deviation of the noise remains unchanged; and (3) from equation (22), it is seen that the location in the SNR domain of the CRLB to BB threshold is inversely proportional to the signal bandwidth. At first glance it might seem that observations 2 and 3, longer signal duration and wider bandwidth, are at odds with one another. However, this seeming conflict is overcome in accordance with the invention by frequency modulating the transmitted acoustical signal as discussed below.

Maximum-likelihood estimation is an appropriate choice for the problem of estimating the concentration of a gas mixture. Since one does not want to assign unmeaningful a priori distributions to the unknown parameters, Bayes estimation is not applicable. Also, since one does not know the relationship of the parameters to the moments of the sample vector, the method of moments is not appropriate. Maximum-likelihood (ML) estimation was developed by Fisher in 1912. See Fisher, R. A., On an Absolute Criterion for Fitting Frequency Curves, Mess. of Math., 41, pp. 155–160, 1912. ML estimation is treated in detail by Van Trees. See Van Trees, Harry L., Detection, Estimation, and Modulation Theory, Part 1., John Wiley & Sons, Inc., New York, 1968.

Some of the known general properties of ML estimates are as follows:

(1) An efficient estimator is one whose variance equals the CRLB. If an efficient estimate $\hat{\tau}$ of $\tau$ exists, Cramer showed that the likelihood equation will have a unique solution equal to $\hat{\tau}$. See Cramer, H., Mathematical Methods of Statistics, Princeton University Press, 1946.

(2) Under certain general conditions the likelihood equation has a solution $\hat{\tau}$ that converges in probability to $\tau$ as $N \to \infty$. This solution is an asymptotically normal and efficient estimate of $\tau$.

(3) ML estimators of delay, when noise is additive, are asymptotically unbiased as $SNR \to \infty$.

The ML estimator for delay estimation calculates the sample cross correlation between the received signal and a noise free replica of the received signal, which with some restrictions could be a replica of the transmitted signal. The ML estimate is the location of the absolute maximum of the sample cross-correlation. See Zeira, A, Realizable Lower Bounds for Time Delay Estimation, Ph.D. dissertation, Yale University, New Haven, Conn., 1991.

For a sampled data system cross-correlation takes the form $$z(n) = \sum_{m=0}^{N-1} x(m) y(n+m) \quad (32)$$

A direct implementation of equation (32) leads to two major difficulties. First, equation (32) is computationally intensive. For example, for a transmitted signal consisting of sixteen cycles of a 1 MHz waveform, a 32 MHz sampling frequency, a 15.35 mm separation between the transmitter and receiver (representing a search range of nominally 100 microseconds), and no a priori knowledge of the approximate location in time of the received signal, the search range is 3200 samples. The resulting processing burden entails multiplying a 512 element stored replica vector by a 512 segment of the received signal and repeating this process 3200 times as the replica vector is stepped along the received signal vector. This equates to 1.64 million floating point multiplications and additions per measurement which, at 1000 measurements per second, represents well over a billion floating point multiplications and additions per second. A solution to this computational problem employing Fast Fourier Transforms is described below.

A second disadvantage is the appearance of the signal to noise thresholds theoretically predicted by Zeira and Schultheiss for any unbiased estimator. Thus, the CRLB becomes equivalent to the BB with regard to standard deviation for a transmitted signal that consists of a single pulse having a shape identical to the envelope of a transmitted high frequency signal. At still lower SNR, the BB in turn encounters a threshold where it becomes impossible to detect even the envelope. At this point, the probability of the estimator finding a peak is equally likely over the entire range of the search and the slope of the plot becomes zero at a constant standard deviation as set forth above in equation (23).

FIGS. 16 and 17 illustrate in practical terms the consequences of the threshold effect for the cross-correlation ML estimator of the invention. In particular, these figures illustrate the effects of the $SNR_2$ threshold.

FIG. 16A shows a noise free, windowed (see below), 16 cycle signal with no noise; FIG. 16B shows the cross correlation function with the central peak located at sample number 613 for the noise free signal of FIG. 16A; FIG. 16C shows the central peak of FIG. 16B for an expanded horizontal scale. From these figures, it can be seen that although the location of the peak of the cross correlation function is unambiguous, the amplitude of the two nearest side peaks is close to the amplitude of the true center peak.

As the signal to noise ratio decreases, a point is reached where the amplitude of one of the two side peaks will occasionally exceed that of the true center peak and the wrong peak will be chosen resulting in a large measurement error. FIG. 17 shows an example of this situation. The only difference between FIGS. 16 and 17 is that in FIG. 17 an amount of noise was added to the received signal prior to the correlation operation so as to ensure that the wrong peak was chosen. As in FIG. 16, the true central peak is located at sample number 613, but as illustrated in FIGS. 17B and 17C, due to a low signal to noise level, the correlation peak immediately to the right of the correct peak has a slightly larger amplitude and will be chosen by the cross-correlation estimator.

In accordance with the invention, this problem is overcome by frequency modulating the transmitted signal. From FIG. 15, it can be seen that the performance of the ML estimate can be improved by shifting the location of the $SNR_2$ threshold to lower signal to noise ratios, i.e., to the left in this figure. Equation (22) states that theoretically such a shifting can be accomplished by increasing the bandwidth of the signal. Signal bandwidth can be increased by shortening the duration of the signal, e.g., by using a four cycle signal rather than a 16 cycle signal, however this strategy would lower signal energy and in turn increase the standard deviation of the measurement in the CRLB domain of SNR.

In accordance with the invention, it has been determined that a far more productive approach to increasing bandwidth is to frequency modulate the signal in which case signal duration (energy) and bandwidth are decoupled and the benefits of higher signal energy and wider bandwidth can be realized simultaneously.

From the above discussion of the $SNR_2$ threshold in terms of the misidentification of a sidelobe as having the maximum correlation, it follows that if signal modulation shifts the FIG. 15 $SNR_2$ threshold to the left, i.e., to a lower SNR value, then the amplitude of the correlation sidelobes relative to the center peak should be reduced by such modulation. FIG. 18 shows that this is the case.

In particular, FIG. 18 shows the results of a 0.2 modulation of the carrier frequency for the case of no noise, i.e., the 1 MHz carrier was swept from 0.8 MHz to 1.2 MHz in nominally 16 microseconds along the linear trajectory (frequency modulation vector) shown in FIG. 19A. (A sinusoidal trajectory can also be used, but a linear trajectory is preferred.) Comparing FIGS. 18B and 18C to FIGS. 16B and 16C it can be seen that modulating (sine chirping) the transmitted signal yields a substantial decrease in sidelobe amplitude relative to the center peak.

FIGS. 19B and 19C shows the cross-correlation function of a frequency modulated 16 cycle signal where the same noise vector used in FIG. 17 has been added to the received signal. Comparison of these figures with FIGS. 17B and 17C show that by means of the modulation, the correct peak has the largest amplitude and will be chosen, as is desired.

That the $SNR_2$ threshold is shifted to a lower SNR value by frequency modulating the transmitted signal is shown in FIGS. 20 and 21. FIG. 20 plots the standard deviation verses SNR (Zeira and Schultheiss definition) for the ML estimator operating on a 32 cycle unmodulated signal together with the plot of the realizable lower bound originally shown in FIG. 15. As can be seen in this figure, the ML estimator of the invention attains the realizable lower bounds for time delay estimation.

The results of a 0.2 frequency modulation are shown in FIG. 21, where again the standard deviation verses SNR (Zeira and Schultheiss definition) is plotted. As shown in this figure, the location of the $SNR_2$ threshold for the modulated signal is shifted to the left to the approximate position of the $SNR_1$ threshold.

Each of the data points plotted in FIGS. 20 and 21 is the standard deviation computed from 1000 measurements at each SNR value. The sampling rate used in these calculations was 32 samples/cycle and the signal range was $2^{14}$ samples.

The amount of modulation that can be employed is constrained by the bandwidth of the electromechanical subsystem comprising (1) the electronic amplifiers, (2) the impedance matching electrical circuits, (3) the piezoceramic transducer and (4) the acoustical impedance matching layers (see below). Signal energy outside the pass band of this electromechanical system is not coupled into the gas.

A simplified lumped parameter model of a piezoceramic transducer and the impedance matching layers discussed below comprises a fourth order Butterworth filter with a 3 dB bandwidth of 400 kHz and a center frequency of 1 MHz. A number of modulation waveforms were evaluated in an effort to arrive at an optimum FM modulation waveform. For acoustical concentration measurements, the optimum FM waveform represents a compromise between a large change in frequency with the attendant suppression of the cross-correlation side peaks on one hand and the bandwidth limitations of the piezoceramic transducer and impedance matching layers on the other. In practice, a modulation factor of 0.2 has been found to provide an excellent compromise, although other modulation factors can of course be used if desired.

FM modulation allows the use of long signals where the duration of the signal greatly exceeds the round trip signal propagation of the acoustical chamber (the "wraparound time"). In this case the signal seen by the receiver electronics is the sum of two or more received signals, i.e., the first received signal, the second received signal, etc., where each successive received signal is delayed by a time equal to the round trip signal propagation of the acoustical chamber. FIG. 22 provides an example of such a signal assuming a 22 $\mu$sec round trip propagation time (assumes pure hydrogen C =1400 m/sec and round trip path length of =31 mm). The transmitted signal shown in FIG. 22A is a nominal 256-cycle signal with a center frequency of 1 MHz and a 0.2 frequency modulation. The signal's total duration is 256×1 $\mu$sec=256 $\mu$sec, or 8192 samples assuming a sampling rate of 32 MHz. FIG. 22B shows the resulting signal when the signal of FIG. 22a is added to a delayed (22 $\mu$sec) and attenuated (0.5×) copy of itself. The attenuation factor of 0.5 approximates the absorption of the gas, but has no effect on the ML estimator's ability to separate the two signals. FIG. 22C shows the resulting cross-correlation function and the two peaks clearly resolved and separated by 704 samples, which equals 22 $\mu$sec.

It should be noted that in the case of a single transducer implementation where the transducer is used for both transmitting and receiving, the length of the transmitted signal should remain less than the wraparound time, because the very high amplitude of the transmitted signal will typically saturate the receiver electronics so that the return signal cannot be detected.

As previously mentioned, the direct implementation of the ML estimator requires something on the order of 1.64 million floating point multiplications and additions per measurement. The apparatus of the invention is capable of generating nominally 1,000 transmit/receive frames per second, which if fully utilized, requires that the 1.64 million arithmetic operations be completed in 1/1000 of a second. Equivalently, one floating point multiply and add must be completed in 0.6 nanoseconds ($0.6 \times 10^{-9}$ seconds).

This level of performance can be achieved with high cost computing equipment of the type used for military and/or aerospace applications where price sensitivity is low. However, this performance level is well beyond the capability of currently available low cost digital signal processors which are suitable for price sensitive industrial applications. The invention addresses and solves this problem by using Fast Fourier Transform (FFT) techniques to calculate the required cross-correlations as follows.

Let x(n) and y(n) be two periodic sequences of period N with their Discrete Fourier Series denoted by X(k) and Y(k), respectively:

$$X(k) = \sum_{m=0}^{N-1} x(m)e^{-2\pi jmk/N} \qquad (33)$$

$$Y(k) = \sum_{r=0}^{N-1} y(r)e^{-2\pi jrk/N} \qquad (34)$$

If we multiply the series X(k) with the conjugate of Y(k), we have $$X(k)Y^*(k) = \sum_{m=0}^{N-1}\sum_{r=0}^{N-1} x(m)y(r)e^{-2\pi j(m-r)k/N} \qquad (35)$$

If we then take the Inverse Discrete Fourier Series of the product, we have:

$$z(n) = 1/N \sum_{k=0}^{N-1} X(k)Y^*(k)e^{2\pi jkn/N} \qquad (36)$$

$$= \sum_{m=0}^{N-1} x(m) \sum_{r=0}^{N-1} y(r) \left[ 1/N \sum_{k=0}^{N-1} e^{2\pi jk(n-m+r)/N} \right]$$

Considering z(n) for $0 \leq n \leq N-1$, we have:

$$1/N \sum_{k=0}^{N-1} e^{2\pi jk(n-m+r)} = \begin{cases} 1, & \text{for } r = (n+m) + cN \\ 0, & \text{otherwise} \end{cases} \qquad (37)$$

where c is any integer. This results in:

$$z(n) = \sum_{m=0}^{N-1} x(m)y(n+m) \qquad (38)$$

which is equivalent to the cross-correlation of x(n) and y(n) given in equation (32).

A direct implementation of equations (33) through (36) would increase the amount of computation compared to a direct cross-correlation by slightly more than a factor of two. However, the Discrete Fourier Series x(n) and y(n) and the Inverse Discrete Fourier Series of the product can be efficiently computed using a Fast Fourier Transform (FFT) algorithm.

Evaluation of the N samples by direct correlation requires a computation time proportional to $N^2$, the number of multiplications. Similarly, a direct implementation of equations (33) through (36) requires a computation time proportional to $N^2$ for each equation. However, with the FFT, the computational time to compute a Fourier series is proportional to $N\log_2(N)$, a considerable savings. Using the FFT, the total computational time to compute two Fourier series, followed by one vector multiplication, and finally another FFT for the inverse transform is proportional to $3N\log_2(N)+N$. However, the FFT of the transmitted waveform, equation (34), can be precomputed so as to reduce the run time processing to $2N\log_2N)+N$.

Exactly how much faster the FFT approach is compared to the direct correlation approach depends not only on the number of samples in the signal and the length of the received frame, but also on the efficiency of the FFT and cross-correlation programs employed. A suitable algorithm for performing FFTs is that set forth in Sorensen et al., Real-valued algorithms for the FFT Proceedings: ICASSP 87, 1987 International Conference on Acoustics, Speech, and Signal Processing (Cat. No. 87CH2396-0), p. 2425 vol. 4, pp. 1831–4, vol. 3.

Computational experiments have shown that it is faster to employ the FFT approach if N exceeds 64. Benchmarking on a PC has shown that for the case of a 512 sample transmitted waveform and a 3200 sample received signal, the FFT approach will be approximately 60 times faster than direct correlation.

To minimize biasing of the maximum likelihood estimate due to the finite extent of the transmitted waveform (i.e., its truncation with a rectangular window), the amplitude of the leading and trailing data points are preferably gradually reduced to zero by a process known as windowing. FIG. 23 shows an unwindowed 16 cycle, 0.2 frequency modulated signal (FIG. 23A) and its frequency spectrum (FIG. 23B), which is seen to contain significant side lobe energy well away from the center frequency of the transmitted signal, i.e., the frequency spectrum of the unwindowed signal exhibits "ringing".

To reduce these side lobes, the signal vector is multiplied by the window vector shown in FIG. 24A. The resulting windowed waveform eLs shown in FIG. 24B is the data vector used to create the transmitted signal by means of, for example, a digital to analog converter (see FIG. 25). FIG. 24C shows the frequency spectrum of the windowed 16 cycle, 0.2 frequency modulated signal. The elimination of the spurious side lobes is evident in this figure.

A further precision improving feature of the invention is to perform a parabolic fit using the largest amplitude cross-correlation value and the two adjacent values. Using the equation $y=at^2+bt+c$, the coefficients a, b, and c are determined using the three largest cross-correlation values. The first derivative of y, i.e., y'=2at+b, is then set equal to zero and solved for t, the location of the peak (maximum) correlation.

FIG. 25 sets forth a block diagram of suitable hardware for implementing the digital signal processing aspects of the invention. DSP (digital signal processor) 104 of this figure is preferably a 32-bit floating point processor. In operation the desired transmitted waveform, e.g., a windowed, frequency-modulated waveform, is generated by a computer program and stored as a sequence of floating point numbers in a data file. The digital signal processor 104 reads in this data file and stores the data points in FIFO (first-in-first-out) buffer 103. The data are then sequentially outputted to D/A (Digital-to-Analog) converter 102 to generate an analog waveform corresponding to the computer generated waveform. This analog waveform is then sent through transmitter 101 of the acoustic sensor into the gas medium. Transmitter 101 is preferably of the type discussed above in connection with the analog signal processing embodiments of the invention.

After propagation through the gas medium, the acoustical signal is detected by receiver 105 and digitized by A/D (Analog-to-Digital) converter 106 to a sequence of floating point numbers (see FIG. 26A). Receiver 105 is preferably separate from transmitter 101 especially when weak signals are expected, although a combined transmitter/receiver can be used if desired. Receiver 105 is preferably of the type discussed above in connection with the analog signal processing embodiments of the invention.

The numbers generated by A/D converter 106 are first stored in dual port memory 107 and then read by the digital signal processor. Thermistor 109 together with signal conditioning circuitry 110 is used to measure the temperature of the gas. A second A/D 111 is used to convert the temperature to a floating point number suitable for processing by the digital signal processor. Thermistor 109 is preferably of the type described above in connection with the analog signal processing embodiments of the invention. Multiple thermistors can be used if desired.

FIGS. 26 and 27 illustrate the measurement of the time component of the speed of sound determination from the digitally recorded data obtained using the apparatus of FIG. 25. In particular, these figures illustrate this measurement for the case of a shadow format, analogous procedures being applicable to an echo format.

FIG. 26A shows a typical received acoustical signal as recorded at the receiver, which in this case consists of a direct path signal and two successive echo signals. A cross-correlation, preferably using the above described FFT techniques, is performed between a stored template signal, described below, and the received signal. This cross-correlation procedure produces correlation peaks for the direct path signal and the two successive echo signals as shown in FIG. 26B. In this figure, $t_1$ identifies the correlation peak for the direct path signal and $t_2$ identifies the peak for the first echo signal.

The various time components making up $t_1$ and $t_2$ are shown in FIG. 27, where $t_{trans}$ and $t_{rcve}$ represent the delays associated with the transmitter and receiver electromechanical circuitry, respectively, and $T_p$ is the time for the acoustical signal to propagate the distance L through the gas medium. By determining the time delay between the first and second correlation peaks, i.e., $t_2-t_1=2T_p$, the speed of sound $C_M$ in the mixture can be determined from the equation:

$$C_M = \frac{2L}{t_2 - t_1}$$

In applications where high acoustical absorption is encountered, such as at partial vacuums or in the presence of molecular relaxation, the signal to noise ratio of the second received signal (first echo signal in FIG. 26A) may be too low to yield useful results. In these cases, only the first correlation peak is used in conjunction with a stored delay parameter τ. Under these circumstances, the time interval $T_p$ between the transmitted signal and the first correlation peak is calculated by subtracting τ from $t_1$ (see FIG. 27). Tau represents the delay of the transmit and receive electromechanical circuitry and is measured as part of the calibration process for the system (see below).

Sensor calibration is a three step process. The first step involves measuring and storing the stray path interfering signal that reaches the receiver by means of the acoustical path provided by the body of the sensor. To accomplish this, the interior of the sensor is placed under a vacuum, typically less than one Torr, such that the amplitude of the direct path received signal is effectively zero. The resulting received signal can therefore be attributed to transmitted acoustical energy which took the stray path through the sensor body plus background noise of the sensor system, which is assumed to be white Gaussian noise (zero mean). In order to suppress the noise contribution to the calibration measurement, many (e.g., a 100 or more) waveforms are collected and added on a sample by sample basis and then normalized by dividing the resulting composite received signal vector by the number (e.g., 100) of collected waveforms. The resultant averaged stray path signal is recorded and stored as a floating point vector in, for example, non-volatile memory 108 of FIG. 25. In operation, the stored stray path signal vector is subtracted from the received signal prior to analysis of that signal by, for example, the FFT procedures described above.

The stray path subtraction operation effectively reduces the stray path component of the received signal by a factor of about ten. Although the stray path signal is stationary with respect to concentration changes, under real operating conditions cancellation is not perfect due to small changes in the speed of sound in the sensor body resulting from changes in temperature and stress. The stored stray path vector is unique to each sensor. Stray path signal cancellation is most important in the case of low amplitude received signals that are typically encountered when operating at low pressures or under conditions of increased absorption due to molecular relaxation effects, but can be used in other cases if desired. Also, stray path cancellation is more important in cases where the body of the sensor is composed of metal, e.g., stainless steel, as opposed to plastic, e.g., PVDF, but can be used in all cases if desired.

The second calibration step is to calibrate the fixed delay $t_{trans}$ and $t_{rcve}$ of the transmit and receive electromechanical circuitry. Like stray path cancellation, the latter are used typically in applications having high signal attenuation where the second received signal (first echo signal in FIG. 26A) may have too low a signal to noise ratio to provide useful results. This calibration also provides the template waveform which is used in the cross-correlation procedure.

In this calibration step, an ideal gas such as argon is used at standard temperature and pressure. Under these conditions, the speed of sound is known to a high precision and both the first and second received signals (i.e., the direct path and first echo signals in FIG. 26A) have sufficiently high signal to noise ratios to be accurately detected. Numerous waveforms (e.g., 100) are collected and added on a sample by sample basis and normalized by dividing the composite received signal vector by the number (e.g., 100) of collected waveforms.

The template waveform is then calculated by computing the FFT of the composite received signal vector, after having set the amplitude of all but the first received signal (i.e., the direct path signal) to zero. Because the composite received signal is a sample by sample average of a large number of waveforms, the beginning and end of the direct path signal can be identified as those points adjacent to the direct path signal where the composite received signal effectively has a zero amplitude relative to its amplitude during the direct path signal. If the bandwidth of the transducer and impedance matching layers were sufficiently wide, the template waveform would be identical to the FFT of the transmitted signal, but as it is not, the template waveform is needed for optimum performance. The transfer function of the sensor is calculated from the template waveform by dividing that waveform by the FFT of the transmitted signal.

The template waveform is then cross-correlated with the composite received signal vector. Mathematically, this can be considered to be an auto-correlation for the first reflection (the direct path signal) and a cross-correlation for the second reflection (the first echo signal). The first two peaks of the correlation results are found giving $t_1$ and $t_2$. The delay τ through the transmitter and receiver can then be found from the following equation (see FIG. 27):

$$\tau = t_{trans} + t_{rcve} = \frac{3t_1 - t_2}{2}$$

The last step of the calibration involves determining the exact path length L of the sensor. This step is discussed below under the heading "Accurate Measurement of the Distance Component of the Speed of Sound Determination."

The FFT of the template waveform, the delay τ, and the path length L are unique to each sensor. These values are stored in, for example, the sensor's non-volatile memory 108 of FIG. 25 and are retrieved and used during the operation of the apparatus.

(4) Acoustical Transformer Design

As discussed above, the operating surface of the one or more piezoelements used in the acoustical sensor is acoustically matched with the test medium by means of a broadband and high efficiency multilayer acoustical transformer.

For optimum coupling, the thickness of each layer of the transformer should be approximately equal to the speed of sound in the layer divided by four times the operating acoustical frequency of system. Also, the acoustical impedance (resistance) of each layer should be approximately equal to the square root of the product of the acoustical impedances (resistances) on either side of the layer. For example, to achieve optimum coupling for a two layer system, the acoustical impedance of the layer which contacts the piezoelement should be approximately equal to the square root of the product of the acoustical impedance of the piezoelement and the acoustical impedance of the layer which contacts the gas, while the acoustical impedance of the layer which contacts the gas should be approximately equal to the square root of the product of the acoustical impedance of the gas and the acoustical impedance of the layer which contacts the piezoelement.

The above impedances (resistances) for the layers making up the acoustical transformer will result in a transformer that yields good coupling only over a very narrow range of frequencies, i.e., its transfer function can approach one at the center frequency, but falls off very steeply for small frequency deviations about the center frequency. As discussed above, in accordance with the digital signal processing aspects of the invention, the acoustical signal which needs to be transferred to and from the transducer(s) consists of a relatively few number of cycles (e.g., 4 to 256) combined with a nominal ±10% frequency modulation. As a result, the bandwidth of the signal is not particularly narrow.

Given this, it is advantageous to trade peak coupling efficiency for wider bandwidth. That is to say, a transformer structure that yields a broad flat transfer function is better than one that has peak efficiency. To implement such a broad band characteristic, the quarter wave and square root of the products rules are intentionally compromised. In particular, the transformer examples set forth below deviate from these rules in order to achieve a bandwidth which is more in keeping with the bandwidth of the acoustical signal.

As discussed above, the layer of the acoustical transformer which contacts the test medium needs to be inert to the constituents of that medium. For example, for a test medium which constitutes a binary mixture of dichloroethylene and nitrogen, the exposed layer of the transformer, as well as the body of the acoustical sensor, can be made from a fluoropolymer, e.g., a tetrafluoroethylene polymer such as PVDF. A suitable piezoelement/acoustical transformer construction in this case is:

(1) A piezoelement APC 850 manufactured by American Piezoceramics, Inc., Mackeyville, Pa., having a diameter of 1 inch (25.4 mm), a thickness of 0.08 inches (2.03 mm), and an acoustical resistance of $30.5 \times 10^6$ Pa·s/m. This transducer has a radial mode resonance frequency of approximately 80 kHz and a thickness mode resonance frequency of 1 MHz.

(2) An aluminum layer with a ¼ wavelength thickness of 1.58 mm and an acoustical resistance of $17.06 \times 10^6$ Pa·s/m.

(3) A PVDF layer with a ¼ wavelength thickness of 0.51 mm and an acoustical resistance of $3.6 \times 10^6$ Pa·s/m.

FIG. 28A is a plot of the squared transmission coefficient (or energy transmission coefficient) for the above transformer vs. frequency where the test medium is 37% by volume of dichloroethylene and 63% of nitrogen. This mixture has an acoustical resistance of 620 Pa·s/m. The coefficient plotted in FIG. 28A is calculated using the classical complex equations which describe the propagation of plane elastic longitudinal waves (see Elmore et al. "Physics of Waves", Dover Publications, Inc., NY, 1985). As can be seen in this graph, the relative bandwidth of the transformer is on the order of 50%, with total acoustical losses being around 55 dB.

For other applications, e.g., where the test medium is a binary mixture of phosphorus oxychloride and oxygen, the body of the sensor is preferably composed of stainless steel. For this case, a suitable transformer for use with the APC 850 piezoelement comprises the following layers:

(1) An aluminum layer with a thickness of 0.787 mm and an acoustical resistance of $17.06 \times 10^6$ Pa·s/m.

(2) An INCONEL 718 layer with the thickness of 0.1778 mm and an acoustical resistance of $45.1 \times 10^6$ Pa·s/m.

(3) A TEFLON layer with the thickness of 0.335 mm and an acoustical resistance of $2.8 \times 10^6$ Pa·s/m.

FIG. 28B shows the squared transmission coefficient for this transformer for a test medium of 18% by volume of phosphorus oxychloride and 82% of oxygen. This mixture has an acoustical resistance of 511 Pa·s/m. As can be seen in this graph, the relative bandwidth is on the order of 40%, with total acoustical losses being around 50 dB.

C. Accurate Measurement of the Distance Component of the Speed of Sound Determination After assembling the acoustical cell it is necessary to accurately measure the distance between the gas-contacting surface of the multilayer acoustical transformer and the reflecting surface in the case of an echo format or the distance between the gas-contacting surfaces of the two multilayer acoustical transformers in the case of a shadow format. Because direct access inside the acoustical chamber is impractical, an acceptably accurate (to several micrometers) alternative way to provide this measurement is to perform an acoustical measurement of propagation time t for a pure, preferably close to ideal, gas with known thermodynamic properties.

If it is assumed that t corresponds to the time difference between two received pulses, the length L can be determined from the following equation:

$$L = \frac{t}{2}\sqrt{\frac{\gamma z R T}{M}} \tag{39}$$

where γ and z can be calculated using formulas (2) and (8), respectively, and M is the molecular weight of the pure gas.

Alternatively, a gas and test conditions can be used for which the speed of sound is well-know, e.g., the gas can be argon at standard pressure and temperature. If the known speed of sound is $C_N$, the time of the first received signal is $t_1$, and the time of the second received signal is $t_2$, the desired distance L can be calculated from the formula:

$$L = \frac{C_N \times (t_2 - t_1)}{2}$$

Because of the possibility of chemical deposition within the chamber of the acoustical sensor, L is preferably redetermined periodically, e.g., once every several months or years depending on the types of gases with which the apparatus is used.

D. Determination of the Speed of Sound for Gases Having Unknown Thermodynamic Properties If the thermodynamic and mechanical properties of two gases A and B of a test mixture M are known, the speed of sound of each gas ($C_A$ and $C_B$) can be calculated using the following relationships:

$$C_A = \sqrt{\frac{C_{pA} z_A RT}{(C_{pA} - z_A R) M_A}} = \sqrt{\frac{\gamma_A z_A RT}{M_A}} \quad \text{and} \tag{40}$$

$$C_B = \sqrt{\frac{C_{pB} z_B RT}{(C_{pB} - z_B R) M_B}} = \sqrt{\frac{\gamma_B z_B RT}{M_B}} \tag{41}$$

where T is the temperature of the mixture and $\gamma$ is given by:

$$\gamma = \frac{c_p}{c_p - zR} \tag{42}$$

where $c_p$ and z are given by equations (3) and (8) above.

As discussed above, the coefficients $A_c$, $B_c$, $C_c$ and $D_c$ in the expression for $c_p$ (see equation (3)), as well as other information which could lead to the determination of a specific heat value, are unknown for a variety of gases. In accordance with the present invention, it has been found that a speed of sound value for such a gas can be determined notwithstanding the lack of such information by means of the kinetic theory of gases.

It is known that all monatomic molecules have three degrees of freedom, related only to the translational mode (see Tipler, "Foundations of Modern Physics", Worth Publishers, Inc., New York, 1970). For a diatomic molecule which can be modeled as a rigid-dumbbell, the total number of degrees of freedom increases to five, with three of the degrees of freedom being related to translation and two to rotation. In the case of polyatomic molecules, the situation is more complicated, with the total number of degrees of freedom for a non-linear molecule being equal to the sum of the translational, rotational and vibrational degrees of freedom:

$$N_f = N_t + N_r + N_u = 3 + 3 + (3n-6) \tag{43}$$

where n>2 is the number of atoms in the molecule.

According to the Law of Equipartition of Energy in classical statistical mechanics, in the absence of external forces, each degree of freedom which enters quadratically into the expression for the energy of the entire system contributes, on the average, kT/2 to this energy, or $$\frac{mv_x^2}{2} + \frac{mv_y^2}{2} + \frac{mv_z^2}{2} + \frac{I\omega_1^2}{2} + \ldots = \frac{kT}{2} + \frac{kT}{2} + \frac{kT}{2} + \frac{kT}{2} + \ldots \tag{44}$$

where $k=1.381 \times 10^{-23}$ J/°K is Boltzmann's constant for an ideal gas; m is the mass of the molecule; $v_x$, $v_y$, and $v_z$ are its velocities in the x, y and z directions; I is its moment of inertia; and $\omega_1$ is its angular velocity.

As can be seen, the number of terms on both sides of equation (44) is the same, and due to the fact that each vibrational degree of freedom includes two squared terms (one for the potential and one for the kinetic energy), the total number of these terms is $$n_f = 3 + 3 + 2(3n-6) = 6(n-1) \tag{45}$$

If we take into account the principle of molecular chaos, which states that for molecules in a closed box, in the absence of external forces, all positions in the box and all velocity directions are equally probable, equation (44) can be rearranged to direction x as follows:

$$n_f \frac{mv_x^2}{2} = n_f \frac{kT}{2} \tag{46}$$

We next assume that we apply to our box an external energy (for example, acoustical energy) in direction x, which we would like to transfer from the left to the right wall of the box. In order to transfer this energy we need to supply the molecules colliding with the left wall with an additional energy e, part as heat, which goes toward increasing the internal energy $e_i$ and part to performing external (mechanical) work $e_e$. To provide the conditions of energy transfer, we need to add both these parts to the right hand side of equation (46):

$$n_f \frac{mv_x^2}{2} = n_f \frac{kT}{2} + e_i + e_e \tag{47}$$

According to the Principle of the Conservation of Energy, this additional energy e is constant. During a collision, it transfers from one molecule to its neighboring molecule located to the right of the original molecule. Each molecule, which is supplied with an additional portion of energy, can be considered to be like a Planck's oscillator. For this oscillator, the mean value of energy is determined by the methods of classical statistics (see Dougall "Atomic Physics by Max Born", Fourth Edition, Hafner Publishing Company, Inc., 1946):

$$e = \frac{\int_0^\infty e \cdot \exp\left(-\frac{e}{kT}\right) \cdot de}{\int_0^\infty \exp\left(-\frac{e}{kT}\right) \cdot de} \tag{48}$$

$$= -\frac{d}{d\left(\frac{1}{kT}\right)} \log \int_0^\infty \exp\left(-\frac{e}{kT}\right) \cdot de$$

$$= -\frac{\partial}{\partial\left(\frac{1}{kT}\right)} \log(kT) = kT$$

After the substitution of equation (48) into equation (47), we obtain the following expression for the velocity of sound propagation in the x direction:

$$V_x = \sqrt{\frac{(2 + n_f) kT}{n_f m}} \tag{49}$$

A comparison of sound velocities calculated using equations (40) and (49) for gases with well known thermodynamic and mechanical properties is set forth in Table 1. The gases used for this comparison were helium, hydrogen, nitrogen and trans-1,2-dichloroethylene (DCE). The assumed temperature and pressure were 300° K and 101,325 Pa, respectively. In this table, the first row (C) represents the speed of sound obtained using equation (40), the second row (V) represents the speed of sound obtained using equation (49), and the third row represents the percentage of error ($\delta$) between them.

As can be seen in Table 1, the difference between the two calculations is well within 1% for DCE and well within 0.1% for the other molecules. Equation (49) is thus able to provide an effective method for determining the speed of sound for a gas whose thermodynamic properties are unknown, especially since 1% accuracy can be considered acceptable when working with such a gas.

E. Mixing Rule for Compressible Gases

As indicated above, prior approaches to performing acoustical concentration measurements do not take into account the compressibility of the gases making up the test mixture, and thus implicitly assume that those gases have close to an ideal gas behavior. For most applications at least one of the constituents of the mixture is used near saturated conditions, whereby its compressibility factor is typically 2–5% less than one. As a result, errors of up to 5–10% are introduced into the concentration measurement.

In order to solve this problem, we will assume that we have a closed box of volume V from which all gases have been evacuated. If we now inject a gas A into the box (or evaporate a liquid to produce the gas), where the gas has a molecular weight $M_A$, a density $\rho_{Ap}$, and a compressibility factor $Z_{Ap}$ at a partial pressure $P_{AP}$, the mass of A in the box is $$m_A = \rho_{Ap} V = \frac{P_{Ap} M_A}{z_{Ap} RT} V \qquad (50)$$

Similarly, the mass of a gas B injected into the same volume is $$m_B = \rho_{Bp} V = \frac{P_{Bp} M_A}{z_{Bp} RT} V \qquad (51)$$

The total mass of the mixture of the two gases is:

$$m = m_A + m_B \qquad (52)$$

From the Boyle-Charles's law for the real gases, we can write:

$$\frac{P_{Ap} V}{z_{Ap} RT} = \frac{P V_A}{z_A RT} \quad \text{and} \quad \frac{P_{Bp} V}{z_{Bp} RT} = \frac{P V_B}{z_B RT} \qquad (53)$$

where $V_A = x_A V$, $V_B = x_B V$, and $x_A$ and $x_B = (1 - x_A)$ are the volumetric concentrations of gases A and B. Combining equations (50) through (53) we obtain $$m = \frac{PV}{RT}\left(\frac{M_A}{z_A} x_A + \frac{M_B}{z_B} x_B\right) \qquad (54)$$

From equation (54) we can conclude that the accuracy of the mixing rules can be improved for real gases by taking into account the compressibility factors. In particular, such improvement can be achieved by using the following mixing rule for evaluating of the molecular weight of a binary mixture instead of the previously used mixing rule set forth above in equation (5):

$$M_M = \sum_i x_i \frac{M_i}{z_i} = \frac{M_A}{z_A} x_A + \frac{M_B}{z_B} x_B \qquad (55)$$

Using this mixing rule, the equation for the speed of sound of a mixture of compressible gases is $$C_M = \left(\frac{RT}{\sum_i x_i \frac{M_i}{z_i}} \times \frac{\sum_i x_i c_{Pi}}{\sum_i x_i (c_{Pi} - z_i R)}\right)^{1/2} \qquad (56)$$

F. Concentration Determinations

The above equation (56) can be used in various applications to determine the concentration of a mixture of real gases, e.g., a binary mixture of real gases. Examples of such applications are as follows.

(1) Calculation of the Volumetric Concentration of a Gas in a Total Volume Under Actual Conditions Some industries are interested in measuring the volumetric concentration of gas A relative to the total volume of a binary mixture of gases A and B under actual conditions. Such measurements can, for example, be used to detect the possibility of the appearance of an explosive mixture.

In accordance with the invention, it is possible to calculate this parameter for compressible fluids by means of equation (56).

If we denote $$a = \frac{(c_{PA} - z_A R) - (c_{PB} - z_B R)}{c_{PB} - z_B R} \times \frac{\frac{M_A}{z_A} - \frac{M_B}{z_B}}{\frac{M_B}{z_B}} \times C_M^2$$

$$b = \left(\frac{(c_{PA} - z_A R) - (c_{PB} - z_B R)}{c_{PB} - z_B R} \times \frac{\frac{M_A}{z_A} - \frac{M_B}{z_B}}{\frac{M_B}{z_B}}\right) \times$$

$$C_M^2 - \frac{c_{PA} - c_{PB}}{c_{PB}} \times C_B^2$$

and $$c = C_M^2 - C_B^2$$

where $C_M$ is the measured speed of sound for the mixture, and $c_p$ and $C_B$ are given by equations (3) and (41), respectively, then the volumetric concentration of gas A ($Q_A$) relative to the total volume of the binary mixture ($Q_M$) can be written:

$$x_A = \frac{Q_A}{Q_M} = \frac{\sqrt{b^2 - 4ac} - b}{2a} \qquad (57)$$

(2) Relative Volumetric Concentrations of a Binary Gas Mixture Under Actual Conditions The relative volumetric concentrations of gases A and B in a binary mixture can be found using equation (57) as follows:

$$\frac{Q_A}{Q_B} = \frac{\frac{Q_A}{Q_M}}{1 - \frac{Q_A}{Q_M}} \qquad (58)$$

(3) Relative Mass Concentrations of a Binary Gas Mixture

The volumetric flow rate Q and mass flow G of a gas are related as follows $$G = \rho Q \qquad (59)$$

where ρ is the gas' density given by the equation $$\rho = \frac{PM}{zRT} \quad (60)$$

Accordingly, the relative mass concentrations of a binary gas mixture can be written:

$$\frac{G_A}{G_B} = \frac{Q_A}{Q_B} \times \frac{M_A z_B}{M_B z_A} \quad (61)$$

(4) Relative Volumetric Concentrations of a Binary Gas at Standard Conditions

The relative volumetric concentrations of a binary gas mixture under standard conditions, i.e., a temperature of 0° C. and a pressure of 101,325 Pa, can be written:

$$\frac{Q_{A_o}}{Q_{B_o}} = \frac{Q_A}{Q_B} \times \frac{z_{A_o} z_B}{z_A z_{B_o}} \quad (62)$$

where $z_{A_o}$ and $z_{B_o}$ are the compressibility factors of gases A and B at standard conditions.

(5) Concentration in Terms of the Mass of a Gas of Interest in Relation to the Volumetric Flow of a Carrier Gas at Standard Conditions Concentration in terms of the mass of a gas of interest ($G_A$) in relation to the volumetric flow of a carrier gas at standard conditions ($Q_{BO}$) is used widely in a variety of applications. Using equation (59) to (61), the ratio $G_A/Q_{BO}$ can be written:

$$\frac{G_A}{Q_{B_o}} = \frac{Q_A}{Q_B} \times \frac{P_o M_A z_B}{R T_o z_A z_{B_o}} \quad (63)$$

In practice, one or more of the above concentration expressions (or other expressions as desired) are evaluated by, for example, processing network 29 of FIGS. 2 and 6. The calculated concentration values are then used in, for example, a feedback control loop system or are delivered to an external device, such as alarm system, indicator, or the like.

G. Feedback Control Systems

In order to control and monitor the flow rate of a carrier gas, manufacturers are currently using mass flow controllers which are able to measure and control volumetric flow rates of a carrier gas at standard conditions ($Q_{Bo}$) to an accuracy of 0.5–1.0%. After leaving the mass flow controller, the carrier gas typically passes into a bubbler where it picks up a gas of interest which is usually in liquid form but may also be a sublimating solid.

The pick-up rate is not affected by the flow rate of the carrier gas, i.e., if the flow rate of the carrier gas is doubled, with temperature and pressure held constant, the pick-up rate of the gas of interest is also doubled. However, the pick-up rate is a function of bubbler temperature and, to a lesser degree, a function of pressure. As a result, the concentration of the gas of interest will vary with exogenous disturbances to the system which change the temperature and/or pressure at the bubbler. Such variations can be significant and represent an unsolved problem in numerous industrial settings.

In accordance with the invention, this problem is solved by means of a feedback control loop system which uses a measured value of the mass flow rate of the gas of interest ($G_A$) to control the mass flow controller for the carrier gas.

FIG. 29 shows a block diagram of a representative embodiment of the control system of the invention. The system achieves control of the mass flow rate of the gas of interest by measuring the concentration of the gas after it has been mixed with the carrier gas. Preferably the concentration of the gas of interest in the mixture is determined acoustically employing the techniques discussed above, although other approaches for making such a concentration measurement can be used if desired.

As shown in FIG. 29, a desired value for the mass flow rate of the gas of interest ($G_{Ain}$) is provided to processing network 29 from, for example, an external computer. This value, which preferably is in digital form, is compared to the existing mass flow rate ($G_A$), and a differential signal ($\Delta G$) is generated and directed to regulator 61. Regulator 61 can be, for example, a proportional-integral control regulator, which is capable of providing the control loop system with a stable and fast step response.

Digital to analog converter (DAC) 62 receives the output signal of regulator 61 in digital form, and converts it to an analog voltage compatible with the mass flow controller (MFC) 63, e.g., an analog voltage in the range from 0 to 5 volts. If the differential signal ($\Delta G$) is not zero, it win cause changes in the mass flow rate of the carrier gas.

Analog to digital converter (ADC) 64 converts the output analog voltage of the MFC, which represents the current volumetric flow rate of the carrier gas at standard conditions, to a digital value ($Q_{Bo}$). This value is sent to the first input of multiplier 65, which multiplies this value by a measured/calculated concentration value for the binary mixture ($G_A/Q_{Bo}$). This measured/calculated concentration value is preferably obtained as described above from a measurement of the speed of sound of the mixture, although it can be obtained in other ways if desired. The product of $Q_{Bo}$ and $G_A/Q_{Bo}$ gives $G_A$, the true mass flow rate of the gas of interest, which as described above is compared with $G_{Ain}$ to produce $\Delta G$.

Experimental tests of the feedback control loop system of FIG. 29 have shown that the system has high repeatability (to 0.1%) and high accuracy (to 0.5–1.0%) when used with state of the art mass flow controllers, e.g., the mass flow controller manufactured by MKS Instruments, Inc., Andover, Md. and sold under the product designation MKS Type 1679A MASS-FLO® Controller. In addition, the system has a response time which is significantly faster than prior art systems which have employed bubbler temperature or pressure as the controlled variable rather than carrier gas flow rate, e.g., a response time on the order of 50 to 100 milliseconds for the system of the invention compared to minutes for the prior art. Feedback control loops having designs other than that shown in FIG. 29 can of course be used in the practice of the invention.

Without intending to limit it in any manner, the present invention will be more fully illustrated by the following example.

EXAMPLE

This example compares the results of using the mixing rule of equation (56) of the present invention with that of equation (7) of the prior art in determining the concentration of a gas of interest in a binary mixture from a speed of sound measurement performed on the mixture. For purposes of illustration, the binary mixture has been assumed to comprise trans-1,2-dichloroethylene (the gas of interest) and nitrogen (the carrier gas). The thermodynamic and mechanical properties of both these gases are well known.

The results of the comparison are shown in FIG. 30, where the solid curve is based on the mixing rule of equation (56) and the dashed curve on that of equation (7). The measured speed of sound for a mixture of trans-1,2-dichloroethylene (DCE) and nitrogen produced by a bubbler system operating at a temperature of 20° C. and a pressure of 760 torr is 242.54 m/s. From FIG. 30, we can see that this speed of sound corresponds to a $G_{DCE}/G_{N2}$ ratio of 1.8271 when the mixing rule of equation (56) is used and 1.8945 with the prior art mixing rule is used. In terms of semiconductor manufacturing, concentration measurements need to be accurate to at least 1%, thus making the 3.7% error introduced by the prior art mixing rule unacceptable.

The mathematical operations described herein can be performed using a variety of computers and software. For example, commercially available programs and computer systems configured to run those programs in accordance with the program manufacturer's specifications can be used in the implementation of the invention. An example of such a program is MATHEMATICA, sold by Wolfram Research, Champaign, Ill. Dedicated programs can also be written in a variety of computer programming languages, such as C/C++, Visual Basic, and assembly languages. Those programs can be stored on various storage media, e.g., removable magnetic discs, non-removable magnetic discs, or optical discs, for use and/or distribution. Similarly, input and output data relating to those programs can be stored on various types of storage media.

The computer system used with the acoustical sensor can comprise a general purpose scientific computer and its associated peripherals, such as the computers and peripherals currently being manufactured by Digital Equipment Corporation, IBM, Hewlett-Packard, Sun MicroSystems or the like. Dedicated digital processors can also be used in the practice of the invention if desired. Preferably, the processing portion of the computer system should have the following characteristics: a processing rate of 30 million floating point operations per second; a word length of 32 bits floating point; at least 4 megabytes of memory; and at least 2 megabytes of non-volatile storage such as a disc, EPROM, or the like. The system should include means for inputting data and means for outputting results both in electronic and visual form. The output can also be stored on a disk drive, tape drive, or the like for further analysis and/or subsequent display.

Various patents and publications have been referred to above in connection with the description of the invention and the state of the art. The contents of these documents are incorporated herein by reference.

Although specific embodiments of the invention have been described and illustrated, it is to be understood that modifications can be made without departing from the invention's spirit and scope. For example, although the invention has been illustrated in terms of a flowing test medium, it can also be used with non-flowing media. Also, although the invention is primarily intended for use with gaseous media, various of its aspects can be used in connection with acoustical measurements on liquids and solids as discussed above.

A variety of other modifications which do not depart from the scope and spirit of the invention will be evident to persons of ordinary skill in the art from the disclosure herein. The following claims are intended to cover the specific embodiments set forth herein as well as such modifications, variations, and equivalents.

TABLE 1

|  | Helium He | Hydrogen $H_2$ | Nitrogen $N_2$ | DCE $C_2H_2Cl_2$ |
| --- | --- | --- | --- | --- |
| C (m/s) | 1019.34 | 1316.30 | 352.83 | 166.70 |
| V (m/s) | 1019.25 | 1316.42 | 353.11 | 165.69 |
| δ (%) | 0.01 | 0.01 | 0.08 | 0.61 |

What is claimed is:

1. Apparatus for use with (i) a transmitter which produces a pulse of acoustical energy (the transmitted pulse) which passes through a gas, liquid, or solid, and (ii) a receiver which detects the transmitted pulse after its passage through the gas, liquid, or solid (the detected pulse), said apparatus comprising:

(a) cross-correlating means associated with the receiver for performing a cross-correlation between (i) a stored calibration waveform representing the transmitted pulse and (ii) the detected pulse, said cross-correlating means producing a cross-correlation function for the detected pulse; and (b) peak determining means for determining the peak of said cross-correlation function, said peak being indicative of the time the detected pulse was detected by the receiver;

wherein the stored calibration waveform is not directly derived from the transmitted pulse but is determined during calibration of the apparatus and stored prior to the production of said transmitted pulse by the transmitter.

2. The apparatus of claim 1 wherein the transmitted pulse comprises acoustical oscillations having a center frequency and the stored calibration waveform is determined using a gas which has: (i) either a known specific heat, compressibility, and molecular weight, or a known speed of sound, and (ii) a close to ideal gas behavior at the center frequency.

3. The apparatus of claim 2 wherein the stored calibration waveform is determined by averaging a large number of detected and stored pulses.

4. The apparatus of claim 1 wherein the cross-correlation is performed by:

(i) performing a fast Fourier transform of the detected pulse to produce a Fourier transformed detected pulse;

(ii) multiplying the Fourier transformed detected pulse by the complex conjugate of a Fourier transform of the stored calibration waveform to produce a Fourier space cross-correlation function; and (iii) performing an inverse fast Fourier transform of said Fourier space cross-correlation function and taking the real part of said inverse fast Fourier transform to produce said cross-correlation function.

5. The apparatus of claim 1 wherein the peak of the cross-correlation function is determined by:

(i) identifying the largest amplitude of the cross-correlation function and two amplitudes adjacent to the largest amplitude;

(ii) fitting a second order polynomial to said three amplitudes; and (iii) determining the peak of the cross-correlation function from said second order polynomial.

6. The apparatus of claim 2 wherein the transmitted pulse has leading and trailing cycles and is windowed so that said leading and trailing cycles taper from zero to full amplitude.

7. The apparatus of claim 2 wherein the transmitted pulse is frequency modulated.

8. The apparatus of claim 2 wherein the transmitter and receiver are separated by a distance which defines a wraparound time and the transmitted pulse has a duration which is longer than the wraparound time.

9. A method for testing a gas, liquid, or solid comprising:
(a) producing a pulse of acoustical energy which passes through the gas, solid, or liquid (the transmitted pulse);
(b) detecting the transmitted pulse after it has passed through the gas, solid, or liquid (the detected pulse);
(c) performing a cross-correlation between (i) a stored calibration waveform representing the transmitted pulse and (ii) the detected pulse, said cross-correlation producing a cross-correlation function for the detected pulse; and
(d) determining the peak of said cross-correlation function, said peak being indicative of the time the detected pulse was detected in step (b);
wherein the stored calibration waveform is not directly derived from the transmitted pulse but is determined during a calibration procedure and stored prior to the production of said transmitted pulse in step (a).

10. The method of claim 9 wherein the transmitted pulse comprises acoustical oscillations having a center frequency and the stored calibration waveform is determined using a gas which has: (i) either a known specific heat, compressibility, and molecular weight, or a known speed of sound, and (ii) a close to ideal gas behavior at the center frequency.

11. The method of claim 10 wherein the stored calibration waveform is determined by averaging a large number of detected and stored pulses.

12. The method of claim 9 wherein the cross-correlation is performed by:
(i) performing a fast Fourier transform of the detected pulse to produce a Fourier transformed detected pulse;
(ii) multiplying the Fourier transformed detected pulse by the complex conjugate of a Fourier transform of the stored calibration waveform to produce a Fourier space cross-correlation function; and
(iii) performing an inverse fast Fourier transform of said Fourier space cross-correlation function and taking the real part of said inverse fast Fourier transform to produce said cross-correlation function.

13. The method of claim 9 wherein the peak of the cross-correlation function is determined by:
(i) identifying the largest amplitude of the cross-correlation function and two amplitudes adjacent to the largest amplitude;
(ii) fitting a second order polynomial to said three amplitudes; and
(iii) determining the peak of the cross-correlation function from said second order polynomial.

14. The method of claim 9 wherein the transmitted pulse has leading and trailing cycles and is windowed so that said leading and trailing cycles taper from zero to full amplitude.

15. The method of claim 9 wherein the transmitted pulse is frequency modulated.

16. The method of claim 9 wherein steps (a) and (b) are performed at locations which define a wraparound time and the transmitted pulse has a duration which is longer than the wraparound time.

17. Apparatus for use with (i) a transmitter which produces a pulse of acoustical energy (the original pulse) which passes through a gas, liquid, or solid, and (ii) a receiver which detects the pulse after its passage through the gas, liquid, or solid (the detected pulse), said apparatus comprising:
(a) cross-correlating means associated with the receiver for performing a cross-correlation between a waveform representing the original pulse and the detected pulse, said cross-correlating means producing a cross-correlation function for the detected pulse; and
(b) peak determining means for determining the peak of said cross-correlation function, said peak being indicative of the time the detected pulse was detected by the receiver;
wherein the peak of the cross-correlation function is determined by:
(i) identifying the largest amplitude of the cross-correlation function and two amplitudes adjacent to the largest amplitude;
(ii) fitting a second order polynomial to said three amplitudes; and
(iii) determining the peak of the cross-correlation function from said second order polynomial.

18. Apparatus for use with (i) a transmitter which produces a pulse of acoustical energy (the original pulse) which passes through a gas, liquid, or solid, and (ii) a receiver which detects the pulse after its passage through the gas, liquid, or solid (the detected pulse), said apparatus comprising:
(a) cross-correlating means associated with the receiver for performing a cross-correlation between a waveform representing the original pulse and the detected pulse, said cross-correlating means producing a cross-correlation function for the detected pulse; and
(b) peak determining means for determining the peak of said cross-correlation function, said peak being indicative of the time the detected pulse was detected by the receiver;
wherein the transmitter and receiver are separated by a distance which defines a wraparound time and the original pulse has a duration which is longer than the wraparound time.

19. A method for testing a gas, liquid, or solid comprising:
(a) producing a pulse of acoustical energy which passes through the gas, solid, or liquid (the original pulse);
(b) detecting the pulse after it has passed through the gas, solid, or liquid (the detected pulse);
(c) performing a cross-correlation between a waveform representing the original pulse and the detected pulse, said cross-correlation producing a cross-correlation function for the detected pulse; and
(d) determining the peak of said cross-correlation function, said peak being indicative of the time the detected pulse was detected in step (b);
wherein the peak of the cross-correlation function is determined by:
(i) identifying the largest amplitude of the cross-correlation function and two amplitudes adjacent to the largest amplitude;
(ii) fitting a second order polynomial to said three amplitudes; and
(iii) determining the peak of the cross-correlation function from said second order polynomial.

20. A method for testing a gas, liquid, or solid comprising:
(a) producing a pulse of acoustical energy which passes through the gas, solid, or liquid (the original pulse);
(b) detecting the pulse after it has passed through the gas, solid, or liquid (the detected pulse);
(c) performing a cross-correlation between a waveform representing the original pulse and the detected pulse, said cross-correlation producing a cross-correlation function for the detected pulse; and (d) determining the peak of said cross-correlation function, said peak being indicative of the time the detected pulse was detected in step (b);

wherein steps (a) and (b) are performed at locations which define a wraparound time and the original pulse has a duration which is longer than the wraparound time.

* * * * *